United States Patent [19]
Tanzi et al.

[11] Patent Number: 5,643,726
[45] Date of Patent: Jul. 1, 1997

[54] METHODS FOR MODULATING TRANSCRIPTION FROM THE AMYLOID β-PROTEIN PRECURSOR (APP) PROMOTER

[75] Inventors: Rudolph E. Tanzi, Canton; Dora M. Kovacs, Cambridge, both of Mass.

[73] Assignee: The General Hospital Corporation, Charlestown, Mass.

[21] Appl. No.: 339,152

[22] Filed: Nov. 10, 1994

[51] Int. Cl.$^6$ .............................. C12Q 1/68; C12N 15/63
[52] U.S. Cl. .................................................. 435/6; 935/36
[58] Field of Search ........................... 435/172.3, 320.1; 536/23.1, 24.1; 935/41

[56] References Cited

U.S. PATENT DOCUMENTS 5,196,524  3/1993  Gustafson et al. ................ 536/23.2

OTHER PUBLICATIONS

Chernak, J.M., "Structural features of the 5' upstream regulatory region of the gene encoding rat amyloid precursor protein," *Gene* 133:255–260 (1993).

Fukuchi et al., "Increased Expression of β-Amyloid Protein Precursor and Microtubule–Associated Protein τ During the Differentiation of Murine Embryonal Carcinoma Cells," *J. Neurochem.* 58:1863–1873 (1992).

Glenner and Wong, "Alzheimer's Disease: Initial Report of the Purification and Characterization of a Novel Cerebrovascular Amyloid Protein," *Biochem. Biophys. Res. Commun.* 120(3):885–890 (1984).

Gregor et al., "The adenovirus major late transcription factor USF is a member of the helix–loop–helix group of regulatory proteins and binds to DNA as a dimer," *Genes Dev.* 4:1730–1740 (1990).

Hoffman and Chernak, "The Rat Amyloid Precursor Protein Promoter Contains Two DNA Regulatory Elements Which Influence High Level Gene Expression," *Biochem. Biophys. Res. Commun.* 201(2):610–617 (1994).

Hu et al., "Transcription factor AP–4 contains multiple dimerization domains that regulate dimer specificity," *Genes Dev.* 4:1741–1752 (1990).

Izumi et al., "Positive and negative regulatory elements for the expression of the Alzheimer's disease amyloid precursor–encoding gene in mouse," *Gene* 112:189–195 (1992).

Masters et al., "Amyloid plaque core protein in Alzheimer disease and Down syndrome," *PNAS USA* 82:4245–4249 (1985).

Masters et al., "Neuronal origin of a cerebral amyloid: neurofibrillary tangles of Alzheimer's disease contain the same protein as the amyloid of plaque cores and blood vessels," *EMBO J.* 4:2757–2763 (1985).

Mermod et al., "Enhancer binding factors AP–4 and AP–1 act in concert to activate SV40 late transcription in vitro," *Nature* 332:557–561 (1988).

Miner et al., "Cold–Induced Alterations in the Binding of Adrenomedullary Nuclear Proteins to the Promoter Region of the Tyrosine Hydroxylase Gene," *J. Neurosci. Res.* 33:10–18 (1992).

Murre et al., "A New DNA Binding and Dimerization Motif in Immunoglobulin Enhancer Binding, daughterless, MyoD, and myc Proteins," *Cell* 56:777–783 (1989).

(List continued on next page.)

*Primary Examiner*—David Guzo
*Assistant Examiner*—Robert Schwartzman
*Attorney, Agent, or Firm*—Sterne, Kessler, Goldstein & Fox, P.L.L.C.

[57] ABSTRACT

The application concerns methods for modulating transcription from the amyloid β-protein precursor (APP) promoter. The upstream stimulatory factor (USF) is described as being capable of activating transcription from the APP promoter. Also described are USF binding compounds which are capable of down-regulating expression from the APP promoter. Preferred USF binding compounds are the amyloid precursor-like proteins APLP1 and APLP2. The application further concerns a screening assay for determining which candidate USF binding compounds are capable of causing down-regulation of transcription from the APP promoter.

18 Claims, 34 Drawing Sheets

HUMAN APP PROMOTER

5' GGGCCGGATCAGCTGACTCGCCTGGCTCT 3'  DK 1 FRAGMENT

OTHER PUBLICATIONS

Nordeen, S.K., "Luciferase Reporter Gene Vectors for Analysis of Promoters and Enhancers," *BioTechniques* 6(5):454–457 (1988).

Pognonec and Roeder, "Recombinant 43-kDa USF Binds to DNA and Activates Transcription in a Manner Indistinguishable from That of Natural 43/44-kDa USF," *Mol. Cell. Biol.* 11(10):5125–5136 (1991).

Pollwein, P., "Overlapping Binding Sites of Two Different Transcription Factors in the Promoter of the Human Gene for the Alzheimer Amyloid Precursor Protein," *Biochem. Biophys. Res. Commun.* 190(2):637–647 (1993).

Pollwein et al., "The expression of the amyloid precursor protein (APP) is regulated by two GC-elements in the promoter," *Nucleic Acids Res.* 20(1):63–68 (1992).

Quitschke and Goldgaber, "The Amyloid β-Protein Precursor Promoter," *J. Biol. Chem.* 267(24):17362–17368 (1992).

Quon et al., "Formation of β-amyloid protein deposits in brains of transgenic mice," *Nature* 352:239–241 (1991).

Read et al., "The helix–loop–helix transcription factor USF (upstream stimulating factor) binds to a regulatory sequence of the human insulin gene enhnacer," *Biochem. J.* 295:233–237 (1993).

Reisman and Rotter, "The helix–loop–helix containing transcription factor USF binds to and transactivates the promoter of the p53 tumor suppressor gene," *Nucleic Acids Res.* 21(2):345–350 (1993).

Riccio et al., "Transforming Growth Factor β1-Responsive Element: Closely Associated Binding Sites for USF and CCAAT-Binding Transcription Factor–Nuclear Factor I in the Type 1 Plasminogen Activator Inhibitor Gene," *Mol. Cell Biol.* 12(4):1846–1855 (1992).

Roy et al., "Cooperative interaction of an initiator–binding transcription initiation factor and the helix–loop–helix activator USF," *Nature* 354:245–248 (1991).

Rumble et al., "Amyloid A4 Protein And Its Precursor In Down's Syndrome And Alzheimer's Disease," *New Engl. J. Med.* 320(22):1446–1452 (1989).

Salbaum et al., "The promoter of Alzheimer's disease amyloid A4 precursor gene," *EMBO J.* 7:2807–2813 (1988).

Schmechel et al., "Cellular Localization of Messenger RNA Encoding Amyloid–Beta–Protein in Normal Tissue and in Alzheimer Disease," *Alzheimer Disease and Associated Disorders* 2(2):96–111 (1988).

Tanzi et al., "Amyloid β Protein Gene: cDNA, mRNA Distribution, and Genetic Linkage Near the Alzheimer Locus," *Science* 235:880–884 (1987).

Tapscott et al., "MyoD1: A Nuclear Phosphoprotein Requiring a Myc Homology Region to Convert Fibroblasts to Myoblasts," *Science* 242:405–411 (1988).

Wasco et al., "The Amyloid Precursor–like Protein (APLP) Gene Maps to the Long Arm of Human Chromosome 19," *Genomics* 15:237–239 (1993).

Wasco et al., "Identification of a mouse brain cDNA that encodes a protein related to the Alzheimer disease–associated amyloid β protein precursor," *PNAS USA* 89:10758–10762 (1992).

Wasco et al., "Isolation and characterization of APLP2 encoding a homologue of the Alzheimer's associated amyloid β protein precursor," *Nature Genet.* 5:95–100 (1993).

Wirak et al., "Deposits of Amyloid β Protein in the Central Nervous System of Transgenic Mice," *Science* 253:323–325 (1991).

Goldgaber et al. (1989) Proc Natl Acad Sci USA 86:7606–7610 Oct. 1989.

Quitschke, W.W., "Two Nuclear Factor Binding Domains Activate Expression from the Human Amyloid β-Protein Precursor Promoter," *J. of Biological Chemistry* 269 (No. 33):21229–21233 (Aug. 19, 1994).

Trejo, J., et al., "A Direct Role for Protein Kinase C and the Transcription Factor Jun/AP-1 in the Regulation of the Alzheimer's β-Amyloid Precursor Protein Gene," *J. of Biological Chemistry* 269 (34):21682–21690 (Aug. 26, 1994).

International Search Report from International Appl. No. PCT/US95/14416; date of mailing: Feb. 28, 1996.

```
CGGCACGAGG TGGCGCTGGG AGCTCCTGTC ACCGCTGGGG CCGGGTAGGG GCGGGCGGGA              60

GCGCAGGGAC GTGAGGGCCG AGCGGAC ATG GGG CCC ACC AGC CCC GCC GCT                  111
                              Met Gly Pro Thr Ser Pro Ala Ala
                               1               5

CGC GGT CAG GGT CGC CGC TGG CGA CCG CCG CTG CCG CTG TTG CTG CCA                159
Arg Gly Gln Gly Arg Arg Trp Arg Pro Pro Leu Pro Leu Leu Leu Pro
         10              15                  20

CTG TCA TTG CTG CTT CTG CGC GCG CAG CTC GCC GTC GGG AAC CTG GCT                207
Leu Ser Leu Leu Leu Leu Arg Ala Gln Leu Ala Val Gly Asn Leu Ala
 25              30                  35                  40

GTT GGG AGC CCC AGC GCG GCC GAG GCT CCG GGG TCG GCT CAA GTG GCT                255
Val Gly Ser Pro Ser Ala Ala Glu Ala Pro Gly Ser Ala Gln Val Ala
                 45                  50                  55

GGA CTA TGT GGG CGT CTA ACC CTT CAC CGG GAC TTG CGC ACC GGC CGC                303
Gly Leu Cys Gly Arg Leu Thr Leu His Arg Asp Leu Arg Thr Gly Arg
             60                  65                  70

TGG GAA CCA GAC CCA CAG CGA TCA CGA CGC TGT CTT CTG GAC CCG CAG                351
Trp Glu Pro Asp Pro Gln Arg Ser Arg Arg Cys Leu Leu Asp Pro Gln
                 75                  80                  85

CGC GTG CTG GAG TAC TGC AGA CAG ATG TAC CCC GAG CTG CAC ATA GCA                399
Arg Val Leu Glu Tyr Cys Arg Gln Met Tyr Pro Glu Leu His Ile Ala
             90                  95                 100

CGC GTG GAG CAG GCT GCA CAG GCC ATC CCG ATG GAG CGC TGG TGT GGG                447
Arg Val Glu Gln Ala Ala Gln Ala Ile Pro Met Glu Arg Trp Cys Gly
105                 110                 115                 120

GGT ACC CGG AGT GGC AGA TGC GCC CAC CCC CAC CAT GAG GTT GTG CCC                495
Gly Thr Arg Ser Gly Arg Cys Ala His Pro His His Glu Val Val Pro
                125                 130                 135

TTC CAT TGC CTG CCT GGC GAA TTC GTG AGT GAA GCC CTG CTA GTG CCC                543
Phe His Cys Leu Pro Gly Glu Phe Val Ser Glu Ala Leu Leu Val Pro
                140                 145                 150
```

FIG.10A

| | | | | | | | | | | | | | | |
|---|---|---|---|---|---|---|---|---|---|---|---|---|---|---|
| GAA | GGC | TGT | CGG | TTC | TTG | CAC | CAG | GAG | CGT | ATG | GAC | CAG | TGT | GAG | AGT | 591 |
| Glu | Gly | Cys | Arg | Phe | Leu | His | Gln | Glu | Arg | Met | Asp | Gln | Cys | Glu | Ser | |
| | | 155 | | | | 160 | | | | 165 | | | | | | |

| TCA | ACC | AGG | AGG | CAT | CAG | GAG | GCT | CAG | GAG | GCC | TGC | AGC | TCT | CAG | GGC | 639 |
| Ser | Thr | Arg | Arg | His | Gln | Glu | Ala | Gln | Glu | Ala | Cys | Ser | Ser | Gln | Gly | |
| 170 | | | | 175 | | | | 180 | | | | | | | | |

| CTC | ATC | CTC | CAC | GGC | TCT | GGC | ATG | CTT | TTG | CCC | TGT | GGC | TCT | GAT | CGG | 687 |
| Leu | Ile | Leu | His | Gly | Ser | Gly | Met | Leu | Leu | Pro | Cys | Gly | Ser | Asp | Arg | |
| 185 | | | | 190 | | | | 195 | | | | 200 | | | | |

| TTC | CGA | GGT | GTG | GAG | TAT | GTA | TGC | TGT | CCA | CCT | CCC | GCA | ACT | CCC | AAC | 735 |
| Phe | Arg | Gly | Val | Glu | Tyr | Val | Cys | Cys | Pro | Pro | Pro | Ala | Thr | Pro | Asn | |
| | | | | 205 | | | | 210 | | | | 215 | | | | |

| CCA | TCT | GGG | ATG | GCA | GCT | GGT | GAC | CCC | TCT | ACC | CGG | TCC | TGG | CCC | CTG | 783 |
| Pro | Ser | Gly | Met | Ala | Ala | Gly | Asp | Pro | Ser | Thr | Arg | Ser | Trp | Pro | Leu | |
| | | | 220 | | | | 225 | | | | 230 | | | | | |

| GGG | GGC | AGA | GCA | GAG | GGA | GGT | GAG | GAT | GAA | GAG | GAG | GTG | GAA | TCT | TTC | 831 |
| Gly | Gly | Arg | Ala | Glu | Gly | Gly | Glu | Asp | Glu | Glu | Glu | Val | Glu | Ser | Phe | |
| | | 235 | | | | 240 | | | | 245 | | | | | | |

| CCT | CAG | CCA | GTA | GAC | GAT | TAC | TTC | GTA | GAG | CCC | CCT | CAG | GCT | GAA | GAA | 879 |
| Pro | Gln | Pro | Val | Asp | Asp | Tyr | Phe | Val | Glu | Pro | Pro | Gln | Ala | Glu | Glu | |
| | 250 | | | | 255 | | | | 260 | | | | | | | |

| GAA | GAG | GAA | GAG | GAG | GAA | GAA | AGG | GCC | CCA | CCT | CCC | AGC | TCC | CAC | ACC | 927 |
| Glu | Glu | Glu | Glu | Glu | Glu | Glu | Arg | Ala | Pro | Pro | Pro | Ser | Ser | His | Thr | |
| 265 | | | | 270 | | | | 275 | | | | 280 | | | | |

| CCT | GTC | ATG | GTT | AGC | AGA | GTC | ACT | CCC | ACC | CCA | AGG | CCT | ACT | GAT | GGT | 975 |
| Pro | Val | Met | Val | Ser | Arg | Val | Thr | Pro | Thr | Pro | Arg | Pro | Thr | Asp | Gly | |
| | | | | 285 | | | | 290 | | | | 295 | | | | |

| GTG | GAT | GTT | TAC | TTT | GGC | ATG | CCT | GGG | GAA | ATC | GGC | GAG | CAT | GAG | GGT | 1023 |
| Val | Asp | Val | Tyr | Phe | Gly | Met | Pro | Gly | Glu | Ile | Gly | Glu | His | Glu | Gly | |
| | | | 300 | | | | 305 | | | | 310 | | | | | |

FIG.10B

```
TTC CTG AGG GCC AAG ATG GAC CTG GAG GAG CGT AGG ATG CGC CAG ATT    1071
Phe Leu Arg Ala Lys Met Asp Leu Glu Glu Arg Arg Met Arg Gln Ile
        315                 320                 325

AAT GAG GTG ATG CGT GAA TGG GCC ATG GCT GAC AGC CAA TCT AAG AAC    1119
Asn Glu Val Met Arg Glu Trp Ala Met Ala Asp Ser Gln Ser Lys Asn
        330                 335                 340

CTG CCA AAG GCG GAC AGG CAG GCC CTG AAT GAG CAC TTC CAG TCC ATT    1167
Leu Pro Lys Ala Asp Arg Gln Ala Leu Asn Glu His Phe Gln Ser Ile
345                 350                 355                 360

CTG CAG ACC CTG GAA GAA CAA GTG TCT GGT GAA CGG CAA CGC CTG GTG    1215
Leu Gln Thr Leu Glu Glu Gln Val Ser Gly Glu Arg Gln Arg Leu Val
                365                 370                 375

GAG ACC CAC GCC ACC AGA GTC ATC GCT CTG ATC AAC GAC CAG CGC CGA    1263
Glu Thr His Ala Thr Arg Val Ile Ala Leu Ile Asn Asp Gln Arg Arg
        380                 385                 390

GCA GCC CTG GAA GGT TTC CTG GCA GCC TTA CAG GGC GAT CCG CCT CAG    1311
Ala Ala Leu Glu Gly Phe Leu Ala Ala Leu Gln Gly Asp Pro Pro Gln
        395                 400                 405

GCT GAG CGA GTT CTG ATG GCC CTG AGG CGC TAC CTG CGC GCC GAG CAG    1359
Ala Glu Arg Val Leu Met Ala Leu Arg Arg Tyr Leu Arg Ala Glu Gln
        410                 415                 420

AAA GAG CAG AGG CAC ACT CTG AGG CAC TAC CAG CAC GTG GCC GCA GTG    1407
Lys Glu Gln Arg His Thr Leu Arg His Tyr Gln His Val Ala Ala Val
425                 430                 435                 440

GAT CCT GAG AAG GCC CAG CAG ATG CGC TTT CAG GTC CAG ACC CAC CTT    1455
Asp Pro Glu Lys Ala Gln Gln Met Arg Phe Gln Val Gln Thr His Leu
                445                 450                 455

CAG GTG ATC GAA GAG CGA ATG AAT CAG AGC CTG GGG CTG CTC GAC CAG    1503
Gln Val Ile Glu Glu Arg Met Asn Gln Ser Leu Gly Leu Leu Asp Gln
        460                 465                 470
```

FIG.10C

```
AAC CCT CAC CTG GCT CAG GAG CTG CGG CCA CAG ATC CAG GAG CTT CTC    1551
Asn Pro His Leu Ala Gln Glu Leu Arg Pro Gln Ile Gln Glu Leu Leu
        475                 480                 485

CTT GCT GAA CAC TTG GGT CCC AGT GAA CTG GAC GCC TCT GTG CCC GGG    1599
Leu Ala Glu His Leu Gly Pro Ser Glu Leu Asp Ala Ser Val Pro Gly
        490                 495                 500

AGC AGC AGT GAG GAC AAA GGT AGC CTC CAG CCT CCC GAA TCC AAG GAC    1647
Ser Ser Ser Glu Asp Lys Gly Ser Leu Gln Pro Pro Glu Ser Lys Asp
505                 510                 515                 520

GAT CCC CCA GTG ACC CTT CCA AAA GGG TCC ACA GAT CAA GAG TCA TCC    1695
Asp Pro Pro Val Thr Leu Pro Lys Gly Ser Thr Asp Gln Glu Ser Ser
                525                 530                 535

TCC TCT GGG AGA GAG AAG CTA ACT CCA CTG GAG CAG TAT GAG CAA AAG    1743
Ser Ser Gly Arg Glu Lys Leu Thr Pro Leu Glu Gln Tyr Glu Gln Lys
                540                 545                 550

GTG AAT GCA TCC GCC CCG AGG GGG TTT CCG TTC CAC TCG TCA GAT ATC    1791
Val Asn Ala Ser Ala Pro Arg Gly Phe Pro Phe His Ser Ser Asp Ile
        555                 560                 565

CAG CGG GAT GAA CTG GCT CCT TCC GGG ACT GGA GTG TCC CGA GAG GCC    1839
Gln Arg Asp Glu Leu Ala Pro Ser Gly Thr Gly Val Ser Arg Glu Ala
        570                 575                 580

TTG TCA GGT CTG CTG ATC ATG GGA GCT GGA GGA GGC TCT CTC ATT GTC    1887
Leu Ser Gly Leu Leu Ile Met Gly Ala Gly Gly Gly Ser Leu Ile Val
585                 590                 595                 600

CTA TCC TTG CTG CTT CTG CGC AAG AAG AAA CCC TAT GGG ACT ATC AGC    1935
Leu Ser Leu Leu Leu Leu Arg Lys Lys Lys Pro Tyr Gly Thr Ile Ser
                605                 610                 615

CAT GGA GTG GTG GAG GTG GAC CCC ATG CTG ACC CTG GAG GAG CAG CAG    1983
His Gly Val Val Glu Val Asp Pro Met Leu Thr Leu Glu Glu Gln Gln
                620                 625                 630
```

FIG.10D

```
CTC CGG GAA CTT CAG AGG CAT GGC TAT GAG AAC CCC ACC TAC CGC TTC        2031
Leu Arg Glu Leu Gln Arg His Gly Tyr Glu Asn Pro Thr Tyr Arg Phe
        635                 640                 645

CTG GAA GAA CGA CCT TGACCCCTAC CCTAGCTGCC TTCAGCTGAG CCCTACTGCCC       2087
Leu Glu Glu Arg Pro
    650

TTCTTCCGGC CCCCCAAACC CAACTCCCAG CTTCCGGTGG GGGAGGGAGA TCTTGACAAA      2147

TTCATTCTTG TTTCCCCTTC CTAGTTCCAA ATTCCACACC CTTAGAAATC CCCAGCTCCT      2207

GTCCCACAAG GGACCTCTTC ACCTTAATTT ATTTTACGTT AATTTATTGC TCCTTAAGGT      2267

GACCTGGGTC CCAGGTATGT ATGTCACTCC CTGGAATTCA CCATCCCACG TTTCTTCACT      2327

AACATCCCAA TAAACTCCTC TTTCCCTCCG GC                                    2359
```

FIG.10E

```
APLP   21 LLLPLSLLLLRAQLAVGNLAVGSPSAAEAPGSAQVAGLCGRLTLHRDLRT 70
          :| .|.||||  |.:.. .|.|....:|:   : .:|:| :||||.:|.::..
APP     1 MLPGLALLLL.AAWTARALEVPTDGNAGLLAEPQIAMFCGRLNMHMNVQN 49

71 GRWEPDPQRSRRCLLDPQRVLEYCRQMYPELHIARVEQAAQAIPMERWCG 120
          |:|:.||   .: |:  ...: :|:||.::||||:|..|  :|.|:::::||
       50 GKWDSDPSGTKTCIDTKEGILQYCQEVYPELQITNVVEANQPVTIQNWCK 99

121 GTRSGRCAHPHHEVVPFHCLPGEFVSEALLVPEGCRFLHQERMDQCESST 170
          .|.. .|||   |:|::||.||||||:||||: |:||||||||| ||.
      100 RCRKQCKTHPHF.VIPYRCLVGEFVSDALLVPDKCKFLHQERMDVCETHL 148

171 RRHQEAQEACSSQGLILHCSGMLLPCGSDRFRGVEYVCCPPPATPN...PS 218
          ::|  |.|.||..:  ||: ||||||| |:|||||:|||| :....: .|
      149 HWHTVAKETCSEKSTNLHDYGMLLPCGIDKFRGVEFVCCPLAEESDNVDS 198

219 GMAAGDPSTRSWPLGGR..AEGGED.......EEEVESFPQPVDDYFVEP 259
          : |.:|.|. .|. ::   |:|:||      ||||......|  :.
      199 ADAEEDDSDVWWGGADTDYADGSEDKVVEVAEEEEVAEVEEEEADDDEDD 248

260 PQAEEEEEEEEEERAPPPSSHTPVM.............VSRVTPTPRPT.D 295
          .:::| |||.||. ..:..:|. :            | ||..|: .| |
      249 EDGDEVEEEAEEPYEEATERTTSIATTTTTTTESVEEVVRVPTTAASTPD 298

296 GVDVYFGMPGEIGEHEGFLRAKMDLEERRMRQINEVMREWAMADSQSKNL 345
          :|| |::  ||: .||. | :|| ||..:.  .:.:|||||. |:..|.|||
      299 AVDKYLETPGDENEHAHFQKAKERLEAKHRERMSQVMREWEEAERQAKNL 348

346 PKADRQALNEHFQSILQTLEEQVSGERQRLVETHATRVIALINDQRRAAL 395
          ||||:..|: :|||. :::.||::...|||.||||| .|| |:::||.|| ||
      349 PKADKKAVIQHFQEKVESLEQEAANERQQLVETHMARVEAMLNDRRRLAL 398

396 EGFLAALQGDPPQAERVLMALRRYLRAEQKEQRHTLRHYQHVAAVDPEKA 445
          |.:::|||: ||.: :|:  |::|:||||:..|||:::|| |||.||
      399 ENYITALQAVPPRPRHVFNMLKKYVRAEQKDRQHTLKHFEHVRMVDPKKA 448

446 QQMRFQVQTHLQVIEERMNQSLGLLDQNPHLAQELRPQIQELLLAEHLGP 495
          .|:| || |||.|| ||||||||:|| . | :|:|:...:::||| |: .
      449 AQIRSQVMTHLRVIYERMNQSLSLLYNVPAVAEEIQDEVDELLQKEQNYS 498
```

FIG.11A

```
496 SELDASVPGSS..SEDKGSLQPPESKDDPPVTLPKGSTD......QESSS 537
    .::  |.: :..  |  :::.| |. ......|.| ....:      |.. |
499 DDVLANMISEPRISYGNDALMPSLTETKTTVELLPVNGEFSLDDLQPWHS 548

538 SGREKLTPLEQYE.QKVNA..SAPRGFPFHSS....DIQRDELA...... 574
    | :.::.: .: | :.|:| .|.||:. ..:    :|. :|:.
549 FGADSVPANTENEVEPVDARPAADRGLTTRPGSGLTNIKTEEISEVKMDA 598

575 ..................PSGTGVSREALSGLLIMGAGGGSLIVLSLLLL 606
                  :::.| ..::|: ||:: |.. ..:||:.|::|
599 EFRHDSGYEVHHQKLVFFAEDVGSNKGAIIGLMVGGVVIATVIVITLVML 648

607 RKKKPYGTISHGVVEVDPMLTLEEQQLRELQRHGYENPTYRFLEERP 653
    |||.|..| |||||||: :| ||.:|..:|.:||||||:|:|:..
649 .KKKQYTSIHHGVVEVDAAVTPEERHLSKMQQNGYENPTYKFFEQMQ 694
```

FIG. 11B extracellular domain I

```
                  .. |  |||.........   .| . .|.| | | .. ..
APLP   21   ILIpL  sLLLLrAqloVgnLoVgspsAAeoPgsoQvAgLC  G RLtIHrdIrt
APP     1   MLpgL  oLLLL AoWtorALeVptdgnAgIIoePQIAmfC  G RLnmHnmvqn
APPL    1   McooLrrnLLLr sIWvVIAigtoqvqAAssPrwPQIAvLCeoGqiyqpqyIsee
                                                  ^

|.| |..   .|. | . . ||  ||.. |....... .. ||
APLP   71   GRWepDPq   rs rrCLIDpqrvLe  YCrqmYPELhIorVeqAoQoipmerWCg
APP    50   GkWdsDPS  gT kTCi DtKegiIqYCqevYPELqITNVVEAnQpvtIqnWCk
APPL   55   GRWvtDISkktTgpTCLrD KmdLd YCkkoYPnrdITNiVEsshyqkIggWCr
                                 ^            ^              ^

.. ..     | . |..|| |.|.|.|||||..| |.|..... |. ..
APLP  122   gtRsgrCA  hp hHeV  vPFhCLpGEFVSeALLVPEGCrFLHQERMDqCEsst
APP   100   rGRk qCk  th pHfV  iPyRCLvGEFVSDALLVPdkCkFLHQERMDvCEthI
APPL  108   qGoIn oAkckgsHrwikPFRCL GpFqSDALLVPEGCIFdHihnosrCwpfv
                                   _____    ^        ^

...  ....|... . .|||||||.. |.|||.||||
APLP  172   RrHQeAqEACSsqGIiLHgsGMLLPCGsDrFRGVEyVCCP
APP   148   hWHtvAkEtCSEkstnLHdyGMLLPCGIDkFRGVEFVCCP
APPL  159   RWnQtgooACqErGmgmrtfoMLLPCGIsvFsGVEFVCCP
                  ^           _____  ^   ^^
``` extracellular domain II

```
                  .. ||. ..    || |  .. | ..| |||  .... .|| .. |
APLP  316   AKmdLEErrmrqineVMREW  omAdsQsKNL  PKA   DrQAIneHFQsiIQtL
APP   318   AKeRLEokHRErmsqVMREW  eEAerQoKNL  PKA   DKkAviqHFQekVesL
AAPL  413   sqkRLEEsHREkvtrVMkdWsdIEekyQdmrLodPKAoqsfKQrmtorFQtsVQoL

|..  |...|...| || | .|...| |.. .  ||. || ..| | ...
APLP  365   EEqvsgERQrLVETHotRViAIINDqRRoALEgfIoALQgdPPqAerVImoLrrYL
APP   368   EqEoonERQQLVETHmoRVeAmINDRRRIALEnYitALQovPPrprHVfnmLkKYv
APPL  470   EEEgnoEkhQLoomHqqRVIAhINqRkReAmtcYtqALteqPPnAhHVekcLqKIL

||..|...|.| |. | . ..|   ..|.. | ...| .| ...|||..|
APLP  421   RAEQKeqrHTLrHYqH VooVDP  EKAqQmRfQVqTHLqVIeERMNQSLgLL
APP   424   RAEQKDRqHTLkHfeH VrmVDP  kKAAQiRsQVmTHLrVIyERMNQSLsLL
APPL  523   RAIhKDRoHoLoHYrHIInsggPggIEoAAseRprtIerLidIdrovNQSmtmL
                                                            ===
```

FIG.12A cytoplasmic domain

```
                  .........  .|..|||...|    .    ||... ..| .||||||||...|...
APLP      609  KKKpYGTIS HGVVEVDPMLT     I      EEqqLrelQrHGYENPTYrFLEerp*
APP       649  KKKQYtSIH HGVVEVDaaVT     P      EERHLsKMQqNGYENPTYKFFEQMQn*
APPL      834  KwRtsrSpHaqGfiEVDqnVTthhPivrEEkivpnMQiNGYENPTYKYFEvke*
testis    145  rKRQYGTIS HGiVEVDPMLT     P      EERHLnKMQnHGYENPTYKYLEQMQi*
```

FIG.12B

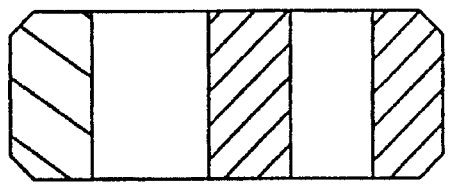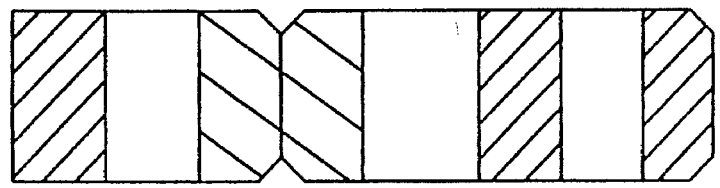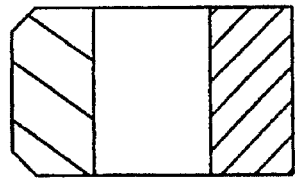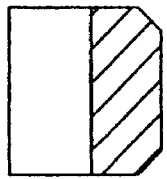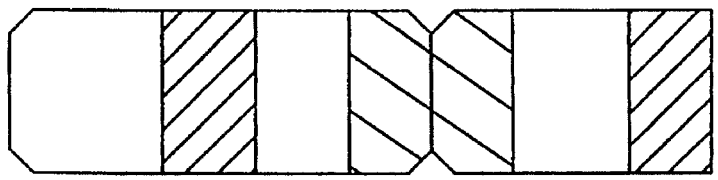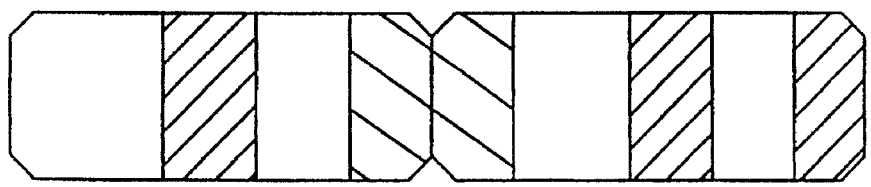
FIG. 16

```
APLP2    1   MAATGTAARAATGRLLLLLLVGLTAPAAALAGYIEALAAAAGTGFAVAEP  50
              . | ||||.::||.| .:         :...|.: :|||
APP      1   ..........MLPGLALLLLAAWTARALEV........PTDGNAGLLAEP  32

51   QIAMFCCKLNMHVNIQTGKWEPDPTGKSCFRTKEEVLQYCQEMYPELQI  100
             ||||||:||||:|:|.|||:.||.|||.|: |||::|||||||:|||||||
        33   QIAMFCGRLNMHMNVQNGKWDSDPSGTKTCIDTKEGILQYCQEVYPELQI  82

101   TNVVEANQRVSIDNWCRRDKKQCK...SRFVTPFKCLVGEFVSDVLLVPEK  148
             |||:||||.|.|:|||:|:::|||   .:||.|:::||||||||.||||:|
        83   TNVVEANQPVTIQNWCKRGRKQCKTHPHFVIPYRCLVGEFVSDALLVPDK  132

149   CRFFHKERMEVCENHQHWHTVVKEACLTQGMTLYSYGMLLPCGVDQFHGT  198
             |:|:|.|||:|||.| |||||.||.|  .:.|..|||||||||:|.|:|.
       133   CKFLHQERMDVCETHLHWHTVAKETCSEKSTNLHDYGMLLPCGIDKFRGV  182

199   EYVCCPQTKDYWSVSKEEEEEEDEE...EEEEEDEEEDYDVYKSEFPTEA  245
             |:||||  ..: .|....:||:|.:   :::...| .::  :  |.::|.
       183   EFVCCPLAEESDNVDSADAEEDDSDVWWGGADTDYADGSEDKVVEVAEEE  232

246   DLEDFTEAAVDEDDEDEEEGEEVVEDRDYYYDTFKGDDYNEENPTEPGSD  295
             :::...|...|  ||||:|:|:||  |: :   |:.     ..|..|. :..
       233   EVAEVEEEEAD.DDEDDEDGDEVEEEAEEPYEE......ATERTTSIATT  275

296   GTMSDKEITHDVKVPPTPLPTND.VDVYFETSADDNEHARFQKAEKEQLI  344
              .|  .......:. |:||.|: .| ||  |:||.:|:||||:||||  ||.|
       276   TTTTTESVEEVVRVPTTAASTPDAVDKYLETPGDENEHAHFQKA.KERLE  324

345   ERHRNRMDRVKKEWEEAELQAKNLPKAERQTLIQHFQAMVKALEKAEAAS  394
             .:||:||..|..:||||||| |||||||||:|:...|||||..|..||.|||.
       325   AKHRERMSQVMREWEEAERQAKNLPKADKKAVIQHFQEKVESLEQ.EAAN  373

395   EKQQLVETHLARVEAMLND.RRMALENYLAALQRSDPPRPHRILQPLRRY  443
             |:|||||||:||||||||| ||:||||:... |||:::.. |::|
       374   ERQQLVETHMARVEAMLNDRRRLALENYITALQ.AVPPRPRHVFNMLKKY  422

444   VRAENKDRLHTIRHYQHVLAVDPEKAAQMKSQVMTHLHVIEERRNQSLSL  493
             ||||.||| ||::|:::|| |||.|||||::||||||||:|| ||.||||||
       423   VRAEQKDRQHTLKHFEHVRMVDPKKAAQIRSQVMTHLRVIYERMNQSLSL  472
```

FIG.17A

```
494 LYKDPYVARI..QENDELLQAER.......ADM..........DQFTASI 524
    ||. | ||   :| |||||| |.       |:|         |.: :|:
473 LYNVPAVAEEIQDEVDELLQKEQNYSDDVLANMISEPRISYGNDALMPSL 522

525 SETPVDVRVSSEESE.EIPPFHPFHPFPALPENEDTQPELYHPMKKGSGV 573
    .||...| : . ::|  .:.. ::|:|.|.| .  .:|: |:
523 TETKTTVELLPVNGEFSLDDLQPWHSFGADSVPANTENEV.......... 562

574 GEQDGGLIGAEEKVINSKNKVDENMVIDETLDKEMIFNAERVGGLE.ERE 622
    |. ::  :|:    :........ .|: ..|. : .|  :  :|.|  .::
563 .EPVDARPAADRGLTTRPGSGLTNIKTEEISEVKMDAEFRHDSGYEVHHQ 611
                                              # #
623 SVGPLREDFSLSSSASIGLLVIAVAIATVIVISLVMLRKRQVCTISHGIV 672
    .:. : ||.:  ..:| |||:|  :|.||||||||.||||:|: ..| ||:|
612 KLVFFAEDVGSNKGAIIGLMVGGVVIATVIVITLVMLKKKQYTSIHHGVV 661
     ~  .        .o
673 EVDPMLTPEERHLNKMQNHGYEMPTYKTLEQNQI* 706
    |||: :||||||||.|||.:|||||||| :||||
662 EVDAAVTPEERHLSKMQQNGYENPTYKFFEQMQN* 695
```

FIG. 17B

```
APP695          ..........  M-....P-L-  LLLL-AWTA-  A--V......  ..---G-A--
APLP2           MAATG-AAR-  --....-L-   LLLLVGLTA-  AAALA----A  LA-A-G---A
APLP1           MGPTS-AAR-  ------P-L-  LLL-LSL---  -A-LA----A  VG-P--.A-A

APP695          LAEPQIAMFC  GRLNMHVNVQ  -GKWDSDP-G  TK-CI-TKEG  ILQYCQEVYP
APLP2           VAEPQIAMFC  GKLNMHMNIQ  TGKWEPDP-G  TK-CF-TKEE  VLQYCQEMYP
APLP1           -G-AQVA-LC  GRL-LH-DL-  TGRWEPDP--  SR-CL---Q-  VLEYC-QMYP

APP695          ELQITNVVEA  NQPV-IQNWC  KRDRK.QCK-  --HFVIPYRC  LVGEFVSDAL
APLP2           ELQITNVMEA  NQ-V-IDNWC  RRGKK.QCK.  .-RFV-PFKC  LVGEFVSD-L
APLP1           ELHI--V-QA  -QAI-ME-WC  ---R---C--  --H-VVPF-C  LPGEFVSEAL

APP695          LVPDKCKFLH  QERMDVCE-H  -HWHTVAKE-  CS---S--LHD  YGMLLPCGDD
APLP2           LVPEKCRFFH  -ERMEVCE-H  -HWHTV-KEA  C--QG--L-S  YGMLLPCGVD
APLP1           LVPEGCRFLH  QERMD-CE--  -RRH--A-EA  CSSQG--LHG  -GMLLPCG-D

APP695          KFRGVEFVCC  P-A-E-D-V-  -AD-EEDD-D  ---GG-D-D-  -DG-E----E
APLP2           -FHG-EYVCC  P----D----VS  --E-EEED-E  ...EE-EEDE  EED-D----E
APLP1           RFRGVEYVCC  P-P---N--G  -A--D-----  ---GG--EGG  ED........

APP695          -A-EEEV-E-  -E---D.DDE  DDEDGDEVEE  E-E--YEE..  .....--ER-T
APLP2           -P-E-DLEDF  -E---D-DDE  DEEEGEEV-E  D-D--YD---  -----EE-PT
APLP1           ...EEEVE-F  -Q---D---E  --Q--EE-EE  E.........  .....EERA-

APP695          --A-TTT---  --V--VVRVP  -TA--T-DAV  D-YLETPGDE  NEHAHFQKA.
APLP2           -PGS--T---  --I---VKVP  PTP-PT-D.V  DVYFET-ADD  NEHARFQKA-
APLP1           -P-S-T---.  .....V-RV-  PTP-PT.DGV  DVYFG-PGE-  -EH--F-RA.

APP695          KE-LE-KHRE  RM-QVMREWE  EAE-QAKNLP  KADK-AVIQH  FQ--VE-LEQ
APLP2           KEQL-ERHRN  RMD-V-KEWE  EAE-QAKNLP  KAERQ-LIQH  FQ-MV--LE-
APLP1           K-DLEERR--  -INEVMREW-  -AD-Q-KNLP  KADRQAL-EH  FQ-ILQ-LEE

APP695          .EAA-ERQQL  VETHMARVEA  MLND-RRLAL  ENYI-ALQ.A  -PPRP--VF-
APLP2           -EAASE-QQL  VETHLARVEA  MLND.RRMAL  ENYLAALQ-S  DPPRP-RIL-
APLP1           .Q--GERQ-L  VETH--RV-A  LIND-RR-AL  E-FLAALQ.G  DPP-A-RVL-

APP695          -LKKYVRAEQ  KDR-HTLKHF  EHV--VDP-K  AAQIRSQVMT  HLRVI-ERMN
APLP2           PLRRYVRAE-  KDR-HTIRHY  QHV-AVDPEK  AAQMKSQVMT  HLHVIEER-N
APLP1           ALRRYLRAEQ  KE--HTLRHY  QHV-AVDPEK  A-QMR-QV-T  HL-VIEERMN
```

FIG. 18A

```
APP695    QSLSLLY--P  -VAEEI DE-  DELLQ-E---  -----ANM--  --------D-
APLP2     QSLSLLY-DP  -VA--..QE-  DELLQAER..  .....ADM..  ........D-
APLP1     QSLGLL--NP  -LAQEL -Q-  QELL-AEH..  ..........  ..........

APP695    L-PSL-ET--  -V-L---NGE  -SL--LQPWH  -F-A-----N  TE-EV.....
APLP2     F-ASISET--  -V-VSS-ESE  .-I-PFHPFH  PFPA-----D  TQ-EL-----
APLP1     ..---SE---  -V--SS-E--  -SL-P----D  -PP-------  T--E......

APP695    ......E--D  A--AA---L-  ----SG--NI  --EE--E-KM  -AE--H-SG-
APLP2     -----  E--G  G--GA---V-  -S-----ENM  --DE--D--M  --NA-R-GGL
APLP1     ..........  ..........  .S--SG-E--  ---E--E-K-  -A-A-R---F

APP695    ...E--HQ-L  --F-ED-G--  -GA-IGLMV-  GV-IATVIVI  -LVMLKKKQ.
APLP2     ...E.ERE-V  G-L-ED-S-S  -SA-IGLLVI  AVAIATVIVI  SLVMLRKRQ.
APLP1     ---D-QRD-L  A..--G-G-S  --A--GLLIM  G-G-G-LIVL  SLLLLRKK--

APP695    Y--I-HGVVE  VDA-VTPEER  HL-KMQ-NGY  ENPTYKFFEQ  MQ-*
APLP2     --TISHGIVE  VDPMLTPEER  HL-KMQ-HGY  ENPTYK-LEQ  MQ-*
APLP1     Y-TISHGVVE  VDPMLT-EE-  QL--LQ-HGY  ENPTY-FLEE  --*
```

FIG.18B

METHODS FOR MODULATING TRANSCRIPTION FROM THE AMYLOID β-PROTEIN PRECURSOR (APP) PROMOTER

Part of the work performed during the development of this invention utilized U.S. Government Funds under NIH grants AG11899, NS/AG30428 and CA42567. The government may have certain rights to this invention.

FIELD OF THE INVENTION

The invention relates to methods for modulating transcription from the amyloid β-protein precursor (APP) promoter.

BACKGROUND OF THE INVENTION

The amyloid β-protein precursor (APP) is a member of a highly conserved family of integral membrane glycoproteins, which currently includes APP and two APP-like proteins (APLP), APLP1 and APLP2 (Wasco, W. et al., Genomics 15:237–239 (1993); Wasco, W. et al., Nat. Genet. 5:95–100 (1993)). APP-like proteins have also been identified in mouse (Wasco, W. et al., Proc. Natl. Acad. Sci. U.S.A. 89:10758–10762 (1992); Slunt, H. et al., J. Biol. Chem. 269:2637–2644 (1994)), Drosophila (Rosen, D. et al., Proc. Natl. Acad. Sci. U.S.A. 86:2478–2482 (1989)), and C. elegans (Daigle, I. et al., Proc. Natl. Acad. Sci. U.S.A. 90:12045–12049 (1993)). However, only APP gives rise to the 4 kDa Aβ peptide that aggregates in senile plaques and cerebral blood vessel deposits in the brains of patients with Alzheimer's disease (Masters, C. L. et al., EMBO J. 4:2757–2763 (1985); Glenner, G. G. et al., Biochem. Biophys. Res. Commun. 120:885–890 (1984)). The accumulation of the Aβ peptide in amyloid plaques occurs in the brains of normal elderly individuals, to some extent, but is greatly enhanced in patients with Alzheimer's disease and Down's syndrome (Masters, C. L. et al., Proc. Natl. Acad. Sci. U.S.A. 82:4245–4249 (1985)). The presence of a third copy of the APP gene on chromosome 21 in Down's syndrome patients and the subsequent increased levels of APP mRNA (Tanzi, R. E. et al., Science 235:880–884 (1987); Rumble, B. et al., New Engl. J. Med. 320:1446–1452 (1989)) suggest that overexpression of the APP gene most likely leads to amyloid deposition in these individuals. Altered regulation of APP transcription could conceivably lead to a similar situation in localized areas of brains of Alzheimer's disease patients. Experiments with transgenic mice showed that APP overexpression indeed leads to amyloid deposition (Quon et al., Nature 352:239 (1991); Wirac et al., Science 252:323 (1991)).

Studies of the promoter region of the APP gene indicate that it lacks typical TATA and CAAT boxes and has multiple transcriptional start sites, characteristic of housekeeping genes (Salbaum, J. M. et al., EMBO J. 7:2807–2813 (1988)). It has been reported that one or more elements located between position −94 and −35 are responsible for an 8-fold increase in gene expression in HeLa cells (Pollwein, P. et al., Nucleic. Acids. Res. 20:63–68 (1992)). Studies of the mouse APP promoter have shown that two positive regulatory elements are located between positions −100 and −37, and that one of these elements binds the mouse Sp1 factor (Izumi, R. et al., Gene 112:189–195 (1992)). A "combined" element, in which the AP-4 site is followed by an overlapping AP-1 site (AP-1/AP-4 site) is situated approximately at position −45 and is completely conserved in the human, rat and mouse promoters (Izumi, R. et al., Gene 112:189–195 (1992); Chernak, J. M., Gene 133:255–260 (1993)). The deletion of the region containing the AP-1/AP-4 site in the rat APP promoter causes a 30 % decrease in transcriptional activity in PC-12 cells (Hoffman, P. W. et al., Biochem. Biophys. Res. Commun. 201:610–617 (1994)). Interestingly, it has been shown that APP mRNA levels change dramatically during differentiation of embryonic P19 cells induced with retinoic acid (Fukuchi, K. et al., J. Neurochem. 58:1863–1873 (1992)).

The presence of an unidentified factor interacting with the AP-1/AP-4 site of the APP gene has been reported in a variety of systems. In HeLa cells, it has been demonstrated that the Sp1 factor interacts with an upstream GC-rich region and competes for binding with a factor interacting with the AP-1/AP-4 site (Pollwein, P. et al., Nucleic. Acids. Res. 20:63–68 (1992); Pollwein, P., Biochem. Biophys. Res. Commun. 190:637–647 (1993)). The binding of an unknown factor to the region containing the conserved AP-1/AP-4 site in the rat APP promoter has been reported to occur in PC-11 cells and in rat brain (Hoffman, P. W. et al., Biochem. Biophys. Res. Commun. 201:610–617 (1994)). Finally, Quitshke et al. used a DNA fragment lacking the upstream GC-rich region and found that an unidentified factor binds to the AP-1/AP-4 site of the APP promoter in Y79 cells (Quitschke, W. W. et al., J. Biol. Chem. 267:17362–17368 (1992)). This factor did not appear to be related to the known AP-1 or AP-4 transcriptional factors. However, the identity of the factor(s) which binds to the AP-1/AP-4 site of the APP promoter has not yet appeared in the literature. The identification of factors involved in transcriptional regulation of the APP gene would provide critical clues regarding the events leading to the formation of amyloid deposits.

SUMMARY OF THE INVENTION

The invention provides methods for modulating transcription from the amyloid β-protein precursor (APP) promoter. The upstream stimulatory factor (USF) has been identified as the nuclear factor that specifically binds the AP-1/AP-4 site within the APP promoter. The inventors have discovered that, not only does USF bind to the APP promoter, but it also activate transcription. Thus, the invention provides methods for activating transcription from the APP promoter. The method involves activating transcription by binding the APP promoter with either native or recombinantly produced USF.

The invention also provides methods for detecting transcription from the APP promoter. Detection methods can involve either expression of a "fusion" reporter protein or a primer extension analysis of mRNA transcripts. By the invention, the luciferase reporter protein is preferably used to detect transcription.

The invention further provides methods for down-regulating transcription from the APP promoter. The methods involve contacting the USF transcriptional activator with a USF binding compound capable of interfering with USF binding to the AP-1/AP-4 site in the APP promoter. By the invention, depending on the relative amounts of USF and the USF binding compound that are present, transcription from the APP promoter can be modulated as desired. Candidate USF binding compounds which may down-regulate transcription from the APP promoter include polyclonal and monoclonal anti-USF antibodies, nucleic acid fragments which contain an E-Box element, and members of the helix-loop-helix (HLH) transcription factor family. Preferred USF binding compounds are APP itself and the amyloid precursor like proteins, APLP1 and APLP2. Each of these compounds are capable of down-regulating transcription from the APP promoter.

The invention further provides a screening assay for determining which USF binding compounds are capable of down-regulating transcription from the APP promoter. The method involves transfecting a host cell with a recombinant construct containing the APP promoter operably linked to a gene encoding a reporter protein; transfecting the host cell with a recombinant construct capable of expressing the USF protein; measuring reporter protein expression activated by USF binding to the APP promoter; transfecting the host cell with a recombinant construct either containing or capable of expressing a candidate USF binding compound; and measuring if a decrease in reporter protein expression is caused by the USF binding compound interfering with USF binding to the APP promoter.

BRIEF DESCRIPTION OF THE FIGURES

FIG. 10. Nucleotide and amino acid sequence of the APLP1 cDNA. The composite nucleotide sequence (SEQ ID NO:15) and the predicted amino acid sequence (SEQ ID NO:16) of APLP1 is shown. The predicted membrane spanning region is underlined. The location of the primers that were used for the RACE procedures are indicated by arrowed lines over the nucleotide sequences. The location of the peptide sequence used for the production of antisera is double underlined. Predicted N-glycosylation sites are underlined with a squiggly line and a region surrounding a potential tyrosine phosphorylation site is underlined by dots. The polyadenylation signal is indicated by bold face type and the stop codon is shown by an asterisk.

FIG. 11. Comparison of the APLP1 (SEQ ID NO:17) and APP (SEQ ID NO:18) amino acid sequences. The UWGCG Bestfit analysis of the mouse APLP1 and human APP 695 (Chen, et al., *J. Biol. Chem.* 265:3116–3123 (1990)) is shown. Identities are indicated by a vertical line between the two amino acids. Similarities are indicated by a single or double dot. Gaps produced by the Bestfit alignment are shown by dots in the sequence. The βA4-protein sequence is underlined in the APP sequence. The identities are concentrated in three regions: APLP amino acids 21–211, 316–488, and 609–654.

FIG. 12. Domains of homology. Regions of the amino acid sequences of the mouse amyloid precursor like protein (APLP1) (SEQ ID NOS:19, 22, 25), the human amyloid precursor protein APP (SEQ ID NOS:20, 23, 26), the Drosophila amyloid precursor-like protein (APPL1) (SEQ ID NOS:21, 24, 27) and the rat testis cDNA (testis) (SEQ ID NO:28) are compared. Amino acids that are identical in all of the sequences in the domain are shown as capital letters in bold face type and are identified by the presence of a vertical line (|) above the sequences. Amino acids that are the same in more than one sequence are shown as capital letters and have a dot (°) over the sequences. Amino acids that are not identical to any others are shown as lower case letters. The conserved cysteines are identified by the presence of a carrot underneath the sequence. Spans of particularly conserved amino acids are underlined. An N-glycosylation signal is identified by a double underline. Stop codons are indicated by an asterisk and the amino acid numbers of the sequences are shown at the beginning of each line.

Figure 1A:
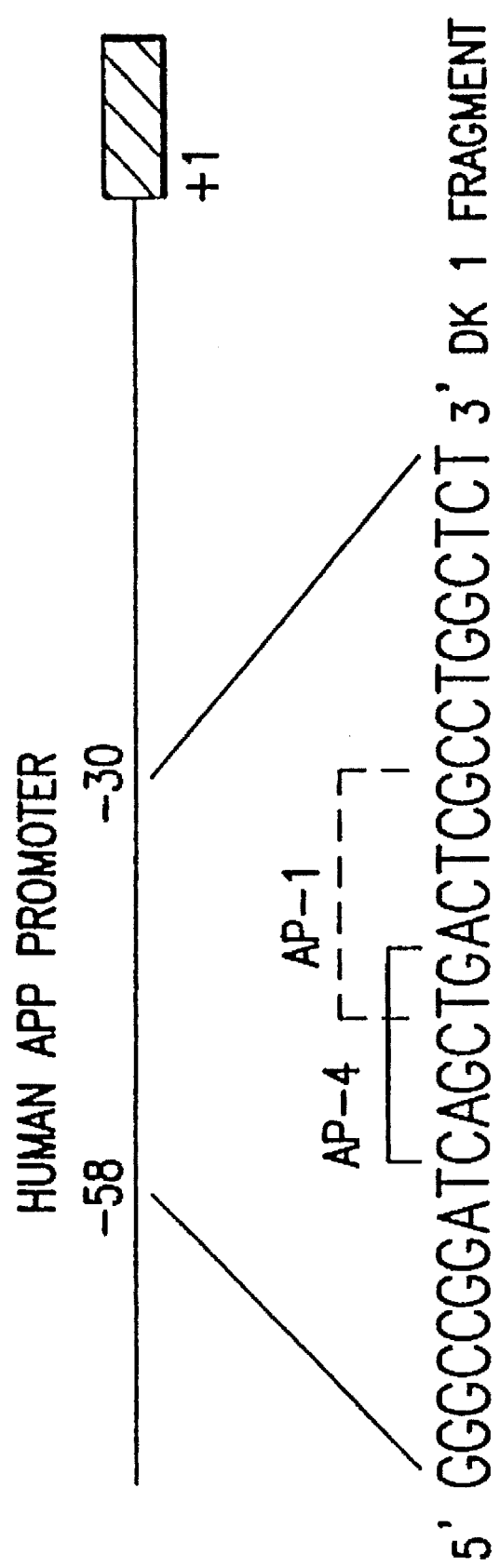
FIGS. 1A-B. DNA-protein interaction at the AP-1/AP-4 site. (A) Schematic representation of the APP proximal promoter region. The approximate position of the DK-1 fragment (SEQ ID NO:2) and the position of the overlapping AP-1/AP-4 sites within the DK-1 fragment are indicated. (B) EMSA performed with the DK-1 fragment using H4 nuclear extract. Competition was carried out with increasing amounts (0–50-fold) of unlabeled DNA fragments. Cold: DK-1 fragment.

(A) Mouse brain protein was probed with antiserum 301 or preimmune serum at a dilution of 1:100. The binding of antiserum 301 to the 65 and 33 kDa proteins is inhibited by the presence of increasing amounts of the peptide QQL-RELQRH (SEQ ID NO:1), used to immunize the rabbit. Preimmune serum with no peptide (lane 1); immune serum with no peptide (lane 2); immune serum preabsorbed with 5 ng/ml peptide (lane 3); immune serum preabsorbed with 50 ng/ml of peptide (lane 4); immune serum preabsorbed with 500 ng/ml of peptide (lane 5). Preabsorption with 500 ng of an irrelevant yeast β-tubulin peptide had no effect on the binding (lane 6).

(B) Neuroblastoma cell extracts probed with preimmune serum (lane 1) and 301 antiserum (lane 2). Both sera were used at a dilution of 1:100.

(C) Anti-peptide (QQLRELQRH) (SEQ ID NO:1) antiserum recognizes a β-galactosidase-APLP1 fusion protein. Western blots on bacterially produced proteins. Lanes 1–3 were stained with preimmune serum from rabbit 301. Lanes 4–6 were stained with immune serum. Lanes 1 and 4: induced (temperature sensitive induction and promoter) cells containing a plasmid with its β-galactosidase gene fused to an APLP1 cDNA fragment inappropriately oriented for production of an APLP1 epitope. Lanes 2 and 5: uninduced cells containing a plasmid with its β-galactosidase gene fused in frame to the APLP open reading frame. Lanes 3 and 6: same cells as in lanes 2 and 5 except induced. Induced cells were grown at 42° C. Uninduced cells were grown at 30° C. The arrowhead indicates a β-galactosidase-APLP1 fusion protein recognized by immune serum but not by preimmune serum. That protein is approximately 24 kDa larger than β-galactosidase alone, as predicted, due to the insertion of 222 additional residues of APLP1 open reading frame.

FIGS. 15A–E. Immunofluorescence staining of mouse neuroblastoma cells with antiserum 301. Cells were stained with antiserum 301 at a dilution of 1:10,000 as described in Materials and Methods. Panel (A) shows neuroblastoma cells stained with antiserum 301. Panel (B) shows a higher magnification of a cell stained with antiserum 301 where the reticular pattern is evident. This staining pattern is similar to that seen when an antibody to a known Golgi enzyme (mannosidase II) is used to stain the cells (C). The perinuclear staining is competed by the addition of the peptide that was used as the antigen (D), and is not seen in the presence of preimmune serum (E). The magnification in a,c,d and e is 720X and in b 950X.

FIG. 16. Mapping of the APLP1 locus using a somatic cell hybrid panel. All hybrids have been previously described (Brook et al., Hum. Genet. 7:65–72 (1991); Chartier-Harlin et al., Nature 353:884–846 (1991); and Geissler et al., Cell Mol. Genet. 17:197–214 (1991)). The portions of chromosome 19 retained in each human-rodent cell hybrid are illustrated, and the names of the representative cell lines are shown above. The presence (+) or absence (−) of APLP1 in each hybrid cell line is indicated.

FIG. 17. Comparison of APLP2 (SEQ ID NO:29) and APP (SEQ ID NO:30) amino acid sequences. An alignment of the human APLP2 amino acid sequence and the human APP695 (Kang et al., Nature 325:733–736 (1987)) was generated using the UWGCG GAP analysis. Gaps produced by the alignment are indicated by dots in the sequence. The location of the four PCR primers that were used to generate the SG190 probe are indicated by arrows above the amino acid sequence. Twelve conserved cysteines are indicated by carets (^) under the sequence and a zinc-binding motif is indicated by a double underline. A conserved acidic-rich region is located between APLP2 amino acids 216 and 278. An N-glycosylation signal is underlined, an alternatively spliced exon is overlined, predicted transmembrane regions are shown in italics, and a clathrin binding motif is indicated by bold face type. Potential phosphorylation sites are indicated by a # sign (protein kinase C), a sign (caseine kinase I and II) or a ° sign (tyrosine kinase) over the sequence. Stop codons are indicated by an asterisk.

FIG. 18. Alignment of the amino acid sequences of the members of the APP-gene family (SEQ ID NOS:31–33). The sequences of human APLP2, mouse APLP1 (Wasco et al., Proc. Natl. Acad. Sci. U.S.A. 89:10758–10762 (1992)) are presented as aligned by the UWGCG PILEUP program. Amino acids that are not identical or conservatively substituted are indicated by a dash. Gaps in the amino acid sequence that were created by the alignment are shown by dots. The predicted initiator methionine for each protein is shown and stop codons are indicated by an asterisk.

Figure 19A:
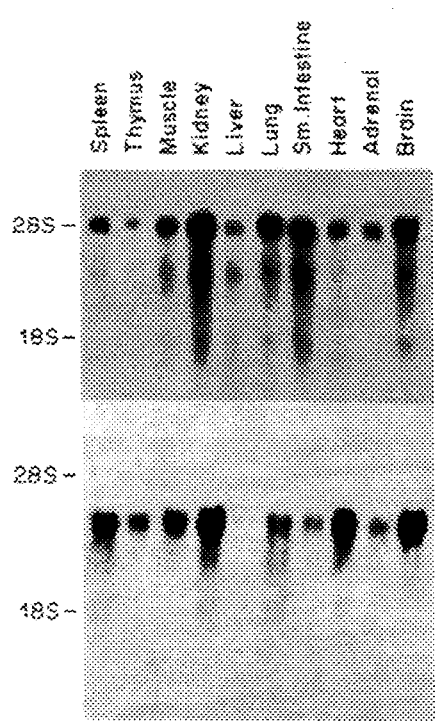
Figure 19B:
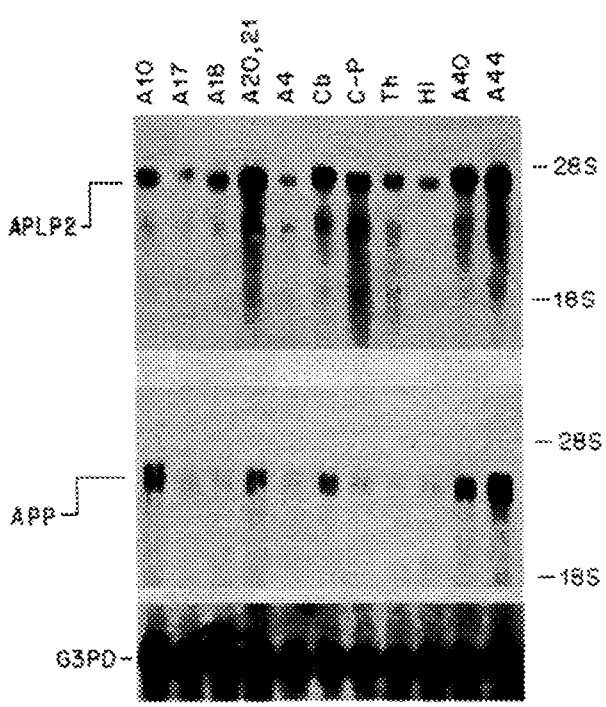

FIGS. 19A–B. Distribution of human APLP2 gene transcripts. RNA from fetal human tissues (A) or adult human brain (B) was isolated, fractionated, transferred to nylon membranes, and hybridized with radiolabeled probe as previously described (Tanzi et al., Science 235:880–884 (1987)). (A) Hybridization of a PCR fragment corresponding to APLP2 amino acids 327 to 490 (APLP2) or a 3' 1.1 kb EcoRI APP cDNA fragment (FB63) were hybridized to RNA (20 μg) from human 20–22 week aborted fetal tissue obtained midtrimester under protocols approved by the institutional review board at Brigham and Women's Hospital. (B) Hybridization of the APLP2 PRC fragment or FB63 to RNA (10 μg) from adult human brain subregions: A10, frontal cortex; A17, striate cortex; A18, extrastriate cortex, A20, 21 temporal association cortex; A4, motor cortex; thalamus-VPL, thalamus-ventral posterolateral nucleus; A40, posterior perisylvian cortex-supramarginal gyri; A44, anterior perisylvian cortex-opercular gyri. Shown beneath panel B is a control hybridization with a glyceraldehyde-3-phosphate dehydrogenase cDNA (G3PD). The two autoradiograms are from independent hydribizations to the same filter.

Figure 20:
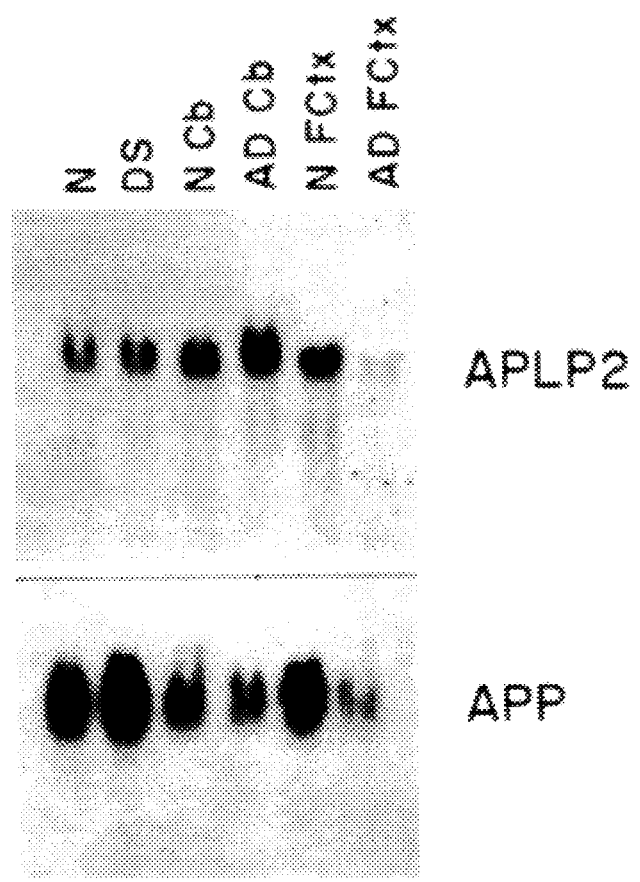

FIG. 20. Northern blot of APLP2 to total RNA from normal and Down syndrome brains, adult normal and ADA cerebellum and frontal cortex. A PCR generated fragment corresponding to APLP2 amino acid 327 to 490 and FB63 (APP) were hybridized to total RNA (25 μg) from 19-week normal (N) and Down syndrome (DS) brains, adult normal (N Cb) cerebellum, and adult normal (N FCtx) and AD (AD FCtx) frontal cortex. The two autoradiograms are from independent hybridizations to the same filter.

Figure 21A:
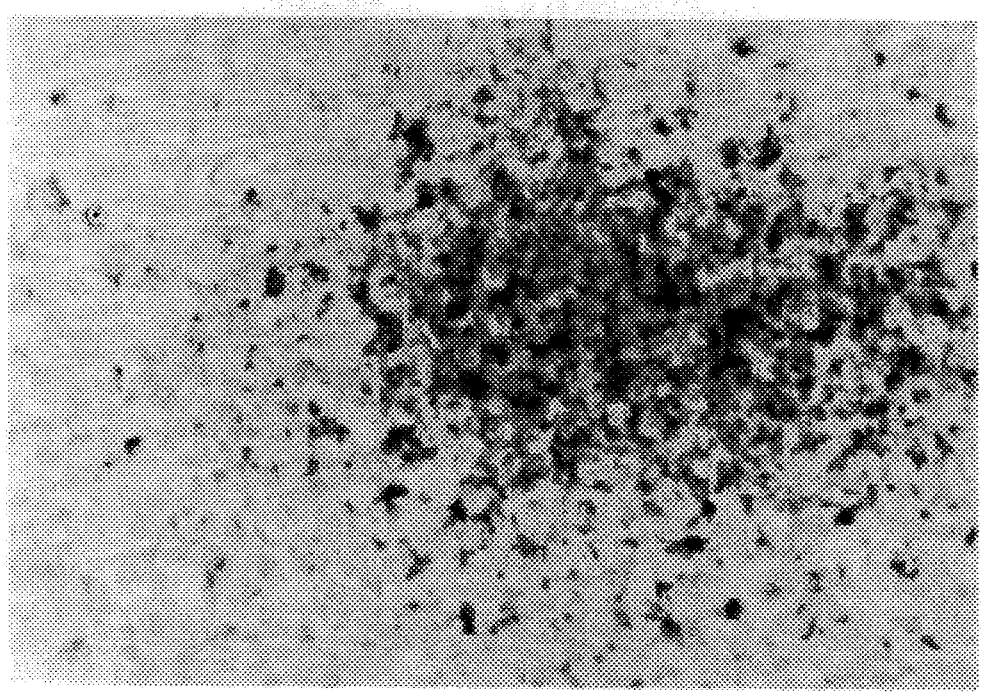
Figure 21B:
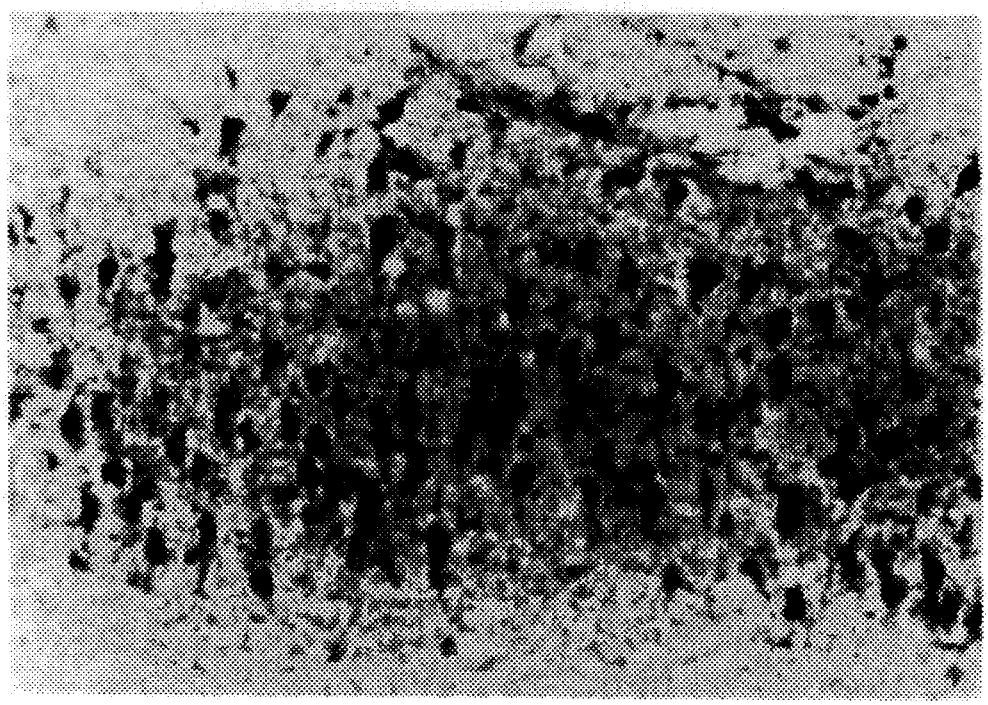

FIG. 21. Nonisotopic in situ localization of APLP2-oligonucleotide. A) In situ hybridization using a 45-mer specific for APLP2 (corresponding to amino acids 74–88 in FIG. 17 (SEQ ID NO:29) reveals staining of CA1 pyramidal neurons. The probe was end-labeled with biotin-21-dUTP using 3' terminal transferase and visualized by avidin-biotin-peroxidase reaction (Tanzi et al., Mol. Brain Res.:in press; Hyman et al., Mol. Brain Res.:in press; Wasco et al., Alzheimer's disease and related disorders 1992:selected communications (in press)). b) a negative control 45-mer corresponding to the other strand of the same region of APLP2 shows no significant staining. Magnification=16X.3.

DETAILED DESCRIPTION OF THE INVENTION

The present inventors recognized that the AP-1/AP-4 site in the amyloid β-protein precursor (APP) promoter contains a palindromic sequence which includes an E-box element. E-box sequences are binding sites for the helix-loop-helix (HLH) transcription factor family including myc and Myo-D, and are involved in the regulation of development and cell differentiation (Murre, C. et al., Cell 56:777–783 (1989); Tapscott, S. J. et al., Science 242:405–411 (1988)).

In an attempt to identify the factor that binds to the AP-1/AP-4 element, the present inventors investigated a candidate mammalian activator, upstream stimulatory factor (USF), which interacts with the adenovirus major late promoter and to elements in several cellular gene promoters, including those for the insulin gene (Read, M. L. et al., Biochem. J. 295:233–237 (1993)), the type I plasminogen activator inhibitor gene (Riccio, A. et al., Mol. Cell Biol. 12:1846–1855 (1992)) and the P53 tumor suppressor gene (Reisman, D. et al., Nucleic. Acids. Res. 21:345–350 (1993)).

The present inventors have discovered that USF binds specifically to the AP-1/AP-4 site in the APP promoter. Moreover, the inventors have discovered that USF is necessary to maintain elevated levels of APP mRNA and that recombinant USF elevates transcription levels from the APP promoter. This has been shown in a cell-free transcription system wherein exogenous USF was added to a construct containing the APP promoter and by transfecting a host cell containing the APP promoter with a construct encoding and capable of expressing USF. Thus, the present invention is directed to modulating transcription from the APP promoter by binding the promoter with either exogenously added or recombinantly produced USF. The method involves binding the AP-1/AP-4 site in the APP promoter with either native or rUSF whereby transcription from the promoter is activated.

Native and recombinant USF are readily available. Native USF can be obtained from H4 neuroglioma cells or HeLa cells by preparing nuclear extracts as described in Miner et al., J. Neurosci. Res. 33:10 (1992). Alternatively, cDNA encoding the 43 kDa form of USF has been cloned, sequenced and expressed in bacteria (Gregor et al. Genes. Dev. 4:1730 (1990)). It has been shown that the recombinantly expressed 43-kDa USF binds to its cognate DNA sequence in a manner indistinguishable from that of HeLa USF (Pognonec & Roeder, Molecular and Cellular Biology 11:5125 (1991)). It would be well within the ability of the skilled artisan to subclone the gene encoding USF into an appropriate DNA or RNA expression vector depending on the host cell to be transfected and the level of expression sought. For example, the present inventors have subcloned the USF gene into a retroviral vector expression system and transfected H4 neuroglioma cells with the resulting construct.

The control sequences, expression vectors, and transformation methods are dependent on the type of host cell used to express the USF gene. Generally, procaryotic, yeast, or mammalian cells are useful as hosts. Procaryots most frequently are represented by various strains of E. coli. However, other microbial strains may also be used, such as bacilli, for example Bacillus subtilis, various species of Pseudomonas, or other bacterial strains. In such procaryotic systems, plasmid or bacteriophage vectors which contain replication sites and control sequences derived from a species compatible with the host are used. A wide variety of vectors for many procaryotes are known (Maniatis et al., (1982) Molecular Cloning: A Laboratory Manual, Cold Spring Harbor Laboratory, Cold Spring Harbor, N.Y.; Sambrook et al., Molecular Cloning (1989) Molecular Cloning: A Laboratory Manual, 2nd Ed., Cold Spring Harbor Laboratory, Cold Spring Harbor, N.Y.; Methods of Enzymology Vol. 68, 100, 101, 152–155, Academic Press, Orlando (1979, 1983, 1987). Commonly used procaryotic control sequences include promoters for transcription initiation, optionally with an operator, along with ribosome binding site sequences, include such commonly used promoters as the beta-lactamase (penicillinase) and lactose (lac) promoter systems, the tryptophan (trp) promoter system and the lambda derived PL promoter and N-gene ribosome binding site, which has been made useful as a portable control cassette (U.S. Pat. No. 4,711,845). However, any available promoter system compatible with procaryotes can be used.

In addition to bacteria, eucaryotic microbes, such as yeast, may also be used as hosts for the expression of USF. Laboratory strains of Saccharomyces cerevisiae, Baker's yeast, are most used although a number of other strains are commonly available. Vectors employing the 2 micron origin of replication and, other plasmid vectors suitable for yeast expression are known (Maniatis et al., (1982) Molecular Cloning: A Laboratory Manual, Cold Spring Harbor Laboratory, Cold Spring Harbor, N.Y.; Sambrook et al., Molecular Cloning (1989) Molecular Cloning: A Laboratory Manual, 2nd Ed., Cold Spring Harbor Laboratory, Cold Spring Harbor, N.Y.; Methods of Enzymology, Vol. 68, 100, 101, 152–155, Academic Press, Orlando (1979, 1983, 1987); Pouwels et al., Cloning Vectors: A Laboratory Manual. Elsevier, Amsterdam (1987)). Control sequences for yeast vectors include promoters for the synthesis of glycolytic enzymes. Additional promoters known in the art include the promoter for 3-phosphoglycerate kinase and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization. It is also believed that terminator sequences are desirable at the 3' end of the coding sequences. Such terminators are found in the 3' untranslated region following the coding sequences in yeast derived genes. Many of the vectors illustrated contain control sequences derived from the enolase gene containing plasmid peno-46 or the LEU2 gene obtained from YEp13, however, any vector containing a yeast compatible promoter, origin of replication and other control sequences is suitable (Maniatis et al., (1982) Molecular Cloning: A Laboratory Manual, Cold Spring Harbor Laboratory, Cold Spring Harbor, N.Y.; Sambrook et al., Molecular Cloning (1989) Molecular Cloning: A Laboratory Manual, 2nd Ed., Cold Spring Harbor Laboratory, Cold Spring Harbor, N.Y.; Methods of Enzymology , Vol. 68, 100, 101, 152–155, Academic Press, Orlando (1979, 1983, 1987); Pouwels et al., Cloning Vectors: A Laboratory Manual. Elsevier, Amsterdam (1987)).

It is also possible to express the gene encoding USF in eucaryotic host cells from multicellular organisms (Freshly, R. I., Culture of Animal Cells: A Manual of Basic Technique, 2nd Ed., Alan R. Liss, New York (1987)). Useful host cell lines include murine myelomas N51, VERO, and HeT cells, and Chinese hamster ovary (CHO) cells. Expression vectors for such cells ordinarily include promoters and control sequences compatible with mammalian cells such as, for example, the commonly used early and late promoter from Simian Virus 40 (SV40), or other vital promoters such as those derived from polyoma, Adenovirus 2, bovine papilloma virus, or avian sarcoma viruses, or immunoglobulin promoters and heat shock promoters (Maniatis et al., (1982) *Molecular Cloning: A Laboratory Manual*, Cold Spring Harbor Laboratory, Cold Spring Harbor, N.Y.; Sambrook et al., *Molecular Cloning* (1989) *Molecular Cloning: A Laboratory Manual*, 2nd Ed., Cold Spring Harbor Laboratory, Cold Spring Harbor, N.Y.; Methods of Enzymology, Vol. 68, 100, 101, 152–155, Academic Press, Orlando (1979, 1983, 1987); Pouwels et al., Cloning Vectors: A Laboratory Manual. Elsevier, Amsterdam (1987)). General aspects of mammalian cell host system transformations have been described by Axel (U.S. Pat. No. 4,399,216). Origins of replication may be obtained, if needed, from viral sources. However, integration into the chromosome is a common mechanism for DNA replication in eucaryotes. Plant cells are now also available as hosts, and control sequences compatible with plant cells such as the nopaline synthase promoter and polyadenylation signal sequences are available (Pouwels et al., Cloning Vectors: A Laboratory Manual. Elsevier, Amsterdam (1987); Methods of Enzymology, Vol 118, Academic Press, Orlando (1986); Gelvin et al., Plant Molecular Biology Manual, Kluwer Academic Publishers, Dudrecht (1990)).

Depending on the host cell used, transformation is done using standard techniques. Such techniques include calcium treatment employing calcium chloride for procaryotes or other cells which contain substantial cell wall barriers; infecting with *Agrobacterium tumefaciens* for certain plant cells; calcium phosphate precipitation method for mammalian cells without cells walls; and, macroprojectile bombardment for many cells including plant cells.

The present inventors have shown that transcription of a reporter protein from an APP promoter present in H4 neuroglioma cells can be enhanced 5-fold by transfecting the cells with a retroviral expression vector capable of expressing USF. Thus, it will be recognized that a variety of expression vectors can be used for expressing the USF gene depending on what type of cells contain the APP promoter.

Delivery of the gene encoding USF to cells in humans for modulating APP expression can occur using one of the many known vector systems known in the art. Retroviral vectors can only integrate into the genome of dividing cells. Thus, these vectors provide a useful vehicle for the selective targeting of USF to dividing cells. Retroviral vectors offer further advantages as there are no limitations in host range and these vectors have already been used successfully to infect many different cell types (Cepko, C., "Lineage analysis and immortalization of neural cells vial retrovirus vectors", in *Neuromethods*, Vol. 16, 177–218, Clifton, N.J., The Humana Press, Inc. (1989); Gilboa, E., *BioEssays* 5(6):252–257 (1987); Friedmann, T., *Science* 244:1275–1281 (1989)). In general retroviral expression vectors that are effective for integrating genes into dividing cells are well known in the art (Breakfield et al, *Molec. Neuro. Biol.* 1:229 (1987); Breakefiled et al. *The New Biologist* 3:203 (1991); Huang et al., *Experimental Neurology* 115:303 (1992), WO93/03743 and WO90/09441. APP is expressed in all major tissues (Schmechel et al., *Alzheimer Dis. Assoc. Disord.* 2:96 (1988)). In the brain, APP is expressed primarily, but not exclusively, in neurons (Schmechel et al., *Alzheimer Dis. Assoc. Disord.* 2:96 (1988)). Expression vectors capable of infecting neurons are known and include those based on the Herpes Simplex Virus.

The APP promoter has been cloned and sequenced (Quitschke & Goldgaber, *The Journal of Biological Chemistry* 267:17362 (1992)). The inventors have discovered that USF will bind to DNA fragments containing the AP-1/AP-4 element located in the APP promoter. Example 1 of the specification shows that the sequence of the DK-1 fragment, which extends from –30 to –58 from the primary transcriptional site of the human APP promoter (Salbaum, J. M. et al., *EMBO J.* 7:2807–2813 (1988)) and contains the AP-1/AP-4 element (underlined):

5'GGGCCGGATCAGCTGACTCGCCTGGCTCT'3 (SEQ. ID. NO:2), is specifically bound by both native and rUSF.

Preferably, the APP promoter is operably linked to a nucleic acid sequence encoding either the APP protein or a heterologous polypeptide. Of course, the APP promoter is operably linked to the APP gene in the variety of cells which naturally express APP. In another preferred embodiment, the APP promoter is operably linked to a nucleic acid sequence encoding a reporter protein. Such "fusion" reporter proteins are well known in the art. A reporter gene encoding a reporter protein may be fused to the APP promoter or fragments thereof containing the AP-1/AP-4 element. The amount of reporter gene product produced is indicative of the relative activity of the promoter. Thus, the present invention is further directed methods for detecting transcription from the APP promoter.

One example of a suitable reporter protein is β-galactosidase. β-galactosidase is an enzyme encoded by the lac Z gene of *E. coli*. The presence of the lac Z gene product in a cell can be qualitatively determined in whole cells and can be quantitatively measured in cell-free extracts. Other reporter genes that can be used include: β-galactosidase (MacGregor et al., 1987, *Somatic Cell Mol. Genet.* 13:253–266); galactokinase (e.g., Rosenberg et al., 1983, *Science* 222:734–739; McKenney et al., 1981, in *Gene Amplification and Analysis* 2:383–415, Elsevier/North-Holland, New York); Murooka and Mitani, 1985, *J. Biotechnol.* 2:303–316; β-glucuronidase (e.g., Jefferson et al., 1986, *Proc. Natl. Acad. Sci. U.S.A.* 83:8447–8541); human growth hormone (e.g., Seldon et al., 1986, *Mol. Cell. Biol.* 6:3173–3179); chloramphenicol acetyltransferase (CAT) (e.g., Tsukada et al., 1987, *J. Biol. Chem.* 262: 8743–8747; Carbonell and Miller, 1987, *Appl. Environ. Microbiol.* 53: 1412–1417; Boulet et al., 1986, *Proc. Natl. Acad. Sci. U.S.A.* 83:3599–3603; Jameson et al., 1986, *Endocrinology* 119:2560–2567; Montminy et al., 1986, *Proc. Natl. Acad. Sci. U.S.A.* 83:6682–6686); Tn5 neomycin phosphotransferase (e.g., Kaulen et al., 1986, *EMBO J.* 5: 1–8; Simpson et al., 1985, *EMBO J.* 4:2723–2730) and firefly luciferase (e.g., Ow et al., 1987, *Proc. Natl. Acad. Sci. U.S.A.* 84:4870–4874, Ow et al., 1986, *Science* 234:856–859).

Quitschke et al. fused the APP promoter 5' and operably linked to the reporter gene chloramphenicol acetyltransferase (Quitschke et al., *The Journal of Biological Chemistry* 267(24):17362 (1992)). The present inventors have fused the APP promoter 5' and operably linked to the luciferase reporter gene. The luciferase reporter gene system is discussed in detail in U.S. Pat. No. 5,196,424.

An alternative method for detecting transcription from the APP promoter involves primer extension analysis of the resulting transcript. Primer extension analysis involves hybridizing a primer having a sequence complementary to a portion of the transcribed mRNA and performing primer extension. Preferably, the primer is detectably labelled. Primer extension analysis is well known in the art. The present inventors, for example, prepared an APP promoter-luciferase reporter gene construct by inserting a 2.9 EcoRI/BamHI APP promoter fragment (Salbaum et al., *EMBO J.* 7:2807 (1988)) into the SmaI site of the luciferase expression vector pxP2 (Nordeen, S. K., *Biotechniques* 6:454 (1988)). Cell-free in vitro transcription of the construct was performed according to the method of Dignam et al., *Nucleic Acids Res* 11:1475 (1983). Transcription from the construct was then detected by hybridizing a primer corresponding to part of the multiple cloning site between the APP promoter and the reporter gene. The primer had the following sequence: 5'-GCTCAGATCTCGAGCTCGGTAC-3' (SEQ. ID. NO:3).

There are a variety of compounds which bind USF. These include anti-USF polyclonal and monoclonal antibodies, nucleic acid fragments which contain E-Box sequences (CANNTG) and helix-loop-helix (HLH) transcription factors. The present inventors have discovered that certain USF binding compounds are capable of interfering with USF binding to the APP promoter thereby down-regulating transcription. By "down-regulating transcription from the APP promoter" is intended reducing transcription from the APP promoter relative to the transcription level attained in the absence of the USF binding compound. Thus, a further aspect of the present invention is directed to down-regulating transcription from the APP promoter using one or more USF binding compounds. The method involves contacting the USF transcription activator with a USF binding compound(s) capable of interfering with USF binding to the APP promoter. Depending on the relative amounts of USF and the USF binding compound that are present, transcription from the APP promoter can be modulated as desired. For example, the present inventors transfected host cells with the APP promoter-luciferase reporter gene construct discussed above. The cells were then transfected with an expression vector encoding the USF gene (pCMV-USF). This activated transcription from the APP promoter about 5-fold relative to the transcription level attained in the presence of a control plasmid not encoding the USF transcription activator. The cells were then transfected with an expression vector encoding one of the following USF binding compounds: APLP1, APLP2, and APP. The results showed that the presence of each member of the APP/APLP family decreases the level of USF activation of transcription from the APP promoter at least 50%.

As indicated, candidate USF binding compounds which may down-regulate transcription from the APP promoter include, but are not limited to, polyclonal and monoclonal anti-USF antibodies, nucleic acid fragments which contain E-Box sequences (CANNTG) and members of the helix-loop-helix (HLH) transcription factor family.

Polyclonal and monoclonal antibodies can be raised against USF according to conventional techniques. For example, USF antiserum can be prepared as described in Kaulen et al., *Mol. Cell. Biol.* 11:412 (1991). Using an electrophoretic mobility shift assay (EMSA), the present inventors have shown that USF antiserum causes a marked decrease in the amount of USF complex formation with the AP-1/AP-4 site in the APP promoter.

Nucleic acid fragments which contain an E-Box sequence can be any fragment containing the sequence CANNTG (or CANNUG if the fragment comprises RNA), where "N" is a nucleotide containing any of the four bases: Adenine, Guanine, thymidine (Uracil), or Cytosine. Preferably, "N" is a nucleotide containing either Cytosine or Guanine. For example, the core sequence of the AP-1/AP-4 site is CAGCTG. USF also binds the core sequence of the major late adenoviral promoter, CACGTG.

By the invention, exogenously added or recombinantly produced nucleic acid fragments containing an E-Box sequence down-regulate transcription from the APP promoter through competition for USF binding. For example, in competition assays, the present inventors have shown that the presence of a DNA fragment containing an E-Box sequence significantly decreases transcription from the APP promoter. Conversely, the presence of the same DNA fragment in which the E-Box sequence was replaced by a random sequence does not decrease transcription. Whether any given DNA fragment containing an E-Box sequence is capable of down-regulating transcription from the APP promoter can easily be determined empirically.

USF is a basic helix-loop-helix (HLH) protein, binding DNA through the basic region, and other HLH proteins through the HLH domain. The APP/APLP family of proteins contain a region homologous to an HLH domain, but the preceding region is only slightly basic. Other HLH proteins which display features similar to that of the APP/APLP family have been characterized and have been shown to bind to basic HLH proteins other than USF. For example, the protein called Id specifically represses transcriptional activation by the basic HLH myogenic factor, MyoD. It is these proteins which display features similar to that of the APP/APLP family (i.e., which modulate transcriptional activation by basic HLH proteins) that are candidate USF binding compounds. Such candidate proteins, or peptide fragments thereof, can be screened for the ability to down-regulate transcription from the APP promoter using the screening assay described below.

The present inventors have discovered that amyloid precursor-like proteins (APLP) and APP itself are capable of down-regulating transcription from the APP promoter by interfering with USF binding to the AP-1/AP4 site. By "amyloid precursor-like proteins" (APLP) is intended to include any amyloid precursor-like protein, from any species, including APLP1 and APLP2, especially from human brain, Alzheimer's disease human brain, or a synthetic APLP. The present APLP exhibits at least 40% identity at the amino acid level to APP and/or APLP1 and/or APLP2, more preferably at least 50% identity thereto, and contains an N-terminal cysteine-rich region consisting of at least 10 cysteines, more preferably consists of 12 cysteines. The term is also used in this invention to include any analog, homolog, mutant or derivative of a naturally occurring APLP. The term is also meant to include fragments having less than the naturally occurring number of amino acids, such as partial fragments of natural or synthetic APLP which retain the biological or immunological characteristics of the polypeptides specifically disclosed in this application. The term is also used to include any product which comprises the sequence of a naturally occurring APLP, or analog or homolog thereof, together with one or more flanking amino acids, which still have the same biological or immunological characteristics.

The term is also used to include any peptide which comprises the sequence of a naturally-occurring APLP or an analog thereof together with one or more flanking amino acids, which have the same biological (functional or structural) or immunological characteristics.

The APLP's suitable for use in the present invention can be administered exogenously or by expression using recombinant DNA techniques. Methods for isolating, cloning, and recombinantly expressing APLP's are discussed below.

As indicated, the present invention is further directed to a screening assay for identifying which USF binding compounds are capable of down-regulating transcription from the APP promoter. The method involves transfecting a host cell with a DNA or RNA construct containing the APP promoter operably linked to a gene encoding a reporter protein; transfecting the host cell with a DNA or RNA construct capable of expressing the USF protein; measuring reporter protein expression activated by USF binding to the APP promoter; transfecting the host cell with a DNA or RNA construct either containing or capable of expressing a USF binding compound; and measuring if a decrease in reporter protein expression is caused by the USF binding compound interfering with USF binding to the APP promoter.

Preferably, the gene encodes luciferase reporter protein, the DNA binding compound is an APLP, and the host cells are neurogliomas. More preferably, the APLP is APLP-1 or APLP-2 or fragments thereof capable of decreasing transcription. Techniques for measuring luciferase reporter protein levels are well known in the art (See, for example, U.S. Pat. No. 5,196,424). Techniques for measuring levels of other reporter proteins are also known in the art (See the reference cited above). Due to its simplicity, the screening method of the present invention is suitable for screening large numbers of USF binding compounds to determine which are capable of reducing transcription from the APP promoter.

A detailed description of methods for isolating, cloning, and expressing APLP proteins is provided below and in co-pending application no. 08/007,999, which is herein incorporated by reference.

Having established the amino acid sequence of both APLP1 and APLP2, a nucleotide probe can be constructed which is complementary to the DNA, or mRNA coding for APLP1 or APLP2 or a fragment thereof. This probe can be used as a diagnostic test to determine the presence of other APLPs.

The process for genetically engineering APLP1 and APLP2 sequences, is facilitated through the cloning of genetic sequences which are capable of encoding the peptide and through the expression of such genetic sequences. Genetic sequences which are capable of encoding the present APLP proteins are derived from a variety of sources. These sources include genomic DNA, cDNA, synthetic DNA, and combinations thereof. The preferred source of the genomic DNA or mRNA is brain or neuroblastoma cells. Post mortem RNA procedures can be followed to isolate the RNA. See Sajdel-Sulkowska et al., *J. Neurochem.* 40:670–680 (1983). The mRNA may then be used to obtain cDNA by techniques known to those skilled in the art. Probes may be synthesized based on the known amino acid sequence of the present APLP proteins (APLP1 and APLP2) by methods known in the art.

APLP mRNA can be isolated from any cell which produces or expresses APLP, and used to produce cDNA by means well known in the art (for example, see *Guide to Molecular Cloning Techniques*, S. L. Berger et al., eds., Academic Press (1987)). Preferably, the mRNA preparation used will be enriched in mRNA coding for APLP, either naturally, by isolation from cells which are producing large amounts of the protein, or in vitro, by techniques commonly used to enrich mRNA preparations for specific sequences, such as sucrose gradient centrifugation, or both.

For cloning into a vector, such suitable DNA preparations (either human genomic DNA or cDNA) are randomly sheared or enzymatically cleaved, respectively, and ligated into appropriate vectors to form a recombinant gene (either genomic or cDNA) library. A DNA sequence encoding APLP or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis et al., (In: *Molecular cloning, A Laboratory Manual*, Cold Spring Harbor Laboratories, Cold Spring Harbor, N.Y., (1982)), and are well known in the art.

Libraries containing APLP clones may be screened and an APLP clone identified by any means which specifically selects for APLP DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated APLP product produced by the host containing the clone.

Oligonucleotide probes specific for APLP which can be used to identify clones to this protein can be designed from knowledge of the amino acid sequence of APLP1 or APLP2.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., *In: Molecular Biology of the Gene*, 3rd Ed., W. A. Benjamin, Inc., Menlo Park, Calif. (1977)), one or more different oligonucleotides can be identified from the amino acid sequence, each of which would be capable of encoding the APLP. The probability that a particular oligonucleotide will, in fact, constitute the actual APLP coding sequence can be estimated by considering abnormal base pairing relationships and the frequency with which a particular codon is actually used (to encode a particular amino acid) in eukaryotic cells. Such "codon usage rules" are disclosed by Lathe et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the APLP sequences is identified.

The suitable oligonucleotide, or set of oligonucleotides, which is capable of encoding a fragment of an APLP gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate the cloned APLP gene by techniques known in the art. Techniques of nucleic acid hybridization and clone identification are disclosed by Maniatis et al. (In: *Molecular Cloning, A Laboratory Manual*, Cold Spring Harbor Laboratories, Cold Spring Harbor, N.Y. (1982)); Berger et al., (In: *Guide to Molecular Cloning Techniques*, Academic Press (1988)); Sambrook et al., (In: *Molecular Cloning, A Laboratory Manual*, Cold Spring Harbor Press, Cold Spring Harbor, N.Y., 2d ed. (1989); and by Hames et al. (In: *Nucleic Acid Hybridization, A Practical Approach*, IRL Press, Washington, D.C. (1985)), which references are herein incorporated by reference. Those members of the above-described gene library which are found to be capable of such hybridization are then analyzed to determine the extent and nature of the APLP encoding sequences which they contain.

To facilitate the detection of the desired APLP DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby et al., *J. Mol. Biol.* 113:237 (1977) and by T4 DNA polymerase replacement synthesis as described in, for example, Deen et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary et al., *Proc. Natl. Acad. Sci. U.S.A.* 80:4045 (1983); Renz et al., *Nucl. Acids Res.* 12:3435 (1984); and Renz, M., *EMBO J.* 6:817 (1983).

Thus, in summary, the actual identification of APLP sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing an APLP (i.e. APLP1 or APLP2) gene.

In an alternative way of cloning an APLP gene, a library is prepared using an expression vector, by cloning DNA or, more preferably cDNA prepared from a cell capable of expressing an APLP, into an expression vector. The library is then screened for members which express the APLP, for example, by screening the library with antibodies to the protein.

The above discussed methods are, therefore, capable of identifying genetic sequences which are capable of encoding an APLP or fragments of an APLP protein. In order to further characterize such genetic sequences, and, in order to produce the recombinant protein, it is desirable to express the proteins which these sequences encode. Such expression identifies those clones which express proteins possessing characteristics of an APLP. Such characteristics may include the ability to specifically bind an APLP antibody and the ability to elicit the production of antibody which are capable of binding to an APLP.

To express an APLP, transcriptional and translational signals recognizable by an appropriate host are necessary. The cloned APLP encoding sequences, obtained through the methods described above, and preferably in a double-stranded form, may be operably linked to sequences controlling transcriptional expression in an expression vector, and introduced into a host cell, either prokaryote or eukaryote, to produce recombinant APLP or a functional derivative thereof. Depending upon which strand of the APLP encoding sequence is operably linked to the sequences controlling transcriptional expression, it is also possible to express APLP antisense RNA or a functional derivative thereof.

Expression of the APLP in different hosts may result in different post-translational modifications which may alter the properties of the APLP. The present invention encompasses the expression of the APLP, or a functional derivative thereof, in eukaryotic cells, and especially mammalian, insect and yeast cells. Especially preferred eukaryotic hosts are mammalian cells either in vivo, in animals or in tissue culture. Mammalian cells provide post-translational modifications to recombinant APLP which include folding and/or glycosylation at sites similar or identical to that found for a native APLP. Most preferably, mammalian host cells include brain and neuroblastoma cells.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as an APLP encoding sequence and a promoter region sequence linked to the 5' end of the encoding sequence) are said to be operably linked if induction of promoter function results in the transcription of the APLP encoding sequence mRNA and if the nature of the linkage between the two DNA sequences does not (1) result in the introduction of a frame-shift mutation, (2) interfere with the ability of the expression regulatory sequences to direct the expression of the APLP mRNA, antisense RNA, or protein, or (3) interfere with the ability of the APLP template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

Expression of the APLP in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include those described above the promoter of the mouse metallothionein I gene (Hamer et al., *J. Mol. Appl. Gen.* 1:273–288 (1982)); the TK promoter of Herpes virus (McKnight, S., *Cell* 31:355–365 (1982)); the SV40 early promoter (Benoist et al., *Nature* (London) 290:304–310 (1981)); in yeast, the yeast gal4 gene promoter (Johnston et al., *Proc. Natl. Acad. Sci. U.S.A.* 79:6971–6975 (1982); Silver et al., *Proc. Natl. Acad. Sci. U.S.A.* 81:5951–5955 (1984)) or a glycolytic gene promoter may be used.

As is widely known, translation of eukaryotic mRNA is initiated at the codon which encodes the first methionine. For this reason, it is preferable to ensure that the linkage between a eukaryotic promoter and a DNA sequence which encodes an APLP, or a functional derivative thereof, does not contain any intervening codons which are capable of encoding a methionine. The presence of such codons results either in a formation of a fusion protein (if the AUG codon is in the same reading frame as the APLP encoding DNA sequence) or a frame-shift mutation (if the AUG codon is not in the same reading frame as the APLP encoding sequence).

If desired, a fusion product of an APLP may be constructed. For example, the sequence coding for APLP may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., metabolite. Also of interest are constructs wherein APLP mRNA and antisense RNA are provided in a transcribable form, but with different promoters or other transcriptional regulatory elements such that induction of APLP mRNA expression is accompanied by repression of antisense RNA expression, and/or repression of APLP mRNA expression is accompanied by induction of antisense RNA expression.

Translational signals are not necessary when it is desired to express APLP antisense RNA sequences.

If desired, the non-transcribed and/or non-translated regions 3' to the sequence coding for APLP can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells. Where the native expression control sequence signals do not function satisfactorily host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert an APLP DNA construct into the host cell chromosomal DNA, or to allow it to exist in an extrachromosomal form.

If the APLP DNA encoding sequence and an operably linked promoter is introduced into a recipient eukaryotic cell as a non-replicating DNA (or RNA) molecule, which may either be a linear molecule or a closed covalent circular molecule which is incapable of autonomous replication, the expression of the APLP may occur through the transient expression of the introduced sequence.

Genetically stable transformants may be constructed with vector systems, or transformation systems, whereby APLP DNA is integrated into the host chromosome. Such integration may occur de novo within the cell or, in a most preferred embodiment, be assisted by transformation with a vector which functionally inserts itself into the host chromosome, for example, with retroviral vectors, transposons or other DNA elements which promote integration of DNA sequences in chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., pp. 445–470 (1981); Broach, J. R., *Cell* 28:203–204 (1982); Bollon et al., *J. Clin. Hematol. Oncol.* 10:39–48 (1980); Maniatis, T., In: *Cell Biology: A Comprehensive Treatise,* Vol. 3, "Gene Expression," Academic Press, N.Y., pp. 563–608 (1980)), and are commercially available. For example, mammalian expression vector systems which utilize the MSV-LTR promoter to drive expression of the cloned gene, and in which it is possible to cotransfect with a helper virus to amplify plasmid copy number, and integrate the plasmid into the chromosomes of host cells have been described (Perkins et al., *Mol. Cell Biol.* 3:1123 (1983); Clontech, Palo Alto, Calif.).

Once the vector or DNA sequence containing the construct(s) is prepared for expression, the DNA construct(s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of an APLP, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like.

The APLP DNA encoding sequences, obtained through the methods above, will provide sequences which, by definition, encode an APLP and which may then be used to obtain APLP antisense RNA genetic sequences as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of an APLP antisense RNA in the transformed cell. Antisense RNA and its expression may be used to interact with an endogenous APLP DNA or RNA in a manner which inhibits or represses transcription or translation of an APLP gene in a highly specific manner. Use of antisense RNA probes to block gene expression is discussed in Lichtenstein, C., *Nature* 333:801–802 (1988). For example, such probes can be used to block the expression of an APLP when the expression is aberrant.

Having generally described the invention, the same will be more readily understood through reference to the following examples which are provided by way of illustration and are not intended to be limiting.

EXPERIMENTAL

EXAMPLE 1

Materials and Methods

Cell Culture and Protein Extracts

Human neuroglioma H4 cells were maintained in DMEM medium supplemented with 10% fetal calf serum, 1% L-glutamine and 1% penicillin-streptomycin at 37° C. in a humidified atmosphere containing 5% $CO_2$/95% $O_2$.

Nuclear extracts were prepared according to Miner et al. (Miner, L. L. et al., *J. Neurosci. Res.* 33:10–18 (1992)). Final protein concentration varied between 0.5 and 2 mg/ml.

Preparation of DNA Fragments and Plasmid Constructs

Two complementary oligonucleotides were synthesized for each DNA fragment employed in gel mobility shift assays. The oligonucleotides were annealed and end-labeled with [$\alpha$-$^{32}$P]dCTP by fill-in reaction.

The sequence of the DK-1 fragment extends from −30 to −58 from the primary transcriptional site of the human APP promoter (Salbaum, J. M. et al., *EMBO J.* 7:2807–2813 (1988)) and contains the AP-1/AP-4 element (underlined): 5'GGGCCGGATCAGCTGACTCGCCTGGCTCT3' SEQ. ID. NO:2. The randomized versions of the DK-1 fragment contain selectively randomized sequences, underlined as follows: 5'Random: 5'GCTTACTGTCAGCTGACTCGC-CTGGCTCT3' SEQ. ID. NO:4; AP-1/AP-4 Random: 5'GGGCCGGAATCGTGCTGTCGCCTGGCTCT3' (SEQ. ID. NO:5); 3' Random: 5'GGGCCGGATCAGCTGAC-GATACCTGTCCG3' (SEQ. ID. NO:6). The AP-1 fragment contains a consensus sequence for the c-fos/c-jun transcription factors (Mermod, N. et al., *Nature* 332:557–561 (1988)) (underlined): 5'GATCCAGCTGACTCATCACTAG3' (SEQ. ID. NO:7). The consensus sequence for the AP-4 transcription factor (Hu, Y. -F. et al., *Genes Dev.* 4:1741–1752 (1990)) is underlined in the following sequence: 5'GATCACCAGCTGTGGAATGTGTGTGATC (SEQ. ID. NO:8). Finally, the core sequence of the USF binding site (Gregor, P. D. et al., *Genes Dev.* 4:1730–1740 (1990)) is inserted into the USF fragment: 5'GGGCCGGAT-CACGTGACTCGCCTGGCTCT3' (SEQ. ID. NO:9).

The hAPP-luciferase construct was prepared by inserting a 2.9 kb EcoRII/BamHI APP promoter fragment (Salbaum et al., *EMBO J.* 7:3807 (1988)) into the SmaI site of the luciferase expression vector pxP2 (Nordeen, S. K. *Biotechniques* 6:454 (1988)). The pML$\Delta$53($C_2$AT) plasmid was constructed as described (Roy et al., *Nature* 354:245 (1991)). The pCMV-USF construct was prepared by inserting the gene encoding the 43 kDa USF protein into the pCMV vector. The pCMV-aplp1 and pCMV-aplp2 constructs were prepared by inserting the gene encoding the aplp1 and aplp2 proteins (described below) into the pCMV vector.

Electrophoretic Mobility Shift Assay (EMSA)

EMSA was carried out as in Miner et al. (Miner, L. L. et al., *J. Neurosci. Res.* 33:10–18 (1992)). 1 ng of DNA fragment was incubated with 1 µg nuclear extract for 20 rain at 20° C., unless otherwise indicated. Quantities of rUSF (Pognonec, P. et al., *Mol. Cell Biol* 11:5125–5136 (1991)) are indicated in the figure legends. After incubation, the binding mixture was resolved on 6% polyacrylamide gels containing 4% glycerol in 25 mM Tris-borate (pH 8.3), 0.5 mM EDTA. Gels were dried and exposed to Kodak X-OMAT AR film with intensifying screen.

Western Analysis and Antibodies

Protein extracts were size-fractionated on 8% polyacrylamide gels according to Laemmli (Laemmli, U. K. *Nature* 227:680–685 (1970)) and were transferred to Immobilon P (Millipore) electrophoretically at 100 V in 20 mM Tris (pH 7.4), 150 mM glycine and 20% methanol for 4 hr at 4° C. Membranes were blocked 10 mM Tris (pH 8.0), 150 mM NaCl, 0.05% Tween 20, 3 % BSA, 0.05 % $NaN_3$ for 1 hr at 20° C. After incubation with the USF antiserum (Kaulen, H. et al., *Mol. Cell. Biol.* 11:412–424 (1991)), the membranes were immunostained using a light-emitting luminol/horseradish peroxidase system (ECL Western blotting; Amersham), according to the manufacturer's protocol. The c-fos antiserum (Oncogene Products, Manhasset, N.Y.) was prepared against the DNA-binding epitope of the c-fos protein.

In vitro Transcription and Primer Extension

In vitro transcription was performed according to Dignam, J. D. et al., *Nucleic Acids. Res.* 11: 1475–1489

(1983), modified as recommended by the manufacturer (Promega Corp.). Primer extension was carried out on the transcription product as described in Martinez, E. et al., *EMBO J.* 13:3115–3126 (1994). The primer specific for the hAPP-luciferase construct corresponds to part of the multiple cloning site between the promoter and the reporter gene with the following sequence: 5'-GCTCAGATCTCGA GCTCGGTAC-3' (SEQ. ID. NO:3). The primer for the MLΔ53 plasmid encompasses 19 bp of the G-less cassette: 5'-GGAAATATAGAAGAAGGAG-3' (SEQ. ID. NO:10). RNA and end-labeled primers were hybridized in 50% formamide, 10 mM Tris (pH 7.5), 250 mM KCl and 1 mM EDTA for 10 min at 65° C. and overnight at 42° C. Sequencing reaction was performed using the APP primer extension oligonucleotide according to the directions suggested by the manufacturer (United States Biochemical Corp.).

Results

DNA-Protein Binding at the AP-1/AP-4 Site Using H4 Cell Nuclear Extracts

Figure 1B:
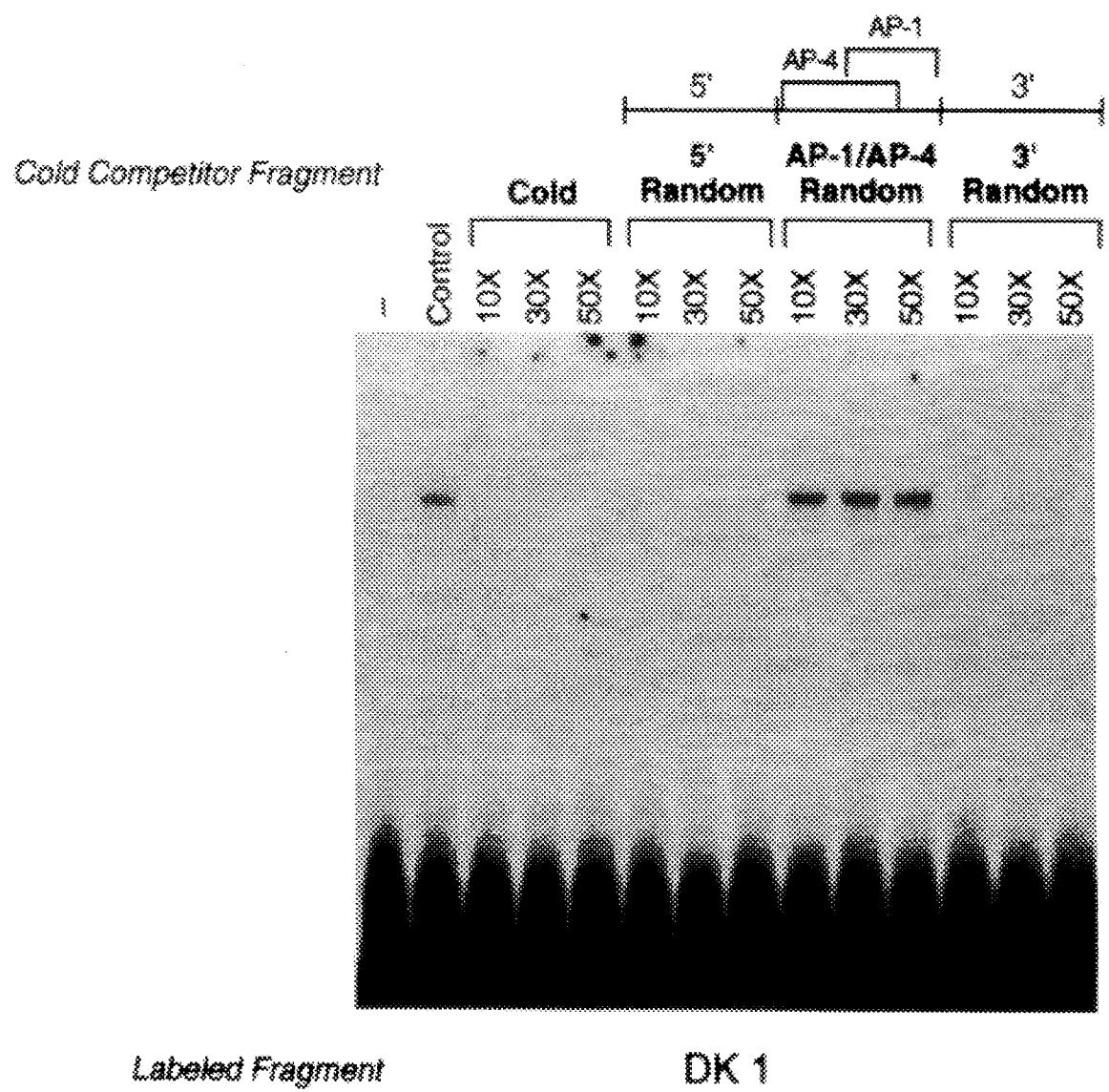

To examine whether the AP-1/AP-4 element binds to transcription factors present in the nucleus of H4 neuroglioma cells, a 29 bp $^{32}$P-labeled doublestranded DNA fragment (DK-1, see FIG. 1A (SEQ ID NO:2)) containing the AP-1/AP-4 site was incubated in the presence of H4 nuclear extracts and separated on a non-denaturing polyacrylamide gel (electrophoretic mobility shift assay, EMSA). One discrete band was observed (FIG. 1B). The specificity of the binding was assessed by the addition of increasing amounts of cold fragment, which resulted in a very rapid decrease of the binding on the labeled fragment.

To identify the region within the 29 bp DK-1 fragment that is responsible for the binding, three differentially mutated double-stranded DNA fragments were synthesized for use in competition assays. The first of these contained a random sequence in place of the region upstream of the AP-1/AP-4 site, the second contained a random sequence in place of the AP-1/AP-4 element itself, and the third contained a random sequence in place of the region downstream from the AP-1/AP-4. Binding to the labeled fragment was significantly diminished only in the presence of the two competitor fragments that still contained an intact AP-1/AP-4 site, while the competitor fragment that contained a random sequence in place of the AP-1/AP-4 site did not effectively compete for binding. These results indicate that the H4 nuclear extract contains a factor that specifically binds to the AP-1/AP-4 element of the APP promoter.

Figure 2:
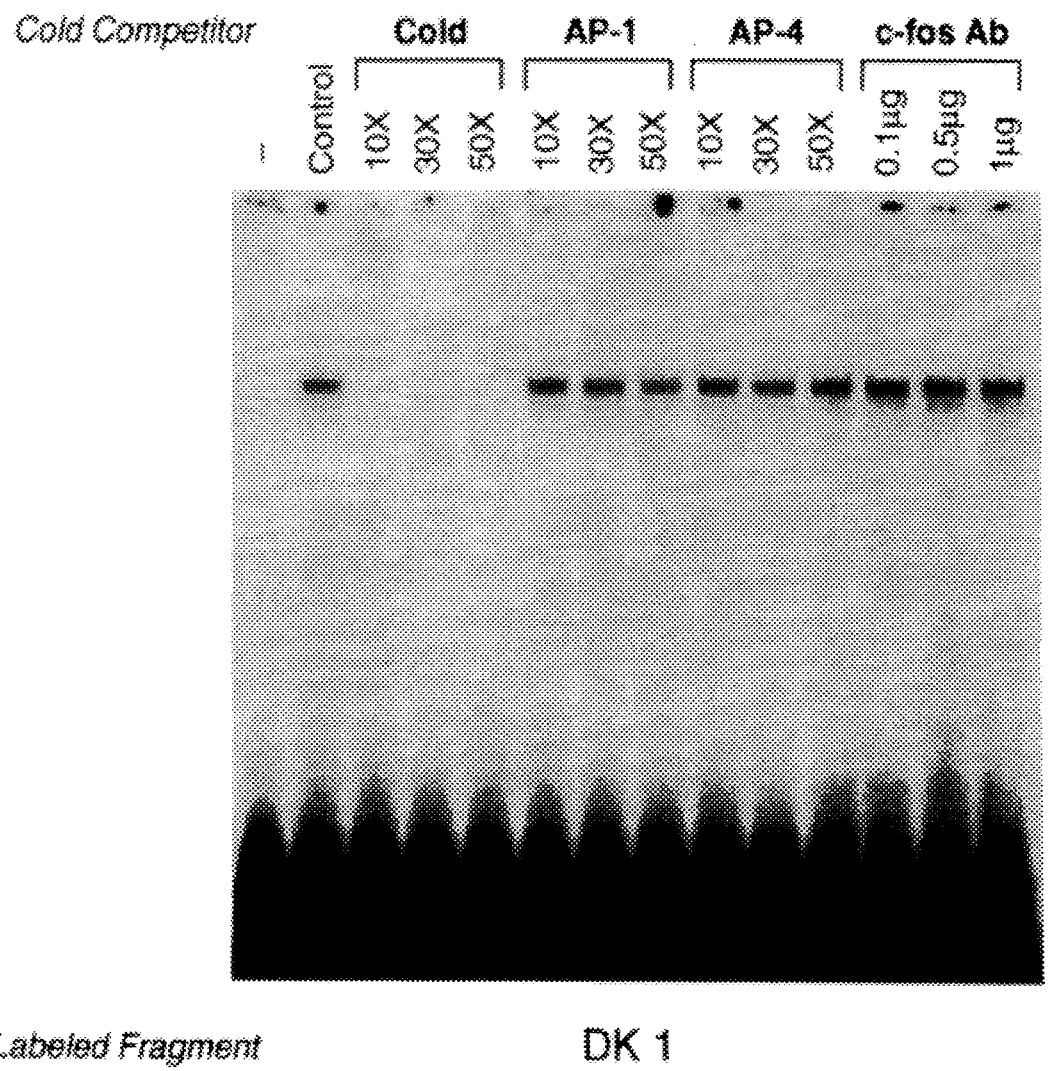
FIG. 2. Competition assay using AP-1 and AP-4 consensus elements and a c-fos mAb. EMSA carried out with increasing amounts (0–50-fold) of competitors. Cold: DK-1 fragment.

DNA-Protein Interaction at the AP-1/AP-4 Site Involves a Factor Different from the c-Fos/c-Jun or AP-4 Factors The c-fos/c-jun complex is known to interact with the AP-1 sequence alone. Therefore, to determine whether the protein binding to the combined AP-1/AP-4 site was either the c-fos/c-jun complex or the AP-4 factor, EMSA was performed in the presence of DNA fragments containing consensus sequences for the AP-1 and the AP-4 elements and in the presence of a monoclonal antibody directed against the DNA binding site of c-fos (FIG. 2). None of these agents affected the binding to the AP-1/AP-4 site in our system. Next, specific binding to the AP-1 consensus sequence was assessed by labeling this fragment and incubating it with the H4 nuclear extract. The resulting DNA-protein complex migrated more slowly than that observed using the AP-1/AP-4 element (see FIG. 4B), was specifically diminished in the presence of increasing amounts of c-fos antibody, and was not affected by the presence of a 50-fold excess of DK-1 fragment (data not shown). Collectively, these data indicate that the binding at the AP-1/AP-4 site does not involve the c-fos/c-jun complex or the AP-4 factor.

Figure 3:
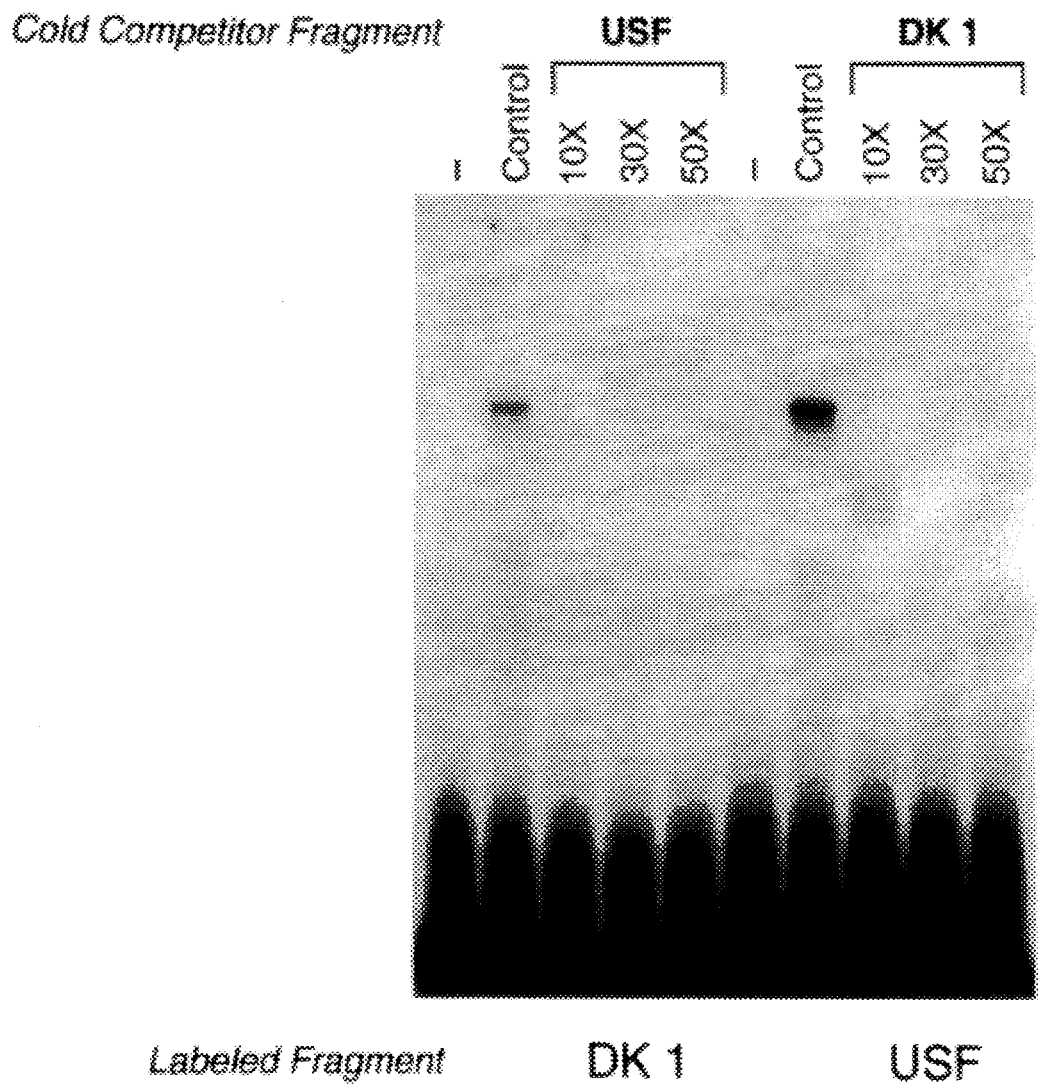
FIG. 3. Competition assay using the USF core sequence EMSA, employing either labeled DK-1 fragment, with increasing amounts (0–50-fold) of cold USF fragment, or labeled USF fragment with increasing amounts (0–50-fold) of cold DK-1 fragment.

The Factor Binding the AP-1/AP4 Site Also Interacts with the USF Binding Site A double-stranded DNA fragment incorporating the core sequence of the consensus element for USF, CACGTG, was labeled and incubated with the H4 nuclear extract. The resulting complex exhibited a very similar pattern of migration to that obtained with the AP-1/AP-4 site in the core position, and was specifically and rapidly diminished following the addition of cold DK-1 fragment to the incubation mixture (FIG. 3). Conversely, the formation of the complex using the AP-1/AP-4 element was also rapidly abolished in the presence of the cold USF fragment. These experiments indicate that the DNA-protein complexes formed at the AP-1/AP-4 and USF sites include either the same or related factors.

Antiserum Raised Against USF Recognizes the Complex on the AP-1/AP-4 Site

Figure 4A:
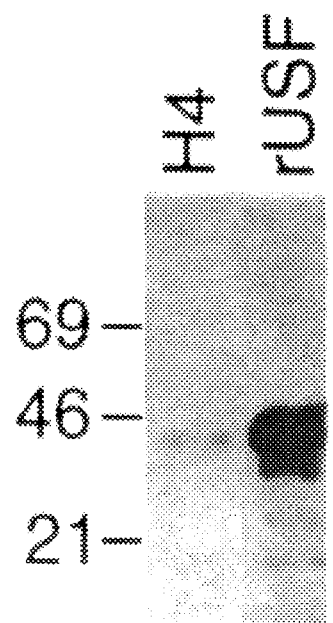
FIGS. 4A-B. Antiserum anti-USF binds the protein complex on the AP-1/AP-4 site. (A) Detection of USF in nuclear extracts obtained from H4 cells by Western blot analysis, using an antiserum raised against the 43 kDa form of USF. H4: 40μg of nuclear extract from H4 cells. rUSF: 100 ng of recombinant 43 kDa USF. (B) Competition assay using a USF antiserum: EMSA in presence of increasing amounts of anti-USF antiserum, employing either labeled DK-1 fragment, or labeled AP-1 fragment.
Figure 4B:
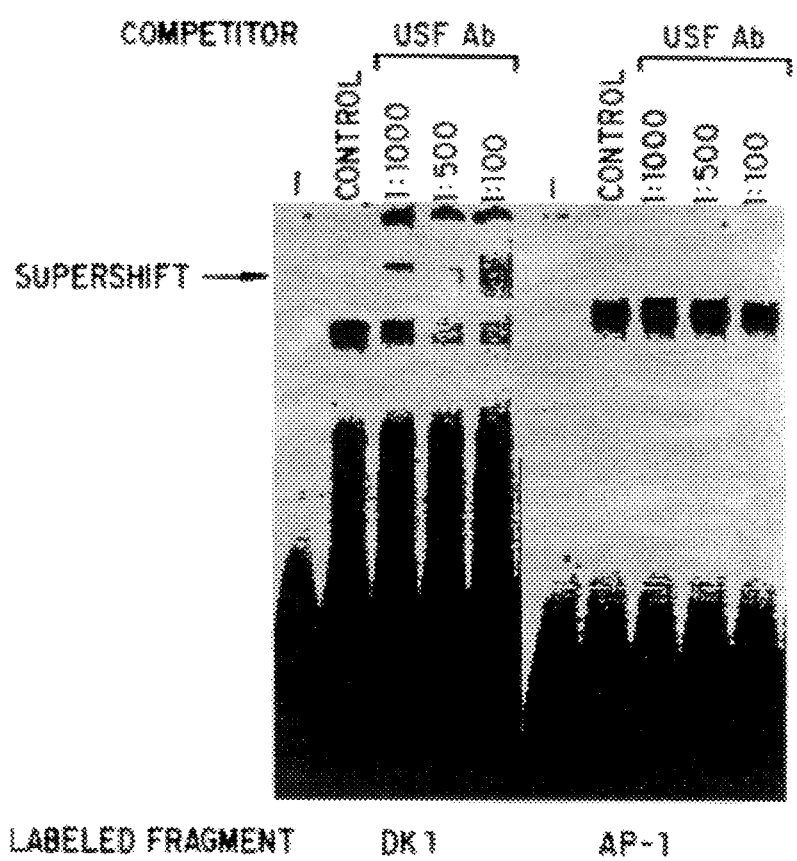

We next investigated whether USF is a component of the DNA-protein complex formed with the AP-1/AP-4 site. For this purpose we first tested for the presence of USF in the H4 nuclear extract with a polyclonal antiserum raised against the 43 KDa form of USF and demonstrated the presence of a single band at around 43 kDa, which comigrates with the recombinant USF protein (FIG. 4A). The same anti-USF antiserum also had the ability to significantly modify the migration rate of the complex formed on the AP-1/AP-4 site (FIG. 4B). It caused a marked decrease in the amount of normal DNA-protein complex formation, and resulted in the formation of a new, more slowly migrating complex. This complex is the result of an interaction of the USF antibody with the DNA-protein complex and thus constitutes a "supershift." Increased amounts of anti-USF antiserum resulted in the elimination of the slower migrating band. The specificity of the complex formation was confirmed by showing that the anti-USF antiserum did not affect the complex formation on the AP-1 site alone. Control antibodies directed against another protein, $APP_{751}$, did not affect the complex formation on the AP-1/AP-4 site (dam not shown). Taken together, these data indicate that the factor present in the DNA-protein complex formed with the AP-1/AP-4 element is antigenically related to USF.

Recombinant 43 KDa USF Binds to the AP-1/AP-4 Element

Figure 5:
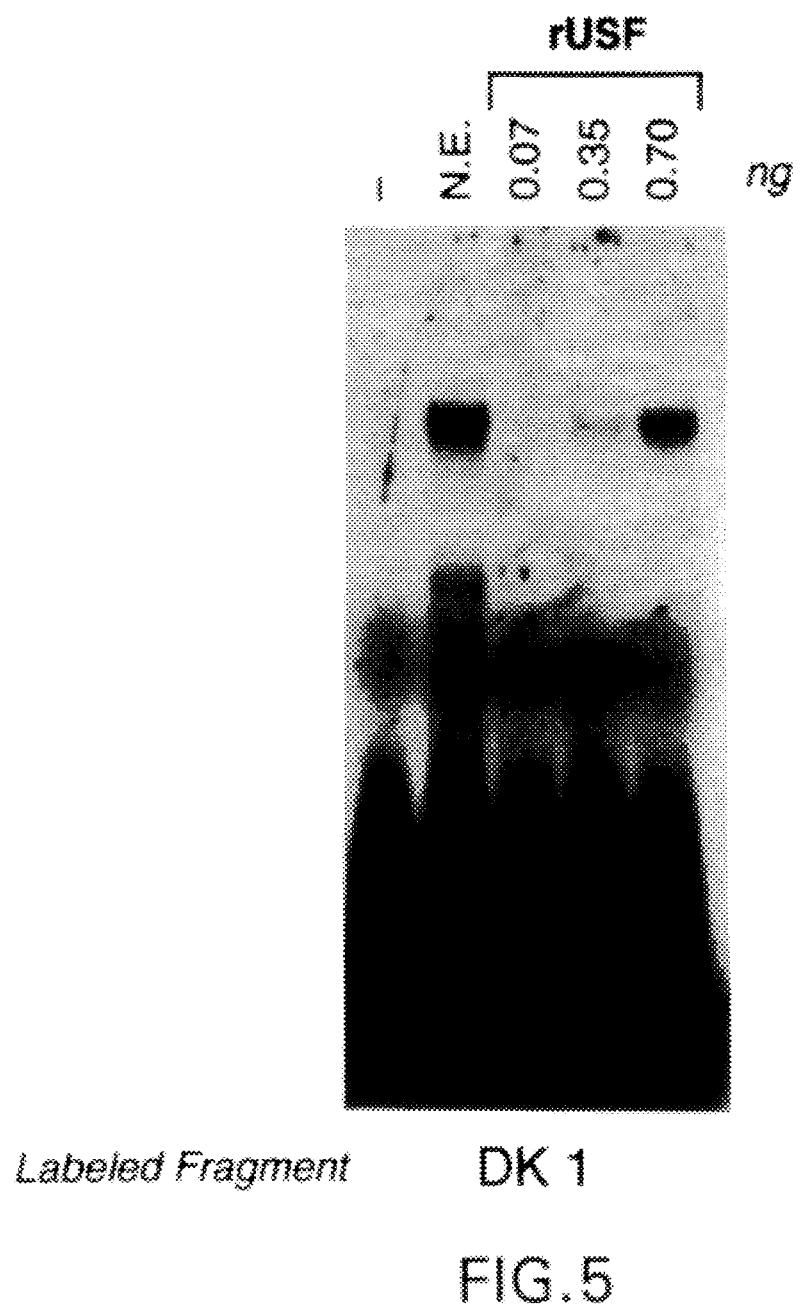
FIG. 5. Interaction between recombinant USF and the AP-1/AP-4 site. EMSA using 70–700 pg of rUSF and labeled DK-1 fragment. EMSA employing rUSF, in presence of increasing amounts (0–50-fold) of either cold DK-1, or AP-1/AP-4 randomized fragments.

In order to demonstrate a direct interaction between the AP-1/AP-4 site and USF, we employed the 43 kDa form of USF expressed in, and purified from, bacteria. This recombinant USF (rUSF) polypeptide has been shown to bind to its consensus sequence in EMSA, exhibiting a pattern very similar to that obtained with various nuclear extracts (Pognonec, P. et al., *Mol. Cell Biol* 11:5125–5136 (1991)). Incubation of the DK-1 fragment with small amounts (350 pg) of rUSF resulted in the formation of a visible complex, exhibiting the same migration pattern obtained with the H4 nuclear extract (FIG. 5). The amount of complex formed decreased with increasing amounts of cold fragment. The specificity of the binding of rUSF to the AP-1/AP-4 site was demonstrated through competition experiments using non-radioactive DK-1 fragment in which the AP-1/AP-4 site was replaced by a randomized sequence. The addition of cold DK-1 fragment containing randomized AP-1/AP-4 site failed to diminish DNA-protein formation on the labeled DK-1 fragment (dam not shown). These results indicate that rUSF binds specifically to the AP-1/AP-4 site, and strongly suggest that the USF protein present in the H4 cell nuclear extract is partly or fully responsible for the formation of the DNA-protein complex on the AP-1/AP-4 site present in the APP promoter.

The Presence of USF Maintains Elevated Levels of Constitutive APP Expression

To test the ability of USF to modulate transcription from the APP promoter, cell-free in vitro transcription reactions were performed using HeLa cell nuclear extracts in the presence of increasing amounts of the DNA fragment containing the consensus element for USF.

Figure 6A:
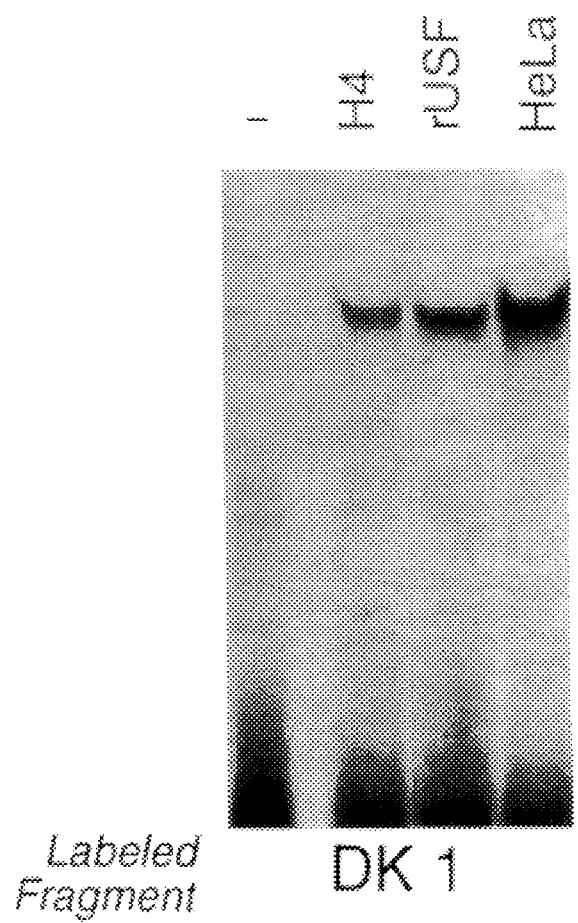
FIGS. 6A–C. EMSA and cell-free transcription from the APP promoter with HeLa extracts. (A) EMSA showing the shift pattern with HeLa cell nuclear extracts. 1 μ H4 nuclear extract, rUSF: 700 pg rUSF. HeLa: 1 μg HeLa cell nuclear extract. (B) Determination of the 5'-end of the in vitro transcription product of the hAPP-luciferase construct by primer extension and comparison with the sequencing product of the construct, using the same oligonucleotide. The major transcription initiation site is indicated by an arrow. (C) In vitro transcription in the presence of competing DNA fragments. 1 μg of the hAPP-luciferase and 0.5 μg of the pMLΔ53(CA$_2$T) templates were incubated in the absence and presence of a 20-fold molar excess of USF fragment or AP-1/AP-4 Random fragment.
Figure 6B:
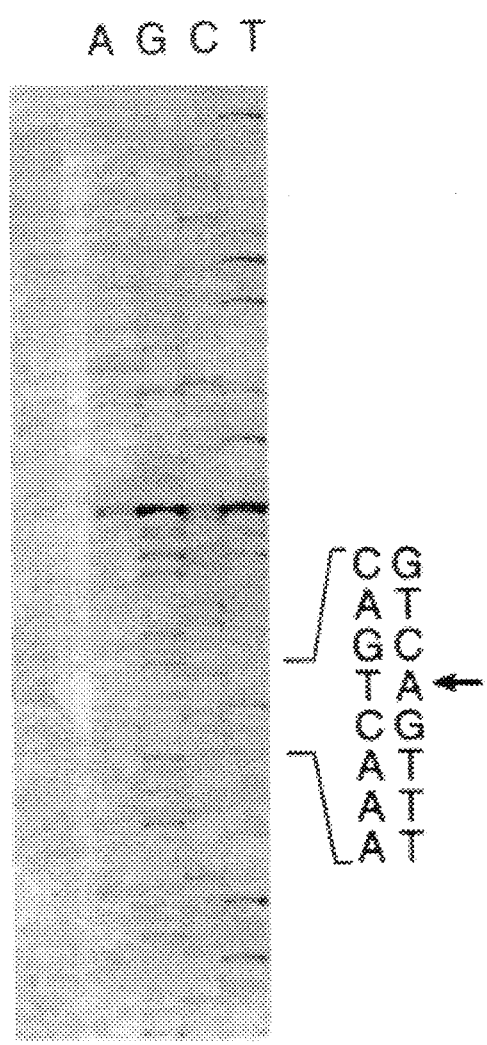

The presence of USF in HeLa cell nuclear extracts has previously been characterized (Pognonec, P. et al., Mol. Cell. Biol. 11:5125–5136 (1991)) and confirmed in this study by Western Blot analysis (data not shown). USF levels are higher in HeLa nuclear extracts than in the H4 neuroglioma extracts, as indicated by increased binding to the DK 1 fragment (FIG. 6A). In the cell-free transcription assays, the correct transcription initiation site was demonstrated in the hAPP-luciferase construct by primer extension and by direct sequencing with a primer located downstream from the BamHI site at position +105. Additional transcription initiation sites were also found (FIG. 6B), and correspond to those reported by La Fauci, G. et al., Biochem. Biophys. Res. Commun. 159:297–304 (1989).

Figure 6C:
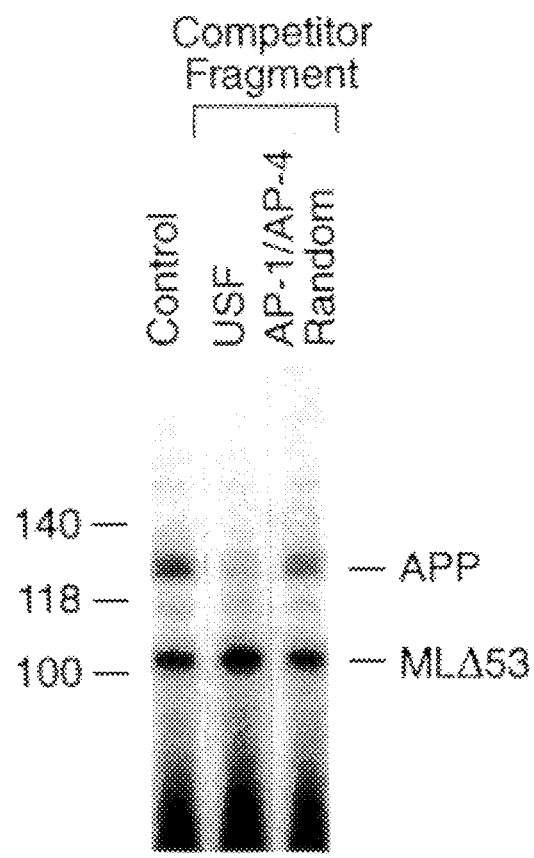

Two constructs, one containing the APP promoter and one containing 53 bp of the adenovirus major late promoter lacking a USF site (Roy, A. L. et al., Nature 354:245–248 (1991), were used in the same in vitro transcription reaction. FIG. 6C shows that the addition of a 20-fold molar excess of the DNA fragment containing the USF consensus site significantly decreases transcription from the APP promoter. Conversely, the presence of the DNA fragment in which the AP-1/AP-4 site was replaced by a random sequence does not decrease transcription at the same molar concentration. The control construct indicated similar levels of transcriptional efficiency in the reactions. These dam indicate that the presence of USF in the nuclear extract is important for maintaining the basal level of transcription from the human APP promoter.

Recombinant 43 KDa USF Activates Transcription from the APP Promoter

Figure 7:
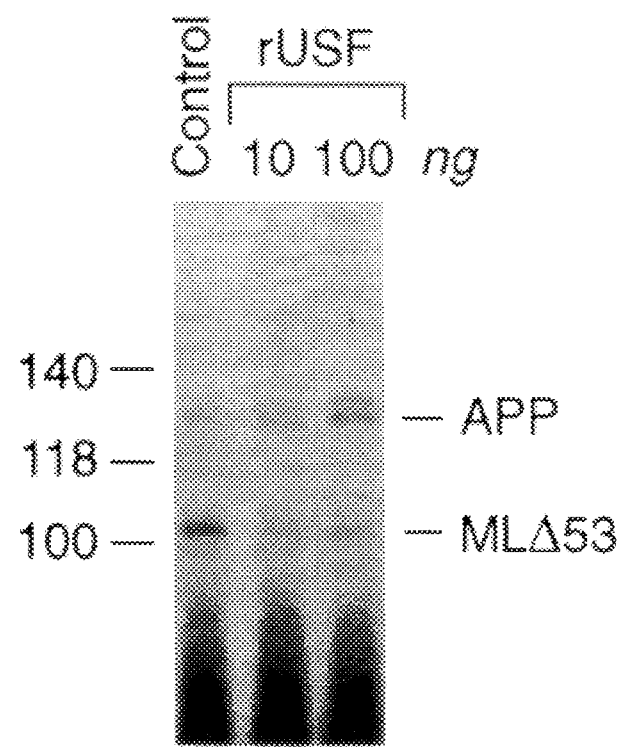
FIG. 7. Transactivation of the APP promoter by USF in cell-free transcription assays. In vitro transcription assay with 1.5 μg of hAPP-luciferase and 1 μg pMLΔ53(CA$_2$T) templates in the absence and presence of 10 and 100 ng rUSF.

To examine whether USF can increase transcription from the APP promoter above basal levels, 100 ng of rUSF were added to the in vitro transcription reactions, followed by primer extension analysis (FIG. 7). The amount of transcription product doubled under these conditions. 50 ng of rUSF were sufficient to yield a similar increase (data not shown). The high levels of USF already present in the HeLa nuclear extracts may serve to mask a more robust increase in transcription levels following the addition of rUSF. These results suggest that USF participates in the activation of transcription from the APP promoter, and that levels of USF in the nucleus strongly correlate with the amount of APP mRNA synthesized.

Figure 8:
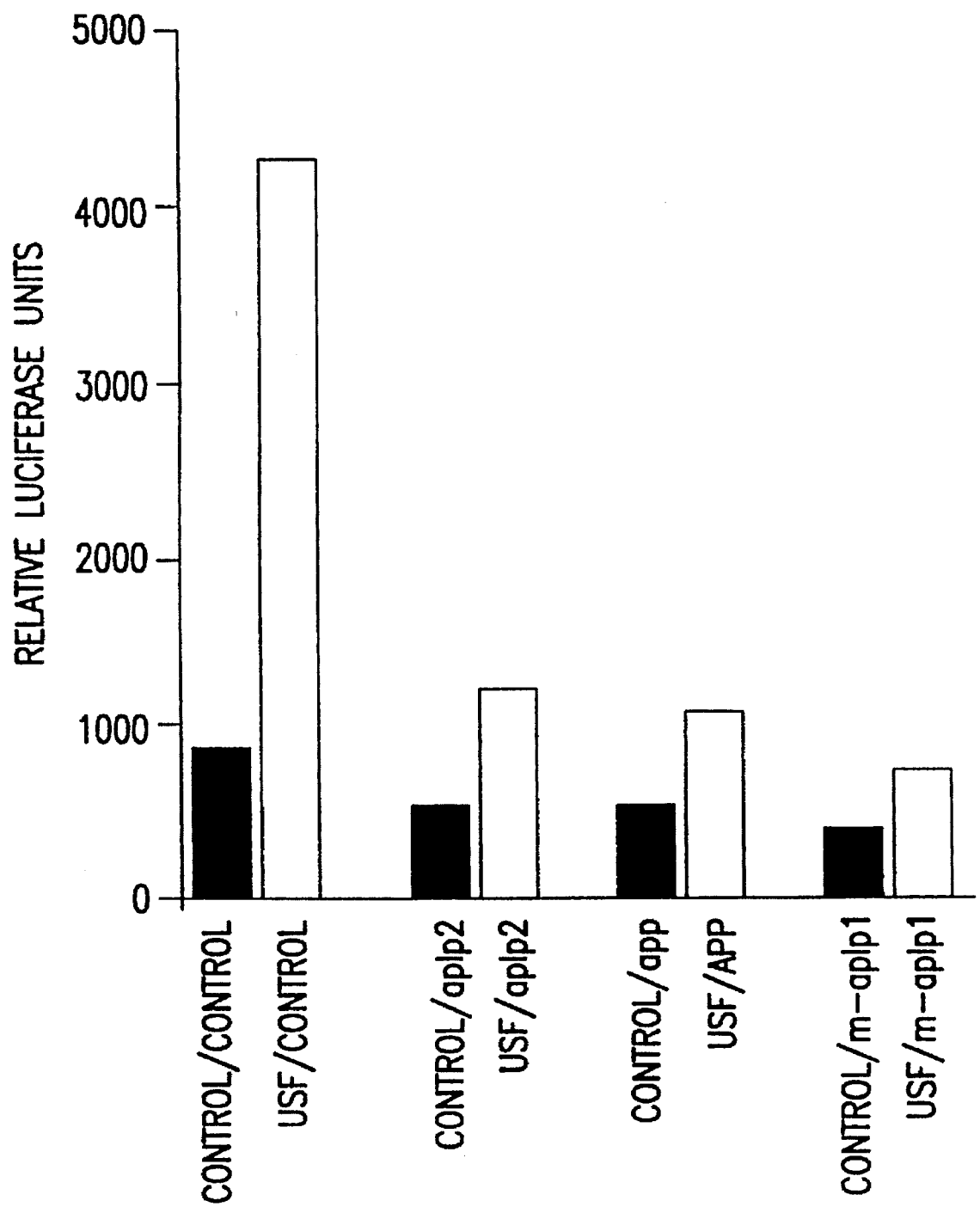
FIG. 8. H4 neuroglioma cells were cotransfected with three constructs: the APP promoter-luciferase reporter gene construct, the USF expression vector or its control plasmid, and the APP/APLP family expression vectors or their control plasmid. The effects on expression from the APP promoter are shown graphically.

Recombinant 43 KDa USF and the APP/APLP Family Modulate Transcription from the APP Promoter H4 neuroglioma cells were cotransfected with three constructs: the APP promoter-luciferase gene construct, the USF expression vector (pCMV-USF) or its control plasmid, and the APP/APLP family expression vectors (pCMV-aplp1, pCMV-aplp2, and pCMV-APP) or their control plasmid. The results were assayed in terms of relative luciferase units and showed that expressing USF alone in the neuroglioma cells activated transcription from the APP promoter about 5-fold as compared to the control. However, when either APLP1, APLP2, or APP was also expressed in the cells, in each instance, USF activation of transcription from the APP promoter decreased to that of about 2-fold as compared to the control. These results are shown graphically in FIG. 8.

EXAMPLE 2

Materials and Methods

Neuroblastoma NB2A cells were maintained as previously described (Magendantz et al., Proc. Natl. Acad. Sci. U.S.A. 82:6581–6585 (1985)). Radionucleotides were obtained from New England Nuclear and Amersham. Restriction enzymes were obtained from New England Biolabs and PCR reagents from Perkin-Elmer.

Screening of λgt11 Libraries. General techniques for preparing and screening libraries are disclosed in Maniatis et al., Molecular Cloning, A Laboratory Manual, Cold Spring Harbor Laboratory, Cold Spring Harbor, N.Y., 2d ed. (1989). Three different libraries were used to obtain mouse brain cDNA clones in λgt11. A random primed and an oligo-dT primed library were obtained from Clontech. An oligo-dT primed library was obtained from Stratagene. Libraries were screened by hybridization to nitrocellulose (BA85, Schleicher and Schuell) or Nylon (Hybond-N, Amersham) according to standard procedures using cDNA that was labeled by random priming (Feinberg et al., Anal. Biochem. 132:6–13 (1983)). Positive clones were sized by PCR amplification of the λgt11 insert using primers 1218 and 1222 from New England Biolabs.

Recombinant DNA Techniques

DNA fragments were subcloned into pBluescript (Stratagene) or M13 (New England Biolabs) vectors and both strands were sequenced with Sequenase (U.S. Biochemical) according to the manufacturer's instructions. Sequence analyses were done using the UWGCG programs at the Whitaker College Computing Facility at MIT.

RACE Procedure for Obtaining 5' cDNA Extensions

The RACE (Rapid Amplification of cDNA Ends) procedure that was used is a combination of the methods of Frohman et al. (Frohman et al., Proc. Natl. Acad. Sci. U.S.A. 85:8998–9002 (1988)) and Ohara et al. (Ohara et al., Proc. Natl. Acad. Sci. U.S.A. 86:5673–5677 (1989)). For the RACE procedure, the primers were the complements of nucleotides 699–719 and 672–692 of the sequence presented in FIG. 10 (SEQ ID NO:5). RACE products were subcloned into pBluescript, screened by hybridization to the 5' 120 bp EcoRI-PstI fragment of 69A and positive clones were sequenced.

RNA Analysis

PolyA+RNA was prepared as in Badley et al. (Badley et al., BioTechniques 6:114–116 (1988)), using oligo-dT beads (Collaborative Research). For Northern blot analysis the RNA was separated on an agarose gel containing formaldehyde, transferred to nylon (BioTrace, Gelman Sciences) according to standard methods (Sambrook et al., *Molecular Cloning (A Laboratory Manual)*, Cold Spring Harbor Laboratory, (1989)), and crosslinked to the nylon using a UV Crosslinker (Stratagene). The blots were hybridized and washed according to the method of Church and Gilbert (Church et al., *J. Cell Biol.* 107:1765–1772 (1988)). The molecular weight of the transcripts was determined by using RNA molecular weight markers.

Production Antisera to an APLP Peptide

A peptide with the sequence QQLRELQRH (SEQ ID NO:1) was obtained from the Biopolymers laboratory of the Howard Hughes Medical Institute and Center for Cancer Research at MIT. 20 mg of the peptide was conjugated to KLH essentially as described in Marcantonio, C. G., and Hynes, R. O., *J. Cell Biol.* 107:1765–1772 (1988), and the immunization of four New Band white rabbits was carried out as described in Schatz et al. (Schatz et al., *Mol. Cell Biol.* 7:3799–3805 (1987)).

Protein Preparation

Protein from neuroblastoma cells was isolated by rinsing the cells with PBS followed by lysing the cells in SDS sample buffer and boiling. Protein from mouse brain was isolated by homogenizing one brain in 1 ml of RIPA buffer (50 nM Tris pH 7.4, 150 mM NaCl, 5 mM EDTA, 1% Triton X-100, 1% Na deoxycholate, 0.1% SDS and protease inhibitors). The homogenate was spun in an Eppendorf centrifuge for 30 minutes at 4° C., combined with SDS sample buffer and boiled.

β-galactosidase Fusion Protein Preparation

A β-galactosidase-APLP1 fusion protein was constructed using standard techniques (Sambrook et al., *Molecular Cloning (A Laboratory Manual)*, Cold Spring Harbor Laboratory, (1989)). An EcoRI-EcoRI fragment from a λgt11 clone containing 666 nucleotides of the 3' coding portion (nucleotides 1380–2046 of FIG. 10 (SEQ ID NO: 15)), and 258 nucleotides of the untranslated region of the APLP (nucleotides 2047–2305 of FIG. 10 (SEQ ID NO:15)) was ligated into the EcoRI site of a pUEX5 vector.

To prepare total protein lysates from bacteria containing these plasmids, an overnight culture, diluted 1:10 into L-broth plus ampicillin, was grown for 1.5–2 hours at 300, then induced at 42° (or left at 30° for uninduced samples) for 2.5–3 hours. The bacteria were then spun down, resuspended in 50% SDS sample buffer containing protease inhibitors and sonicated to shear chromosomal DNA.

Western Blot Analysis

Protein samples were subjected to polyacrylamide gel electrophoresis, transferred to nitrocellulose and probed with rabbit antibodies and $^{125}$I-labelled protein A essentially as described in Birgbauer (Birgbauer et al., *J. Cell Biol.* 109:1609–1620 (1989)).

Immunofluorescence

Neuroblastoma cells were plated onto glass coverslips approximately forty eight hours before fixation. Twenty four hours before fixation, the concentration of fetal calf serum in the medium of neuroblastoma cells was changed from 10% to 0.1% to induce neurite extension. Twenty minutes before fixation, concanavalin A was added to 20 mg/ml to encourage cell adhesion to the coverslips. Cells were fixed in 3.7% formaldehyde/PBS, permeabilized in acetone and blocked for 30 minutes at 37° in PBS containing 1% calf serum. Primary antibody was diluted into the blocking buffer, applied to the cells for 30 minutes and visualized with FITC conjugated goat anti-rabbit antibody. Cells were observed and photographed using a Zeiss Axioplan microscope. For the peptide competition experiment, the peptide was preincubated with the primary antibody in blocking buffer for 30 minutes before adding it to the cells (Donaldson et al., *J. Cell Biol.* 111:2295–2306 (1990) and Moremen et al., *J. Biol. Chem.* 260:6654–6662 (1985)).

Results

Identification and Cloning of APLP1

In a screen for cDNA clones encoding a microtubule-associated protein (MAP), a clone was isolated from a mouse brain cDNA library (Stratagene) which was found to have an open reading frame (ORF) homologous to that of APP. The probe that was used to screen was an antibody elicited against MAP. APLP1 is not related to any known MAP.

Figure 9:
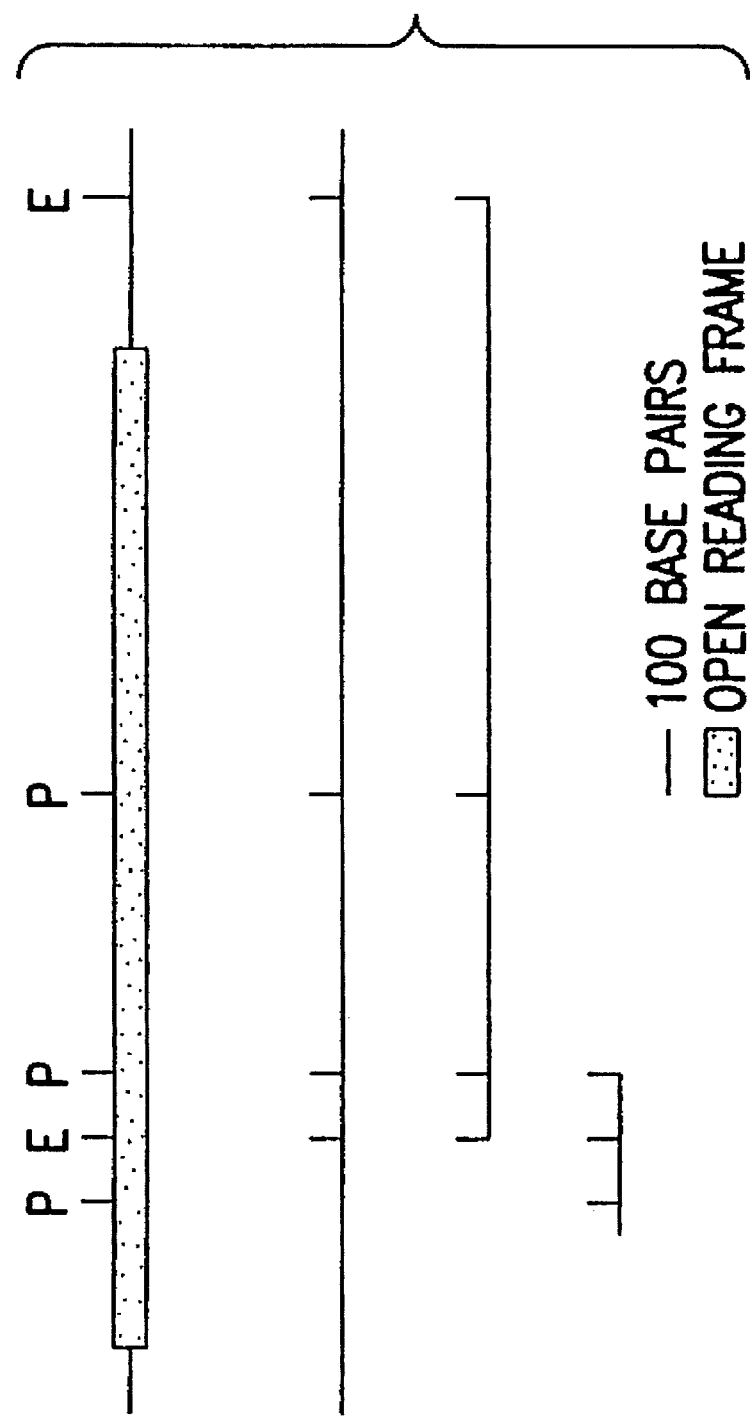
FIG. 9. Schematic representation of the mouse APLP1 open reading frame and the relation of various cDNA clones. The 2361 base pair open reading frame and the non-coding region of the APLP1 cDNA are shown. Also shown are the relative locations of two representative cDNA clones found in 11 libraries, 69A and 1A, and a clone obtained through the RACE procedure. J. Restriction enzyme sites: E=EcoRI, P=PstI.

The cDNA clone in which the APP homology was originally identified contained a portion of the C-terminal coding sequence as well as a portion of the 3' untranslated region. To extend the APLP1 ORF in the 5' direction, probes were used from the 5'-most regions of available cDNA clones to screen two Clontech λgt11 libraries. Repetitive screens using progressively more upstream probes resulted in the isolation of a 1.8 kb cDNA clone, 69A (FIG. 9), whose 5' terminus has an EcoRI site that is present in the coding sequence of APLP1 and is the result of an EcoRI site that escaped methylation during construction of the cDNA library.

Although screening of the cDNA libraries with probes derived from the 5' end of 69A failed to identify any more APLP1 clones, the use of a variation of the RACE procedure developed by Frohman et al. (Frohman et al., *Proc. Natl. Acad. Sci. U.S.A.* 85:8998–9002 (1988)) and by Ohara et al. (Ohara et al., *Proc. Natl. Acad. Sci. U.S.A.* 86:5673–5677 (1989)) did enable the isolation of several independent, overlapping cDNA clones that extend the APP homology past the 5' EcoRI site of 69A. The longest clone, J (FIG. 1), did not contain an initiator methionine.

The sequence information obtained via the RACE procedure was used to create PCR primers and amplify the 5'-most 100 base pairs encoded by clone J. This PCR product was used as a probe in a screen of a Stratagene mouse brain cDNA library that successfully identified a number of full length APLP1 clones. Two of these were sequenced to obtain the final 313 5' nucleotides as well as the polyadenylation signal and the poly A tail of the APLP1 cDNA. The predicted initiator methionine is in agreement with the eukaryotic consensus initiation sequence (Kozak, M., *Nucl. Acids Res.* 12:857–872 (1984).

APLP1 is Related to APP

The 2361 nucleotides of the cDNA sequence encode an open reading frame of 653 amino acids as is shown in FIG. 10 (SEQ ID NO:16). The protein is predicted to have a short intracellular C-terminus of 46 amino acids, a membrane spanning domain of 23 amino acids, and a larger extracellular N-terminus. The predicted amino acid sequence and the overall structure of APLP1 is similar to those of APP, which resembles an integral membrane protein (Kang et al., *Nature* 325:733–736 (1987)). The alignment of the two amino acid sequences that is shown in FIG. 11 (SEQ ID NOS:17–18) reveals that overall APLP is 42% identical and 64% similar to APP.

APLP1 is a Member of a Family of APP-like Proteins

The identities between APLP1 and APP are concentrated in three distinct regions (FIG. 12 (SEQ ID NOS:19–28)), where the proteins are 47, 54 and 56% identical and 67, 73 and 74 % similar. These same three regions have been shown previously to be shared between APP and a Drosophila APP-like protein (Drosophila APPL), and have been termed the extracellular I (EI), extracellular II (Eli) and cytoplasmic (C) domains by these investigators (Rosen et al., *Proc. Natl. Acad. Sci. U.S.A.* 86:2478–2482 (1989)). The cytoplasmic domain homology is also present in a partial cDNA clone that has been isolated from a rat testis library (Yan et al., *Proc. Natl. Acad. Sci. U.S.A.* 87:2405–2408 (1990)). Only APP contains the βA4 sequence that is found in amyloid plaques.

FIG. 12 (SEQ ID NOS:19–28) shows the domain alignment of the four proteins mentioned above. A similar alignment has been shown for the relationship between the Drosophila APPL1 and APP (Rosen et al., *Proc. Natl. Acad. Sci. U.S.A.* 86:2478–2482 (1989)). The testis cDNA is included only in the C domain comparison since only this portion of the predicted amino acid sequence is known (Yan et al., *Proc. Natl. Acad. Sci. U.S.A.* 87:2405–2408 (1990)). EI begins at amino acid 21 in the APLP1 open reading frame and spans 136 amino acids. Overall, 102 of these 136 amino acids (75%) are either identical to amino acids in the respective positions of APP or Drosophila APPL, or they are the same in all three proteins. The most striking conservation within this region is that of 12 cysteine residues in all three of the sequences. There are also two regions of amino acids that are particularly well conserved (underlined in FIG. 12 (SEQ ID NOS:19–28)), as is an unusually acidic region composed of glutamic and/or aspartic acids that spans amino acids 237–271 in the APLP1 sequence (FIG. 10) (SEQ ID NO:16)).

EII spans 130 amino acids in the mouse APLP1 sequence. 93 of the 130 APLP1 amino acids (71%) are identical to either one or both of their counterparts in APP or the Drosophila APPL sequences. This region also contains conserved N-glycosylation site in all 3 proteins.

The third domain encompasses the C-terminal cytoplasmic region of all of the proteins, including the predicted amino acid sequence of the rat testis cDNA. The conservation of amino acids among the members of the APP-like family within this domain is particularly strong. Although the four proteins do not share homology within the predicted transmembrane domains (FIG. 11 (SEQ ID NOS:17–18), Rosen et al., *Proc. Natl. Acad. Sci. U.S.A.* 86:2478–2482 (1989); Yan et al., *Proc. Natl. Acad. Sci. U.S.A.* 87:2405–2408 (1990)), all of them do contain a 3–4 amino acid span of charged residues (arginine/lysine) at the cytoplasmic face of the membrane (FIG. 12 (SEQ ID NOS:19–28)). This characteristic is often seen at the membrane-cytoplasmic junction of other proteins, and has been hypothesized to allow for an interaction with phospholipids in the membrane, or to provide a stop transfer signal for membrane bound proteins (Blobel, G., *Proc. Natl. Acad. Sci. U.S.A.* 77:1796–1500 (1980)).

Northern Blot Analysis

Figure 13:
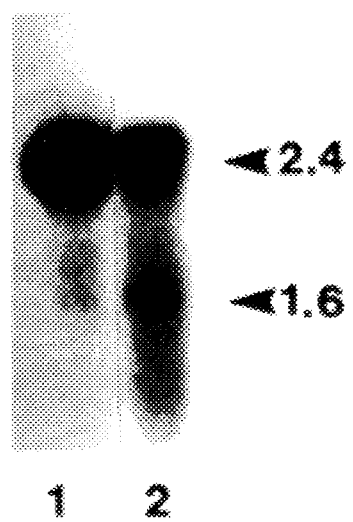
FIG. 13. Northern blots of mouse brain and neuroblastoma RNA. Poly A+ RNA (10 μg) from neuroblastoma (lane 1) and mouse brain (lane 2) was separated on agarose gels containing formaldehyde and transferred to nylon as described in Materials and Methods. The blot was probed with DNA corresponding to nucleotides 1482–1995 of the nucleotide sequence shown in FIG. 10 (SEQ ID NO:15). Sizes of hybridizing messages in kb are indicated.

FIG. 13 shows autoradiographs of Northern blots containing polyA+ RNA from mouse brain and neuroblastoma cells that were probed with DNA corresponding to nucleotides 1791–2305 of FIG. 10 (SEQ ID NO:15). These blots reveal that in mouse brain and neuroblastoma cells there are two messages of approximately 2.4 and 1.6 kb that hybridize to this probe. The larger message appears to be present in relatively greater abundance than the smaller message. Because of its size, it is clear that the cDNA that corresponds to the 2.4 kb message, although both messages are consistently seen in Northerns that are probed and washed under stringent conditions. The mouse APLP1 cDNA does not hybridize to the 3.2 and 3.4 kb APP messages under the conditions used (see Materials and Methods; Kang, J. et al., *Nature* 325:733–736 (1987)).

Generation of Antibodies Against an APLH Peptide

In order to further characterize the protein encoded by the APLP1 cDNA, antibodies were raised to a synthetic peptide which corresponds to a unique sequence of mouse APLP1. The peptide that was used as antigen corresponds to a 9 amino acid segment located near the C-terminus of the APLP1 protein (QQLRELQRH) (SEQ ID NO:1), a region where the four proteins are not homologous.

Figure 14A:
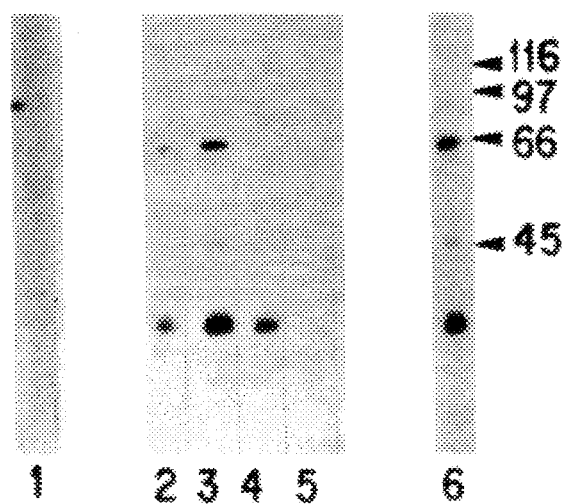
FIGS. 14A–C. Western Blots using antiserum 301 (See the Example). Mouse brain and neuroblastoma proteins were separated by 7.5 % PAGE as described in Materials and Methods.
Figure 14B:
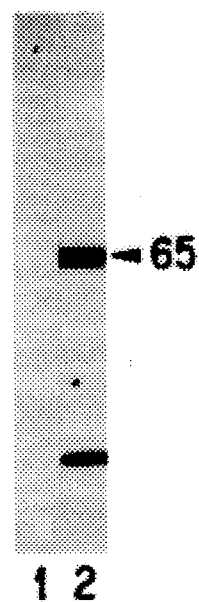

Four rabbits were injected with the peptide as described in Materials and Methods. Two of the four rabbits (301 and 302) produced sera that strongly recognize a 65 kDa mouse brain protein that is not recognized by the appropriate preimmune sera (FIG. 14A). A smaller protein of approximately 33 kDa that is recognized by antiserum 301 may be a proteolytic degradation product of the larger protein. In FIG. 14A, the specificity of the interaction of the antibody with these proteins is demonstrated by the ability to block the binding of antibody 301 to the proteins by preabsorbing with the original peptide (lanes 2–5); an irrelevant peptide has no effect on the interaction of the antibody with either the 65 kDa or 33 kDa protein (lane 6). Antiserum 301 also recognizes a 65 kDa protein present in neuroblastoma cell extracts that is not recognized by preimmune serum (FIG. 14B).

Figure 14C:
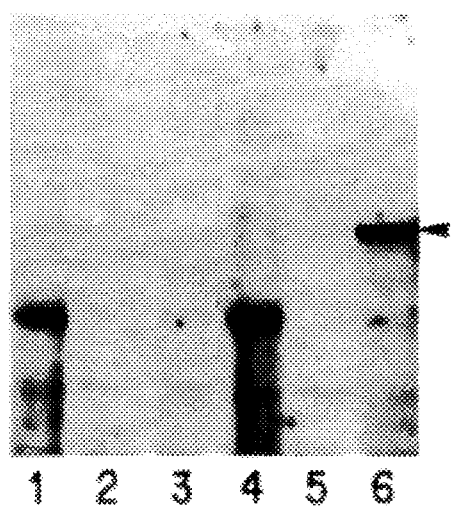

To further confirm the specificity of the 301 antiserum, we determined whether the antiserum would recognize a β-galactosidase fusion protein containing the 222 carboxy-terminal amino acids encoded by the APLP1 cDNA. FIG. 14C shows a Western blot of bacterially produced proteins that were probed with antiserum 301. As can be seen in lane 6 of this figure, antisera 301 does specifically interact with the β-galactidase-APLP1 fusion protein.

There are a number of antibodies that have been generated against the C-terminus of APP. Because the identity between APP and the mouse APLP1 in this region is particularly strong, some of these antisera would also be likely to interact with the mouse APLP1. One of these antisera, R37 (Kang et al., *Nature* 325:733–736 (1987); and Ishii et al., *Neuropatolo. and Appl. Neurobiol.* 15:135–147 (1989)), is directed against the carboxy-terminal 15 amino acids of APP, a region where the two proteins are particularly similar (see FIG. 12 (SEQ ID NOS:19–28)). R37 does recognize the β-galactosidase-APLP1 fusion protein and a 65 kDa mouse brain protein that comigrates with the 65 kDa protein recognized by antiserum 301 (data not shown). The 15 amino acid sequence used to raise the anti-APP antibody does not overlap the 9 amino acids used to generate antiserum 301. These data suggest that the 65 kDa protein contains two epitopes in common with the APLP1 fusion protein. Antibodies can be made which recognize only APLP1.

Anti-APLP1 Antisera Recognizes a Protein in the Golgi

Figure 15A:
Figure 15B:
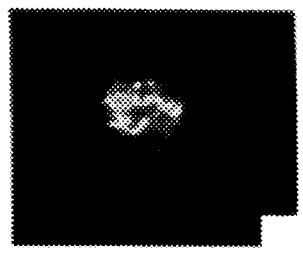
Figure 15C:
Figure 15D:
Figure 15E:

The subcellular localization of the protein recognized by antiserum 301 was assayed by immunofluorescence. When neuroblastoma cells are stained with 301, the pattern that is observed is a reticular staining near the nucleus (FIG. 15A,B). Because of 3-dimensional nature of the staining, and the round shape of the cells, the image seen in any one plane of focus appears punctate rather than reticular. An identical pattern is seen with antiserum 302 (data not shown). The pattern itself is reminiscent of Golgi staining, and when these cells are stained with an antibody to a known Golgi enzyme, mannosidase II, a pattern much like that seen with antiserum 301 is observed (FIG. 15C). The inclusion of the original peptide in the antibody incubation inhibited the 301 staining (FIG. 15D). Staining was not seen when preimmune serum was used (FIG. 15E).

Discussion

The present APLP1 cDNA sequence encodes a new member of the APP-like family. The mouse homologue of the human amyloid precursor protein has been cloned previously and is 96.8% identical to the human sequence at the amino acid level (Yamada et al., *Biochem. Biophys. Res. Comm.* 158:906–912 (1987)). Thus, the present APLP1 cDNA, which is 42% identical to the amyloid precursor protein at the amino acid level, is not the mouse homologue of APP and is a distinct, yet related protein.

The two sequences share three domains of homology. The amino acid conservation within these domains include 12 cysteines, an unusually acidic region, a potential N-glycosylation site, a hydrophobic membrane spanning region, and several specific blocks of exact identity. It is clear that the mouse APLP, the Drosophila APPL, the rat testis protein and APP comprise a family of proteins. The extensive conservation of amino acid identity as well as both the overall and specific domain structure within this family of proteins suggests that these proteins share a common function.

There are two potentially interesting observations that can be made concerning the strict conservation of the 7-amino acid sequence located within the cytoplasmic tail of the proteins in the APP-like family (see underlined sequence in the appropriate portion of FIG. 12 (SEQ ID NOS:19–28)). There is a potential tyrosine phosphorylation site present 8–9 amino acids from the carboxy terminus of all four sequences (Tamkun et al., *Cell* 46:271–282 (1986)). APP can be phosphorylated when introduced into transformed embryonic kidney cells (Oltersdorf et al., *J. Biol. Chem.* 265:4492–4497 (1990)) and a peptide containing a portion of the cytoplasmic domain can be phosphorylated on serine and threonine residues in vitro (Candy et al., *Proc. Natl. Acad. Sci. U.S.A.* 85:6218–6221 (1988)), but tyrosine phosphorylation has not yet been demonstrated. Agents that are known to regulate protein phosphorylation appear to affect the rate of proteolytic processing of mature forms of APP (Buxbaum et al., *Proc. Natl. Acad. Sci. U.S.A.* 87:6003–6006 (1990)), suggesting that abnormal protein phosphorylation may be involved in the production of βA4. The sequence surrounding this tyrosine also shares homology with the only tyrosine in the a-helical domain that is conserved between several classes of intermediate filaments (Lendahl et al., *Cell* 60:585–595 (1990)). The conservation of this potentially phosphorylated tyrosine is intriguing in light of the role that tyrosine phosphorylation is known to play in the regulation of cell growth and differentiation.

The same tyrosine is part of the tetrameric sequence NPxY that is believed to be required for the ligand-independent, coated pit-mediated internalization of the low density lipoprotein receptor (Chen, et al., *J. Biol. Chem.* 265:3116–3123 (1990)). The NPxY sequence is present in the cytoplasmic tails of at least 16 other cell surface receptor molecules -including the β-integrin receptor and members of the EGF receptor family (Chen, et al., *J. Biol. Chem.* 265:3116–3123 (1990)).

The APLP1 cDNA that has been isolated shares at least one epitope with a 65 kDa protein that is present in mouse brain homogenates and neuroblastoma cell extracts, and it shares an epitope with a protein that localizes to the Golgi in neuroblastoma cells. An antiserum that recognizes the Drosophila APPL protein also recognizes a protein in the Golgi (Luo et al., *J. Neurosci* 10:3849–3861 (1990)). In addition, antibodies to the APP give a perinuclear staining pattern suggestive of either Golgi or ER localization when used for immunofluorescence on muscle fibers (Zimmermann et al., *EMBO J.* 7:367–372 (1988)). The N-terminal extracellular portion of both the Drosophila APPL protein and APP can be secreted via cleavage at or near the membrane (Weidman et al., *Cell* 57:115–126 (1989); Zimmermann et al., *EMBO J.* 7:367–372 (1988); and Palmert et al., *Proc. Natl. Acad. Sci. U.S.A.* 86:6338–6342 (1989)). Although the normal function of the proteins in the APP family remains cryptic, the present results suggest that APLP1, like APP and the Drosophila APPL may be processed in, or reside in, the Golgi.

The existence of a family of APP-like proteins implies that these proteins may share a function. The conservation of cysteines at the N-termini is indicative of conserved tertiary and/or quaternary structure, and suggests that these molecules may interact with a common extracellular molecule. Likewise the strong amino acid conservation within the intracellular C-termini suggests that the proteins in this family may interact with a common molecule inside of the cell. A distinct physiological role for APP has yet to be determined. Clues to the function of any of the members of the APP-like family of proteins should help to elucidate the normal function and processing and regulation of APP.

EXAMPLE 3

Mapping the Human Chromosomal Locus Encoding APLP1

Portions of the mouse brain cDNA and a 1.8 kb partial cDNA isolated from a human brain cDNA library were used to map the human chromosomal locus encoding APLP1. To determine the best restriction digest for the selective identification of the human chromosomal APLP1 fragments, human, mouse and hamster genomic DNAs were analyzed by Southern blot hybridization using the partial human cDNA clone following digestion with EcoRI, HindIII, PstI, and TaqI. EcoRI was chosen for further analysis since it produced human DNA fragments (approximately 8 kb and 3.3 kb, data not shown) that were clearly discernable from the rodent. A panel of DNAs from 31 human-rodent somatic cell lines (Geissler et al., *Somat. Cell Mol. Genet.* 17:197–214 (1991)) of known karyotype was digested with EcoRI. These DNAs were then probed with the human APLP1 cDNA clone and the hybridization pattern was consistent with the assignment of the APLP1 locus to chromosome 19.

To determine the regional position of APLP1 locus on chromosome 19, the full-length mouse brain APLP1 cDNA was hybridized to EcoRI-digested genomic DNA from a number of somatic cell hybrids containing only human chromosome 19 or specific fragments of this autosome as well as other chromosomes (G35CCB, G35F3B, GM89A99c7B, G24B2AM, FONIA4, TVB1D, 1016A and 5HL94; FIG. 16). All of these hybrid lines, with the exception of GM89A99c7B, contain the two human specific APLP1 bands. GM89A99c7B contains the reciprocal part of the X: 19 translocation occurring in 908K1, G35F3 and G35FCC (FIG. 16). These results exclude the APLP1 locus from the short arm of chromosome 19 and place it between 19q13.2 and the centromere.

Discussion

While no physiological role has been determined for APLP1, its map location is interesting in view of its potential relationship to Alzheimer's disease (AD). The chief component of Alzheimer-associated amyloid is the 39–43 amino acid βA4 peptide which is derived from the larger amyloid precursor protein (APP) encoded by a gene on chromosome 21 (Kang et al., Nature 325:733–736 (1987); Robakis et al., Proc. Natl. Acad. Sci. U.S.A. 84:4190–4194 (1987); Tanzi et al., Science 235:880–884 (1987)). The gene defect for an early-onset (>65 years of age) form of familial Alzheimer's disease (FAD) has been mapped to chromosome 21 (St. George-Hyslop et al., Science 235:885–889 (1987)) and a small percentage (<3 %) of FAD appears to be caused by mutations within the APP gene (Chartier-Harlin et al., Nature 353:884–846 (1991); Goate et al., Nature 349:704–706 (1991); Murrell et al., Science 254:97–99 (1991)). Genetic heterogeneity has also been reported for FAD (St. George-Hyslop et al., Nature 347:194–197 (1990)) and a set of late-onset (>65 years of age) FAD pedigrees have recently demonstrated linkage to chromosome 19 (Pericak-Vance et al., Am. J. Hum. Genet. 48:1034–1050 (1991)). Because of the regional chromosomal localization of APLP1 to the proximal portion of 19q and the significant homology of this gene to APP, APLP1 is a candidate for the gene defect responsible for a late-onset form of FAD.

EXAMPLE 4

Isolation and Characterization of the Human APLP2 Gene Encoding a Homologue of the Alzheimer's Associated Amyloid B Protein Precursor In an attempt to isolate other members of the APP protein family, the mouse APLP1 sequence was first used to scan the Genbank database for homologous sequences. In addition to obtaining matches for APP, APPL, and the partial cDNA from rate testes, a match with an anonymous 274 base pair human brain cDNA entry (Genbank accession number M78104), was noted. This match, which was significant but not identical to mouse APLP1 (63% identity), indicated that M78104 was a small piece of a cDNA encoding a second APLP. In order to characterize the APP-like gene family in more detail, full length cDNAs for this second APLP, APLP2, were isolated. The isolation and characterization of APLP2 cDNA clones from human brain, provide further support for the hypothesis that APP is a member of a highly conserved gene family.

A human brain frontal cortex Lambda Zap II cDNA library (Stratagene) was screened with a probe consisting of a PCR product generated with primers designed to amplify a portion of the 274 base pair partial cDNA sequence identified in Genbank. To prepare the probe, a primer set (5'GCAACCGAATGGACAGGGTA 3' (SEQ ID NO:11) and 5'CAAGGCAGCCA GGTAGTTCTC 3' (SEQ ID NO:12); see FIG. 17) was used to amplify a 232 base pair product from a human occipital cortex cDNA library. The PCR product was sequenced to confirm its identity and an internal primer set (5'GTAAAGAAGGAATGGGAA GAGGC3' (SEQ ID NO:13) and 5'CCATCCGACGGC GGTCATTCAGC3'(SEQ ID NO:14); see FIG. 17) was designed and used to amplify a 185 base pair PCR fragment (SG190) that was used for the human brain library screen. Screening, purification and sequencing of the SG190-positive clones, including a full length cDNA were carried out according to standard conditions (Wasco et al., Proc. Natl. Acad. Sci. U.S.A. 89:10758–10762 (1992)).

Human APLP2 is encoded by a 706 amino acid sequence that is similar to APP and APLP1 in overall structure as well as amino acid sequence. APLP2 is 52% identical, 69% similar to APP695 (FIG. 17 (SEQ ID NOS:29–30)) and 43 % identical, 63 % similar to APLP1. Virtually all of the identified domains and motifs that characterize APP, APPL and APLP1 are present in APLP2. Specifically, an N-terminal cysteine-rich region (consisting of 12 cysteines), a novel zinc-binding motif (Bush et al., Neurobiol. Aging 13 (supplement 1):A.331 (1992)), an acidic-rich domain, N-glycosylation sites, a hydrophobic membrane spanning domain and a cytoplasmic domain containing a clathrin binding motif and potential serine/threonine, casine kinase I, II and tyrosine phosphorylation sites are conserved in APLP2 (FIG. 17). FIG. 18 (SEQ ID NOS:31–33) shows the amino acids that are identical or conservatively substituted in APLP2, APP and APLP1 demonstrating the extremely high degree of conservation among these proteins. Some of these stretches of homologous amino acids shown in FIG. 18 (SEQ ID NOS:31–33) may contain potential consensus motifs that are germane to the function of this protein family.

Chromosomal Location of APLP2 Gene

To determine the chromosomal location of the APLP2 gene, a cDNA probe was hybridized to a filter containing Hind III-digested DNA from a panel of 43 human-rodent somatic cell hybrid lines containing either individual or specific sets of human chromosomes (Pelletier et al., Genomics 10:1079–1082 (1991); Geissler et al., Som Cell Gen 17:207–214 (1991)). The probe detected specific human APLP2 bands in somatic cell hybrid lines consistent with the assignment of the APLP2 gene locus to human chromosome 11. Specifically, a positive signal for human APLP2 was obtained in a somatic cell hybrid line containing DNA from chromosome 11 as its only human material, and in a hybrid containing chromosome 11 and three other human chromosomes.

During the sequencing of the human APLP2 cDNA clones, a single alternatively spliced form containing an exon encoding a 12 amino acid stretch was identified indicating that like APP, APLP2 is alternatively transcribed (FIG. 17). Although a portion of the APLP2 cDNA isolated from mouse embryo contained a KPI domain similar to that in APP, a form of adult human APLP2 that contains such a domain has not yet been detected.

Northern Blot Analysis

Northern blot analysis of fetal peripheral tissue and adult brain regions demonstrated that the APLP2 message is approximately 4 kb in size (FIG. 19). Lighter bands at approximately 3 kb and 2 kb may represent cross-hybridizing messages from other members of the APP/APLP family, or as of yet unisolated APLP2 alternative transcripts. The APLP2 transcript was detected at varying levels in all peripheral and central nervous system tissues tested and displayed a level and pattern of expression that is extremely similar to that of APP (FIG. 19A). Both transcripts are expressed in relatively abundant amounts in brain, heart, and kidney and at lower levels in liver and thymus. However, in contrast to APP, APLP2 is expressed at relatively high levels in the small intestine and lung.

To determine the distribution of APLP2 transcript in the adult human brain Northern blot analysis was carried out on mRNA from 11 different brain regions (FIG. 19B). This same blot had been previously hybridized to APP thus allowing a direct comparison of expression of the two genes (Tanzi et al., Science 235:880–884 (1987); Tanzi et al., Nature 331:528–530 (1988)). The levels of APLP2 mRNA were highest in the temporal association cortex (A20, Tanzi et al., Nature 331:528–530 (1988)), the posterior perisylvian cortex-supramarginal gyri (A40), the anterior perisylvian cortex-opercular gyri (A44) and frontal pole of the cortex (A10). These regions which are particularly affected in the brains of AD patients, normally contain a relatively large amount of APP RNA. Moderate hybridization was detected in the cerebellar cortex and the caudate-putamen. Relatively weaker hybridization was seen in the striate, extrastriate, and motor cortices (A17, A18 and A4), the hippocampus, and the thalamus. Overall, APLP2 reveals a pattern of expression that is very similar to that of APP (FIG. 19B; Tanzi et al., *Science* 235:880–884 (1987); Tanzi et al., *Nature* 331:528–530 (1988)), although, some differences were noted. For example, APLP2 is expressed at relatively higher levels than APP in thalamus, while APP expression is greater than that of APLP2 in Brodman area A40.

FIG. 20 shows the result of Northern blot hybridization of APLP2 and APP cDNA probes to RNA derived from normal and fetal brains with Down syndrome (DS), and from normal and adult brains with AD. Although APP expression is higher in the DS samples, APLP2 expression is not significantly changed. This result is not unexpected given the extra copy of chromosome 21 present in DS patients. APP expression is slightly lower in AD versus normal adult cerebellum, and is dramatically decreased in AD frontal cortex relative to normal (FIG. 20). This decrease in APP expression is probably a reflection of AD-related neuronal loss in these areas which is particularly enhanced in the frontal cortex. Surprisingly, it has presently been found that although APP expression is somewhat decreased in AD cerebellum compound to normal, APLP2 expression is clearly increased in this same AD cerebellum sample (FIG. 20). One possibility is that this may reflect a compensatory increase in APLP2 expression in response to lower levels of APP. It is equally conceivable that increased expression of APLP2 preceded the decrease in APP message.

The present inventors have discovered that APLPs may compete with APP for factors involved with maturation and processing (Wasco et al., *Proc. Natl. Acad. Sci. U.S.A.* 89:10758–10762 (1992)). This would require that the two proteins are produced and processed within the same cell populations. To address this issue, non isotopic in situ hybridization studies designed to localize APLP2 mRNA transcripts within the hippocampal formation, a region that is severely affected in AD, have been employed. It was found that the mRNA for APLP2 is contained in both the cell soma and, to some extent, neuronal processes of pyramidal neurons in the hippocampal formation (FIG. 21). Much less hybridization was observed in smaller interneurons, glial cells, and endothelial cells. The subcellular localization is similar to that seen for APP and APLP1 messages using the same in situ hybridization procedure (Tanzi et al., *Mol. Brain Res.*:in press; Hyman et al., *Mol. Brain Res.*:in press; Wasco et al., *Alzheimer's disease and related disorders* 1992:selected communications (in press)). Moreover, the cellular specificity and regional distribution of the APLP messages are also extremely similar to those of APP indicating that the APP and APLPs are located within the same sets of neurons in the hippocampal formation.

Based on the overall conservation of amino acid sequence and domain structure within the APP gene family, these proteins may share common functions and, perhaps be processed similarly (Wasco et al., *Proc. Natl. Acad. Sci. U.S.A.* 89:10758–10762 (1992)). Recent data further indicate that APLP2 and APP undergo similar processing (unpublished data). Antibodies to APP, APLP1 and APPL recognize proteins in the Golgi (Wasco et al., *Proc. Natl. Acad. Sci. U.S.A.* 89:10758–10762 (1992); Zimmermann et al., *EMBO J.* 7:367–372 (1988); Palacios et al., *Mol. Brain Res.* 15:195–206 (1992); Luo et al., *J. Neurosci.* 10:3849–3861 (1990)). Likewise, APLP2 appears to be associated with the Golgi apparatus unpublished data. This suggests that maturation of these proteins in the Golgi very likely involves interaction with common factors. The apparent similarities in the processing and maturation of APP and APLP2 raises the possibility that altered expression of APLP2 or other APLPs could affect the post-translational modification and metabolism of APP in cells where these genes are co-expressed. If APLP2 or other APLPs were to interfere with the proper maturation (e.g. N- or O-glycosylation) of APP, APP could be rerouted into alternative pathways including those predisposed to amyloid formation. Along these same lines, if the metabolic machinery responsible for processing APP were overburdened with members of the APLP family, altered metabolism of APP may occur, perhaps resulting in increased production of amyloidogenic fragments. Therefore, although the APLP2 and APLP1 do not contain an A$\beta$ domain, they may still ultimately affect the maturation and/or metabolism of APP.

It will be appreciated to those skilled in the art that the invention can be performed within a wide range of equivalent parameters of composition, concentrations, modes of administration, and conditions without departing from the spirit or scope of the invention or any embodiment thereof.

The disclosures of all references, patent applications and patents recited herein are hereby incorporated by reference.

What is claimed is:

1. A method for activating transcription from an amyloid β-protein precursor (APP) promoter operably linked to a nucleic acid molecule encoding a polypeptide, comprising:
   providing upstream stimulatory factor (USF) to said APP promoter at levels exceeding basal cellular levels whereby transcription from the APP promoter is activated.

2. The method of claim 1, wherein said USF is provided exogenously.

3. The method of claim 1, wherein the APP promoter is operably linked to a nucleic acid sequence encoding APP.

4. The method of claim 1, wherein the APP promoter is operably linked to a nucleic acid sequence encoding a reporter protein.

5. The method of claim 4, wherein said reporter protein is the luciferase reporter protein.

6. The method of claim 1, wherein transcription from the APP promoter is detected by primer extension analysis of the resulting transcript.

7. The method of claim 1, wherein transcription is activated by transfecting a cell containing the APP promoter with a DNA or RNA construct which expresses USF.

8. The method of claim 1, wherein said USF binds to the AP-1/AP-4 site present in the APP promoter.

9. A method for down-regulating transcription from an amyloid β-protein precursor (APP) promoter operably linked to a nucleic acid molecule encoding a protein, comprising:
   contacting USF with a USF-binding compound which interferes with USF binding to the APP promoter whereby transcription from the APP promoter is down-regulated.

10. The method of claim 9, wherein said USF binding compound is selected from an APLP, APP, or a nucleic acid sequence comprising the USF consensus binding sequence.

11. The method of claim 10, wherein said USF binding compound is an APLP selected from APLP-1 or APLP-2.

12. The method of claim 11, wherein transcription is down-regulated by transfecting a cell containing the APP promoter with a DNA or RNA construct which expresses said APLP protein.

13. The method of claim 9, wherein the APP promoter is operably linked to a nucleic acid sequence encoding APP.

14. The method of claim 9, wherein the APP promoter is operably linked to a reporter protein.

15. A method for screening candidate upstream stimulatory factor (USF) binding compounds to identify compounds which down-regulate transcription from the amyloid β-protein precursor (APP) promoter, comprising the steps of:

(a) transfecting a host cell with a DNA or RNA construct containing the APP promoter operably linked to a gene encoding a reporter protein;

(b) transfecting said host cell with a DNA or RNA construct which expresses upstream stimulatory factor (USF) protein;

(c) measuring reporter protein expression activated by USF binding to the APP promoter;

(d) transfecting said host cell with a DNA or RNA construct either containing or which expresses a USF binding compound; and (e) measuring if a decrease in reporter protein expression occurs due to said USF binding compound interfering with USF binding to the APP promoter.

16. The method of claim 15, wherein said gene encoding a reporter protein encodes a luciferase reporter protein.

17. The method of claim 15, wherein said USF binding compound is an APLP.

18. The method of claim 17, wherein said APLP is selected from APLP-1 or APLP-2.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:1:

Gln  Gln  Leu  Arg  Glu  Leu  Gln  Arg  His
    1                    5

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGGCCGGATC AGCTGACTCG CCTGGCTCT                    29

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCTCAGATCT CGAGCTCGGT AC                           22

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCTTACTGTC AGCTGACTCG CCTGGCTCT                    29

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGGCCGGAAT CGTGCTGTCG CCTGGCTCT                    29

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGGCCGGATC AGCTGACGAT ACCTGTCCG                    29

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GATCCAGCTG ACTCATCACT AG                           22

( 2 ) INFORMATION FOR SEQ ID NO:8:

( i ) SEQUENCE CHARACTERISTICS:
        ( A ) LENGTH: 28 base pairs ( B ) TYPE: nucleic acid
( C ) STRANDEDNESS: single
( D ) TOPOLOGY: linear ( x i ) SEQUENCE DESCRIPTION: SEQ ID NO:8:

GATCACCAGC TGTGGAATGT GTGTGATC                                                    28

( 2 ) INFORMATION FOR SEQ ID NO:9:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:9:

GGGCCGGATC ACGTGACTCG CCTGGCTCT                                                   29

( 2 ) INFORMATION FOR SEQ ID NO:10:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:10:

GGAAATATAG AAGAAGGAG                                                              19

( 2 ) INFORMATION FOR SEQ ID NO:11:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:11:

GCAACCGAAT GGACAGGGTA                                                             20

( 2 ) INFORMATION FOR SEQ ID NO:12:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:12:

CAAGGCAGCC AGGTAGTTCT C                                                           21

( 2 ) INFORMATION FOR SEQ ID NO:13:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:13:

GTAAAGAAGG AATGGGAAGA GGC                                                         23

( 2 ) INFORMATION FOR SEQ ID NO:14:

( i ) SEQUENCE CHARACTERISTICS:
      ( A ) LENGTH: 23 base pairs
      ( B ) TYPE: nucleic acid
      ( C ) STRANDEDNESS: single ( D ) TOPOLOGY: linear ( x i ) SEQUENCE DESCRIPTION: SEQ ID NO:14:

CCATCCGACG GCGGTCATTC AGC 23

( 2 ) INFORMATION FOR SEQ ID NO:15:

( i ) SEQUENCE CHARACTERISTICS:
        ( A ) LENGTH: 2358 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 88..2046

( x i ) SEQUENCE DESCRIPTION: SEQ ID NO:15:

```
CGGCACGAGG  TGGCGCTGGG  AGCTCCTGTC  ACCGCTGGGG  CCGGGTAGGG  GCGGGCGGGA                60

GCGCAGGGAC  GTGAGGGCCG  AGCGGAC ATG GGG CCC ACC AGC CCC GCC GCT                       111
                                Met Gly Pro Thr Ser Pro Ala Ala
                                 1               5

CGC GGT CAG GGT CGC CGC TGG CGA CCG CCG CTG CCG CTG TTG CTG CCA                       159
Arg Gly Gln Gly Arg Arg Trp Arg Pro Pro Leu Pro Leu Leu Leu Pro
     10              15                  20

CTG TCA TTG CTG CTT CTG CGC GCG CAG CTC GCC GTC GGG AAC CTG GCT                       207
Leu Ser Leu Leu Leu Leu Arg Ala Gln Leu Ala Val Gly Asn Leu Ala
 25              30                  35                      40

GTT GGG AGC CCC AGC GCG GCC GAG GCT CCG GGG TCG GCT CAA GTG GCT                       255
Val Gly Ser Pro Ser Ala Ala Glu Ala Pro Gly Ser Ala Gln Val Ala
                 45                  50                  55

GGA CTA TGT GGG CGT CTA ACC CTT CAC CGG GAC TTG CGC ACC GGC CGC                       303
Gly Leu Cys Gly Arg Leu Thr Leu His Arg Asp Leu Arg Thr Gly Arg
             60                  65                  70

TGG GAA CCA GAC CCA CAG CGA TCA CGA CGC TGT CTT CTG GAC CCG CAG                       351
Trp Glu Pro Asp Pro Gln Arg Ser Arg Arg Cys Leu Leu Asp Pro Gln
         75                  80                  85

CGC GTG CTG GAG TAC TGC AGA CAG ATG TAC CCC GAG CTG CAC ATA GCA                       399
Arg Val Leu Glu Tyr Cys Arg Gln Met Tyr Pro Glu Leu His Ile Ala
     90                  95                 100

CGC GTG GAG CAG GCT GCA CAG GCC ATC CCG ATG GAG CGC TGG TGT GGG                       447
Arg Val Glu Gln Ala Ala Gln Ala Ile Pro Met Glu Arg Trp Cys Gly
105                 110                 115                 120

GGT ACC CGG AGT GGC AGA TGC GCC CAC CCC CAC CAT GAG GTT GTG CCC                       495
Gly Thr Arg Ser Gly Arg Cys Ala His Pro His His Glu Val Val Pro
                125                 130                 135

TTC CAT TGC CTG CCT GGC GAA TTC GTG AGT GAA GCC CTA GTG CCC                           543
Phe His Cys Leu Pro Gly Glu Phe Val Ser Glu Ala Leu Leu Val Pro
            140                 145                 150

GAA GGC TGT CGG TTC TTG CAC CAG GAG CGT ATG GAC CAG TGT GAG AGT                       591
Glu Gly Cys Arg Phe Leu His Gln Glu Arg Met Asp Gln Cys Glu Ser
        155                 160                 165

TCA ACC AGG AGG CAT CAG GAG GCT CAG GAG GCC TGC AGC TCT CAG GGC                       639
Ser Thr Arg Arg His Gln Glu Ala Gln Glu Ala Cys Ser Ser Gln Gly
    170                 175                 180

CTC ATC CTG CAC GGC TCT GGC ATG CTT TTG CCC TGT GGC TCT GAT CGG                       687
Leu Ile Leu His Gly Ser Gly Met Leu Leu Pro Cys Gly Ser Asp Arg
185                 190                 195                 200

TTC CGA GGT GTG GAG TAT GTA TGC TGT CCA CCT CCC GCA ACT CCC AAC                       735
Phe Arg Gly Val Glu Tyr Val Cys Cys Pro Pro Pro Ala Thr Pro Asn
                205                 210                 215
```

| | | | | | | | | | | | | | | | | |
|---|---|---|---|---|---|---|---|---|---|---|---|---|---|---|---|---|
| CCA | TCT | GGG | ATG | GCA | GCT | GGT | GAC | CCC | TCT | ACC | CGG | TCC | TGG | CCC | CTG | 783 |
| Pro | Ser | Gly | Met | Ala | Ala | Gly | Asp | Pro | Ser | Thr | Arg | Ser | Trp | Pro | Leu | |
| | | | 220 | | | | | 225 | | | | | 230 | | | |
| GGG | GGC | AGA | GCA | GAG | GGA | GGT | GAG | GAT | GAA | GAG | GAG | GTG | GAA | TCT | TTC | 831 |
| Gly | Gly | Arg | Ala | Glu | Gly | Gly | Glu | Asp | Glu | Glu | Glu | Val | Glu | Ser | Phe | |
| | | 235 | | | | | 240 | | | | | 245 | | | | |
| CCT | CAG | CCA | GTA | GAC | GAT | TAC | TTC | GTA | GAG | CCC | CCT | CAG | GCT | GAA | GAA | 879 |
| Pro | Gln | Pro | Val | Asp | Asp | Tyr | Phe | Val | Glu | Pro | Pro | Gln | Ala | Glu | Glu | |
| | | 250 | | | | | 255 | | | | | 260 | | | | |
| GAA | GAG | GAA | GAG | GAG | GAA | GAA | AGG | GCC | CCA | CCT | CCC | AGC | TCC | CAC | ACC | 927 |
| Glu | Glu | Glu | Glu | Glu | Glu | Glu | Arg | Ala | Pro | Pro | Pro | Ser | Ser | His | Thr | |
| 265 | | | | | 270 | | | | | 275 | | | | | 280 | |
| CCT | GTC | ATG | GTT | AGC | AGA | GTC | ACT | CCC | ACC | CCA | AGG | CCT | ACT | GAT | GGT | 975 |
| Pro | Val | Met | Val | Ser | Arg | Val | Thr | Pro | Thr | Pro | Arg | Pro | Thr | Asp | Gly | |
| | | | | 285 | | | | | 290 | | | | | 295 | | |
| GTG | GAT | GTT | TAC | TTT | GGC | ATG | CCT | GGG | GAA | ATC | GGC | GAG | CAT | GAG | GGT | 1023 |
| Val | Asp | Val | Tyr | Phe | Gly | Met | Pro | Gly | Glu | Ile | Gly | Glu | His | Glu | Gly | |
| | | | | 300 | | | | | 305 | | | | | 310 | | |
| TTC | CTG | AGG | GCC | AAG | ATG | GAC | CTG | GAG | GAG | CGT | AGG | ATG | CGC | CAG | ATT | 1071 |
| Phe | Leu | Arg | Ala | Lys | Met | Asp | Leu | Glu | Glu | Arg | Arg | Met | Arg | Gln | Ile | |
| | | | 315 | | | | | 320 | | | | | 325 | | | |
| AAT | GAG | GTG | ATG | CGT | GAA | TGG | GCC | ATG | GCT | GAC | AGC | CAA | TCT | AAG | AAC | 1119 |
| Asn | Glu | Val | Met | Arg | Glu | Trp | Ala | Met | Ala | Asp | Ser | Gln | Ser | Lys | Asn | |
| 330 | | | | | 335 | | | | | 340 | | | | | | |
| CTG | CCA | AAG | GCG | GAC | AGG | CAG | GCC | CTG | AAT | GAG | CAC | TTC | CAG | TCC | ATT | 1167 |
| Leu | Pro | Lys | Ala | Asp | Arg | Gln | Ala | Leu | Asn | Glu | His | Phe | Gln | Ser | Ile | |
| 345 | | | | | 350 | | | | | 355 | | | | | 360 | |
| CTG | CAG | ACC | CTG | GAA | GAA | CAA | GTG | TCT | GGT | GAA | CGG | CAA | CGC | CTG | GTG | 1215 |
| Leu | Gln | Thr | Leu | Glu | Glu | Gln | Val | Ser | Gly | Glu | Arg | Gln | Arg | Leu | Val | |
| | | | | 365 | | | | | 370 | | | | | 375 | | |
| GAG | ACC | CAC | GCC | ACC | AGA | GTC | ATC | GCT | CTG | ATC | AAC | GAC | CAG | CGC | CGA | 1263 |
| Glu | Thr | His | Ala | Thr | Arg | Val | Ile | Ala | Leu | Ile | Asn | Asp | Gln | Arg | Arg | |
| | | | 380 | | | | | 385 | | | | | 390 | | | |
| GCA | GCC | CTG | GAA | GGT | TTC | CTG | GCA | GCC | TTA | CAG | GGC | GAT | CCG | CCT | CAG | 1311 |
| Ala | Ala | Leu | Glu | Gly | Phe | Leu | Ala | Ala | Leu | Gln | Gly | Asp | Pro | Pro | Gln | |
| | | | 395 | | | | | 400 | | | | | 405 | | | |
| GCT | GAG | CGA | GTT | CTG | ATG | GCC | CTG | AGG | CGC | TAC | CTG | CGC | GCC | GAG | CAG | 1359 |
| Ala | Glu | Arg | Val | Leu | Met | Ala | Leu | Arg | Arg | Tyr | Leu | Arg | Ala | Glu | Gln | |
| | | 410 | | | | | 415 | | | | | 420 | | | | |
| AAA | GAG | CAG | AGG | CAC | ACT | CTG | AGG | CAC | TAC | CAG | CAC | GTG | GCC | GCA | GTG | 1407 |
| Lys | Glu | Gln | Arg | His | Thr | Leu | Arg | His | Tyr | Gln | His | Val | Ala | Ala | Val | |
| 425 | | | | | 430 | | | | | 435 | | | | | 440 | |
| GAT | CCT | GAG | AAG | GCC | CAG | CAG | ATG | CGC | TTT | CAG | GTC | CAG | ACC | CAC | CTT | 1455 |
| Asp | Pro | Glu | Lys | Ala | Gln | Gln | Met | Arg | Phe | Gln | Val | Gln | Thr | His | Leu | |
| | | | | 445 | | | | | 450 | | | | | 455 | | |
| CAG | GTG | ATC | GAA | GAG | CGA | ATG | AAT | CAG | AGC | CTG | GGG | CTG | CTC | GAC | CAG | 1503 |
| Gln | Val | Ile | Glu | Glu | Arg | Met | Asn | Gln | Ser | Leu | Gly | Leu | Leu | Asp | Gln | |
| | | | 460 | | | | | 465 | | | | | 470 | | | |
| AAC | CCT | CAC | CTG | GCT | CAG | GAG | CTG | CGG | CCA | CAG | ATC | CAG | GAG | CTT | CTC | 1551 |
| Asn | Pro | His | Leu | Ala | Gln | Glu | Leu | Arg | Pro | Gln | Ile | Gln | Glu | Leu | Leu | |
| | | 475 | | | | | 480 | | | | | 485 | | | | |
| CTT | GCT | GAA | CAC | TTG | GGT | CCC | AGT | GAA | CTG | GAC | GCC | TCT | GTG | CCC | GGG | 1599 |
| Leu | Ala | Glu | His | Leu | Gly | Pro | Ser | Glu | Leu | Asp | Ala | Ser | Val | Pro | Gly | |
| | | 490 | | | | | 495 | | | | | 500 | | | | |
| AGC | AGC | AGT | GAG | GAC | AAA | GGT | AGC | CTC | CAG | CCT | CCC | GAA | TCC | AAG | GAC | 1647 |
| Ser | Ser | Ser | Glu | Asp | Lys | Gly | Ser | Leu | Gln | Pro | Pro | Glu | Ser | Lys | Asp | |
| 505 | | | | | 510 | | | | | 515 | | | | | 520 | |
| GAT | CCC | CCA | GTG | ACC | CTT | CCA | AAA | GGG | TCC | ACA | GAT | CAA | GAG | TCA | TCC | 1695 |
| Asp | Pro | Pro | Val | Thr | Leu | Pro | Lys | Gly | Ser | Thr | Asp | Gln | Glu | Ser | Ser | |
| | | | | 525 | | | | | 530 | | | | | 535 | | |

| | | | | | | | | | | | | | | | | |
|---|---|---|---|---|---|---|---|---|---|---|---|---|---|---|---|---|
| TCC | TCT | GGG | AGA | GAG | AAG | CTA | ACT | CCA | CTG | GAG | CAG | TAT | GAG | CAA | AAG | 1743 |
| Ser | Ser | Gly | Arg | Glu | Lys | Leu | Thr | Pro | Leu | Glu | Gln | Tyr | Glu | Gln | Lys | |
| | | | 540 | | | | | 545 | | | | | 550 | | | |
| GTG | AAT | GCA | TCC | GCC | CCG | AGG | GGG | TTT | CCG | TTC | CAC | TCG | TCA | GAT | ATC | 1791 |
| Val | Asn | Ala | Ser | Ala | Pro | Arg | Gly | Phe | Pro | Phe | His | Ser | Ser | Asp | Ile | |
| | | 555 | | | | | 560 | | | | | 565 | | | | |
| CAG | CGG | GAT | GAA | CTG | GCT | CCT | TCC | GGG | ACT | GGA | GTG | TCC | CGA | GAG | GCC | 1839 |
| Gln | Arg | Asp | Glu | Leu | Ala | Pro | Ser | Gly | Thr | Gly | Val | Ser | Arg | Glu | Ala | |
| | 570 | | | | | 575 | | | | | 580 | | | | | |
| TTG | TCA | GGT | CTG | CTG | ATC | ATG | GGA | GCT | GGA | GGA | GGC | TCT | CTC | ATT | GTC | 1887 |
| Leu | Ser | Gly | Leu | Leu | Ile | Met | Gly | Ala | Gly | Gly | Gly | Ser | Leu | Ile | Val | |
| 585 | | | | | 590 | | | | | 595 | | | | | 600 | |
| CTA | TCC | TTG | CTG | CTT | CTG | CGC | AAG | AAG | AAA | CCC | TAT | GGG | ACT | ATC | AGC | 1935 |
| Leu | Ser | Leu | Leu | Leu | Leu | Arg | Lys | Lys | Lys | Pro | Tyr | Gly | Thr | Ile | Ser | |
| | | | | 605 | | | | | 610 | | | | | 615 | | |
| CAT | GGA | GTG | GTG | GAG | GTG | GAC | CCC | ATG | CTG | ACC | CTG | GAG | GAG | CAG | CAG | 1983 |
| His | Gly | Val | Val | Glu | Val | Asp | Pro | Met | Leu | Thr | Leu | Glu | Glu | Gln | Gln | |
| | | | 620 | | | | | 625 | | | | | 630 | | | |
| CTC | CGG | GAA | CTT | CAG | AGG | CAT | GGC | TAT | GAG | AAC | CCC | ACC | TAC | CGC | TTC | 2031 |
| Leu | Arg | Glu | Leu | Gln | Arg | His | Gly | Tyr | Glu | Asn | Pro | Thr | Tyr | Arg | Phe | |
| | | 635 | | | | | 640 | | | | | 645 | | | | |
| CTG | GAA | GAA | CGA | CCT | TGACCCCTAC | CCTAGCTGCC | TTCAGCTGAG | CCCTACTGCC | 2086 |
| Leu | Glu | Glu | Arg | Pro | | | | | |
| | | 650 | | | | | | | |

| | | | | | |
|---|---|---|---|---|---|
| TTCTTCCGGC | CCCCCAAACC | CAACTCCCAG | CTTCCGGTGG | GGGAGGGAGA | TCTTGACAAA | 2146 |
| TTCATTCTTG | TTTCCCCTTC | CTAGTTCCAA | ATTCCACACC | CTTAGAAATC | CCCAGCTCCT | 2206 |
| GTCCCACAAG | GGACCTCTTC | ACCTTAATTT | ATTTACGTT | AATTTATTGC | TCCTTAAGGT | 2266 |
| GACCTGGGTC | CCAGGTATGT | ATGTCACTCC | CTGGAATTCA | CCATCCCACG | TTTCTTCACT | 2326 |
| AACATCCCAA | TAAACTCCTC | TTTCCCTCCG | GC | | | 2358 |

( 2 ) INFORMATION FOR SEQ ID NO:16:

( i ) SEQUENCE CHARACTERISTICS:
        ( A ) LENGTH: 653 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
| Met | Gly | Pro | Thr | Ser | Pro | Ala | Ala | Arg | Gly | Gln | Gly | Arg | Arg | Trp | Arg |
| 1 | | | | 5 | | | | | 10 | | | | | 15 | |
| Pro | Pro | Leu | Pro | Leu | Leu | Leu | Pro | Leu | Ser | Leu | Leu | Leu | Leu | Arg | Ala |
| | | | 20 | | | | | 25 | | | | | 30 | | |
| Gln | Leu | Ala | Val | Gly | Asn | Leu | Ala | Val | Gly | Ser | Pro | Ser | Ala | Ala | Glu |
| | | 35 | | | | | 40 | | | | | 45 | | | |
| Ala | Pro | Gly | Ser | Ala | Gln | Val | Ala | Gly | Leu | Cys | Gly | Arg | Leu | Thr | Leu |
| | 50 | | | | | 55 | | | | | 60 | | | | |
| His | Arg | Asp | Leu | Arg | Thr | Gly | Arg | Trp | Glu | Pro | Asp | Pro | Gln | Arg | Ser |
| 65 | | | | | 70 | | | | | 75 | | | | | 80 |
| Arg | Arg | Cys | Leu | Leu | Asp | Pro | Gln | Arg | Val | Leu | Glu | Tyr | Cys | Arg | Gln |
| | | | | 85 | | | | | 90 | | | | | 95 | |
| Met | Tyr | Pro | Glu | Leu | His | Ile | Ala | Arg | Val | Glu | Gln | Ala | Ala | Gln | Ala |
| | | | 100 | | | | | 105 | | | | | 110 | | |
| Ile | Pro | Met | Glu | Arg | Trp | Cys | Gly | Gly | Thr | Arg | Ser | Gly | Arg | Cys | Ala |
| | | | 115 | | | | | 120 | | | | | 125 | | |
| His | Pro | His | His | Glu | Val | Val | Pro | Phe | His | Cys | Leu | Pro | Gly | Glu | Phe |

-continued

```
            130                     135                     140
Val Ser Glu Ala Leu Leu Val Pro Glu Gly Cys Arg Phe Leu His Gln
145                 150                 155                 160

Glu Arg Met Asp Gln Cys Glu Ser Ser Thr Arg Arg His Gln Glu Ala
                165                 170                 175

Gln Glu Ala Cys Ser Ser Gln Gly Leu Ile Leu His Gly Ser Gly Met
            180                 185                 190

Leu Leu Pro Cys Gly Ser Asp Arg Phe Arg Gly Val Glu Tyr Val Cys
        195                 200                 205

Cys Pro Pro Pro Ala Thr Pro Asn Pro Ser Gly Met Ala Ala Gly Asp
    210                 215                 220

Pro Ser Thr Arg Ser Trp Pro Leu Gly Gly Arg Ala Glu Gly Gly Glu
225                 230                 235                 240

Asp Glu Glu Glu Val Glu Ser Phe Pro Gln Pro Val Asp Asp Tyr Phe
                245                 250                 255

Val Glu Pro Pro Gln Ala Glu Glu Glu Glu Glu Glu Glu Glu Glu Arg
            260                 265                 270

Ala Pro Pro Pro Ser Ser His Thr Pro Val Met Val Ser Arg Val Thr
    275                 280                 285

Pro Thr Pro Arg Pro Thr Asp Gly Val Asp Val Tyr Phe Gly Met Pro
290                 295                 300

Gly Glu Ile Gly Glu His Glu Gly Phe Leu Arg Ala Lys Met Asp Leu
305                 310                 315                 320

Glu Glu Arg Arg Met Arg Gln Ile Asn Glu Val Met Arg Glu Trp Ala
                325                 330                 335

Met Ala Asp Ser Gln Ser Lys Asn Leu Pro Lys Ala Asp Arg Gln Ala
            340                 345                 350

Leu Asn Glu His Phe Gln Ser Ile Leu Gln Thr Leu Glu Glu Gln Val
        355                 360                 365

Ser Gly Glu Arg Gln Arg Leu Val Glu Thr His Ala Thr Arg Val Ile
    370                 375                 380

Ala Leu Ile Asn Asp Gln Arg Arg Ala Ala Leu Glu Gly Phe Leu Ala
385                 390                 395                 400

Ala Leu Gln Gly Asp Pro Pro Gln Ala Glu Arg Val Leu Met Ala Leu
            405                 410                 415

Arg Arg Tyr Leu Arg Ala Glu Gln Lys Glu Gln Arg His Thr Leu Arg
        420                 425                 430

His Tyr Gln His Val Ala Ala Val Asp Pro Glu Lys Ala Gln Gln Met
    435                 440                 445

Arg Phe Gln Val Gln Thr His Leu Gln Val Ile Glu Glu Arg Met Asn
450                 455                 460

Gln Ser Leu Gly Leu Leu Asp Gln Asn Pro His Leu Ala Gln Glu Leu
465                 470                 475                 480

Arg Pro Gln Ile Gln Glu Leu Leu Leu Ala Glu His Leu Gly Pro Ser
            485                 490                 495

Glu Leu Asp Ala Ser Val Pro Gly Ser Ser Ser Glu Asp Lys Gly Ser
        500                 505                 510

Leu Gln Pro Pro Glu Ser Lys Asp Asp Pro Pro Val Thr Leu Pro Lys
    515                 520                 525

Gly Ser Thr Asp Gln Glu Ser Ser Ser Gly Arg Glu Lys Leu Thr
530                 535                 540

Pro Leu Glu Gln Tyr Glu Gln Lys Val Asn Ala Ser Ala Pro Arg Gly
545                 550                 555                 560
```

-continued

| | | | | | | | | | | | | | | | |
|---|---|---|---|---|---|---|---|---|---|---|---|---|---|---|---|
| Phe | Pro | Phe | His | Ser | Ser | Asp | Ile | Gln | Arg | Asp | Glu | Leu | Ala | Pro | Ser |
| | | | | 565 | | | | | 570 | | | | | 575 | |
| Gly | Thr | Gly | Val | Ser | Arg | Glu | Ala | Leu | Ser | Gly | Leu | Leu | Ile | Met | Gly |
| | | | 580 | | | | | 585 | | | | | 590 | | |
| Ala | Gly | Gly | Gly | Ser | Leu | Ile | Val | Leu | Ser | Leu | Leu | Leu | Arg | Lys | |
| | | 595 | | | | | 600 | | | | | 605 | | | |
| Lys | Lys | Pro | Tyr | Gly | Thr | Ile | Ser | His | Gly | Val | Val | Glu | Val | Asp | Pro |
| 610 | | | | | | 615 | | | | 620 | | | | | |
| Met | Leu | Thr | Leu | Glu | Glu | Gln | Gln | Leu | Arg | Glu | Leu | Gln | Arg | His | Gly |
| 625 | | | | | 630 | | | | 635 | | | | | | 640 |
| Tyr | Glu | Asn | Pro | Thr | Tyr | Arg | Phe | Leu | Glu | Glu | Arg | Pro | | | |
| | | | | 645 | | | | | 650 | | | | | | |

( 2 ) INFORMATION FOR SEQ ID NO:17:

( i ) SEQUENCE CHARACTERISTICS:
        ( A ) LENGTH: 634 amino acids
        ( B ) TYPE: amino acid
        ( D ) TOPOLOGY: linear ( x i ) SEQUENCE DESCRIPTION: SEQ ID NO:17:

| | | | | | | | | | | | | | | | |
|---|---|---|---|---|---|---|---|---|---|---|---|---|---|---|---|
| Leu | Leu | Leu | Pro | Leu | Ser | Leu | Leu | Leu | Arg | Ala | Gln | Leu | Ala | Val | |
| 1 | | | | 5 | | | | | 10 | | | | | 15 | |
| Gly | Asn | Leu | Ala | Val | Gly | Ser | Pro | Ser | Ala | Ala | Glu | Ala | Pro | Gly | Ser |
| | | | 20 | | | | | 25 | | | | | 30 | | |
| Ala | Gln | Val | Ala | Gly | Leu | Cys | Gly | Arg | Leu | Thr | Leu | His | Arg | Asp | Leu |
| | | | 35 | | | | 40 | | | | | 45 | | | |
| Arg | Thr | Gly | Arg | Trp | Glu | Pro | Asp | Pro | Gln | Arg | Ser | Arg | Arg | Cys | Leu |
| | | 50 | | | | | 55 | | | | | 60 | | | |
| Leu | Asp | Pro | Gln | Arg | Val | Leu | Glu | Tyr | Cys | Arg | Gln | Met | Tyr | Pro | Glu |
| 65 | | | | | 70 | | | | 75 | | | | | | 80 |
| Leu | His | Ile | Ala | Arg | Val | Glu | Gln | Ala | Ala | Gln | Ala | Ile | Pro | Met | Glu |
| | | | | 85 | | | | | 90 | | | | | 95 | |
| Arg | Trp | Cys | Gly | Gly | Thr | Arg | Ser | Gly | Arg | Cys | Ala | His | Pro | His | His |
| | | | 100 | | | | | 105 | | | | | 110 | | |
| Glu | Val | Val | Pro | Phe | His | Cys | Leu | Pro | Gly | Glu | Phe | Val | Ser | Glu | Ala |
| | | 115 | | | | | 120 | | | | | 125 | | | |
| Leu | Leu | Val | Pro | Glu | Gly | Cys | Arg | Phe | Leu | His | Gln | Glu | Arg | Met | Asp |
| | 130 | | | | | 135 | | | | | 140 | | | | |
| Gln | Cys | Glu | Ser | Ser | Thr | Arg | Arg | His | Gln | Glu | Ala | Gln | Glu | Ala | Cys |
| 145 | | | | | 150 | | | | | 155 | | | | | 160 |
| Ser | Ser | Gln | Gly | Leu | Ile | Leu | His | Gly | Ser | Gly | Met | Leu | Leu | Pro | Cys |
| | | | | 165 | | | | | 170 | | | | | 175 | |
| Gly | Ser | Asp | Arg | Phe | Arg | Gly | Val | Glu | Tyr | Val | Cys | Cys | Pro | Pro | Pro |
| | | | 180 | | | | | 185 | | | | | 190 | | |
| Ala | Thr | Pro | Asn | Pro | Ser | Gly | Met | Ala | Ala | Gly | Asp | Pro | Ser | Thr | Arg |
| | | 195 | | | | | 200 | | | | | 205 | | | |
| Ser | Trp | Pro | Leu | Gly | Gly | Arg | Ala | Glu | Gly | Gly | Glu | Asp | Glu | Glu | Glu |
| | | 210 | | | | | 215 | | | | | 220 | | | |
| Val | Glu | Ser | Phe | Pro | Gln | Pro | Val | Asp | Asp | Tyr | Phe | Val | Glu | Pro | Pro |
| 225 | | | | | 230 | | | | | 235 | | | | | 240 |
| Gln | Ala | Glu | Glu | Glu | Glu | Glu | Glu | Glu | Glu | Glu | Arg | Ala | Pro | Pro | Pro |
| | | | | 245 | | | | | 250 | | | | | 255 | |
| Ser | Ser | His | Thr | Pro | Val | Met | Val | Ser | Arg | Val | Thr | Pro | Thr | Pro | Arg |
| | | | 260 | | | | | 265 | | | | | 270 | | |
| Pro | Thr | Asp | Gly | Val | Asp | Val | Tyr | Phe | Gly | Met | Pro | Gly | Glu | Ile | Gly |

-continued

```
                        275                           280                           285
      Glu  His  Glu  Gly  Phe  Leu  Arg  Ala  Lys  Met  Asp  Leu  Glu  Arg  Arg
           290                          295                     300
      Met  Arg  Gln  Ile  Asn  Glu  Val  Met  Arg  Glu  Trp  Ala  Met  Ala  Asp  Ser
      305                     310                     315                          320
      Gln  Ser  Lys  Asn  Leu  Pro  Lys  Ala  Asp  Arg  Gln  Ala  Leu  Asn  Glu  His
                          325                     330                          335
      Phe  Gln  Ser  Ile  Leu  Gln  Thr  Leu  Glu  Glu  Gln  Val  Ser  Gly  Glu  Arg
                     340                          345                     350
      Gln  Arg  Leu  Val  Glu  Thr  His  Ala  Thr  Arg  Val  Ile  Ala  Leu  Ile  Asn
                355                          360                     365
      Asp  Gln  Arg  Arg  Ala  Ala  Leu  Glu  Gly  Phe  Leu  Ala  Ala  Leu  Gln  Gly
           370                          375                     380
      Asp  Pro  Pro  Gln  Ala  Glu  Arg  Val  Leu  Met  Ala  Leu  Arg  Arg  Tyr  Leu
      385                     390                     395                          400
      Arg  Ala  Glu  Gln  Lys  Glu  Gln  Arg  His  Thr  Leu  Arg  His  Tyr  Gln  His
                          405                     410                          415
      Val  Ala  Ala  Val  Asp  Pro  Glu  Lys  Ala  Gln  Gln  Met  Arg  Phe  Gln  Val
                     420                          425                     430
      Gln  Thr  His  Leu  Gln  Val  Ile  Glu  Glu  Arg  Met  Asn  Gln  Ser  Leu  Gly
                435                          440                     445
      Leu  Leu  Asp  Gln  Asn  Pro  His  Leu  Ala  Gln  Glu  Leu  Arg  Pro  Gln  Ile
           450                          455                     460
      Gln  Glu  Leu  Leu  Leu  Ala  Glu  His  Leu  Gly  Pro  Ser  Glu  Leu  Asp  Ala
      465                     470                     475                          480
      Ser  Val  Pro  Gly  Ser  Ser  Ser  Glu  Asp  Lys  Gly  Ser  Leu  Gln  Pro  Pro
                          485                     490                          495
      Glu  Ser  Lys  Asp  Asp  Pro  Val  Thr  Leu  Pro  Lys  Gly  Ser  Thr  Asp
                     500                          505                     510
      Gln  Glu  Ser  Ser  Ser  Ser  Gly  Arg  Glu  Lys  Leu  Thr  Pro  Leu  Glu  Gln
                515                          520                     525
      Tyr  Glu  Gln  Lys  Val  Asn  Ala  Ser  Ala  Pro  Arg  Gly  Phe  Pro  Phe  His
           530                          535                     540
      Ser  Ser  Asp  Ile  Gln  Arg  Asp  Glu  Leu  Ala  Pro  Ser  Gly  Thr  Gly  Val
      545                     550                     555                          560
      Ser  Arg  Glu  Ala  Leu  Ser  Gly  Leu  Leu  Ile  Met  Gly  Ala  Gly  Gly  Gly
                          565                     570                          575
      Ser  Leu  Ile  Val  Leu  Ser  Leu  Leu  Leu  Arg  Lys  Lys  Lys  Pro  Tyr
                     580                          585                     590
      Gly  Thr  Ile  Ser  His  Gly  Val  Val  Glu  Val  Asp  Pro  Met  Leu  Thr  Leu
                595                          600                     605
      Glu  Glu  Gln  Gln  Leu  Arg  Glu  Leu  Gln  Arg  His  Gly  Tyr  Glu  Asn  Pro
           610                          615                     620
      Thr  Tyr  Arg  Phe  Leu  Glu  Glu  Glu  Arg  Pro
      625                     630
```

( 2 ) INFORMATION FOR SEQ ID NO:18:

( i ) SEQUENCE CHARACTERISTICS:
        ( A ) LENGTH: 694 amino acids
        ( B ) TYPE: amino acid
        ( D ) TOPOLOGY: linear ( x i ) SEQUENCE DESCRIPTION: SEQ ID NO:18:

```
      Met  Leu  Pro  Gly  Leu  Ala  Leu  Leu  Leu  Leu  Ala  Ala  Trp  Thr  Ala  Arg
      1                       5                       10                          15
```

-continued

```
Ala Leu Glu Val Pro Thr Asp Gly Asn Ala Gly Leu Leu Ala Glu Pro
            20              25              30
Gln Ile Ala Met Phe Cys Gly Arg Leu Asn Met His Met Asn Val Gln
        35              40              45
Asn Gly Lys Trp Asp Ser Asp Pro Ser Gly Thr Lys Thr Cys Ile Asp
    50              55              60
Thr Lys Glu Gly Ile Leu Gln Tyr Cys Gln Glu Val Tyr Pro Glu Leu
65              70              75              80
Gln Ile Thr Asn Val Val Glu Ala Asn Gln Pro Val Thr Ile Gln Asn
                85              90              95
Trp Cys Lys Arg Gly Arg Lys Gln Cys Lys Thr His Pro His Phe Val
            100             105             110
Ile Pro Tyr Arg Cys Leu Val Gly Glu Phe Val Ser Asp Ala Leu Leu
        115             120             125
Val Pro Asp Lys Cys Lys Phe Leu His Gln Glu Arg Met Asp Val Cys
130             135             140
Glu Thr His Leu His Trp His Thr Val Ala Lys Glu Thr Cys Ser Glu
145             150             155             160
Lys Ser Thr Asn Leu His Asp Tyr Gly Met Leu Leu Pro Cys Gly Ile
                165             170             175
Asp Lys Phe Arg Gly Val Glu Phe Val Cys Cys Pro Leu Ala Glu Glu
            180             185             190
Ser Asp Asn Val Asp Ser Ala Asp Ala Glu Glu Asp Asp Ser Asp Val
        195             200             205
Trp Trp Gly Gly Ala Asp Thr Asp Tyr Ala Asp Gly Ser Glu Asp Lys
210             215             220
Val Val Glu Val Ala Glu Glu Glu Val Ala Glu Val Glu Glu Glu
225             230             235             240
Glu Ala Asp Asp Asp Glu Asp Asp Glu Asp Gly Asp Glu Val Glu Glu
                245             250             255
Glu Ala Glu Glu Pro Tyr Glu Glu Ala Thr Glu Arg Thr Thr Ser Ile
            260             265             270
Ala Thr Thr Thr Thr Thr Thr Thr Glu Ser Val Glu Glu Val Val Arg
        275             280             285
Val Pro Thr Thr Ala Ala Ser Thr Pro Asp Ala Val Asp Lys Tyr Leu
290             295             300
Glu Thr Pro Gly Asp Glu Asn Glu His Ala His Phe Gln Lys Ala Lys
305             310             315             320
Glu Arg Leu Glu Ala Lys His Arg Glu Arg Met Ser Gln Val Met Arg
                325             330             335
Glu Trp Glu Glu Ala Glu Arg Gln Ala Lys Asn Leu Pro Lys Ala Asp
            340             345             350
Lys Lys Ala Val Ile Gln His Phe Gln Glu Lys Val Glu Ser Leu Glu
        355             360             365
Gln Glu Ala Ala Asn Glu Arg Gln Gln Leu Val Glu Thr His Met Ala
370             375             380
Arg Val Glu Ala Met Leu Asn Asp Arg Arg Arg Leu Ala Leu Glu Asn
385             390             395             400
Tyr Ile Thr Ala Leu Gln Ala Val Pro Pro Arg Pro Arg His Val Phe
                405             410             415
Asn Met Leu Lys Lys Tyr Val Arg Ala Glu Gln Lys Asp Arg Gln His
            420             425             430
Thr Leu Lys His Phe Glu His Val Arg Met Val Asp Pro Lys Lys Ala
```

|   |   |   |   |   | 435 |   |   |   |   |   | 440 |   |   |   |   |   | 445 |   |   |
|---|---|---|---|---|---|---|---|---|---|---|---|---|---|---|---|---|---|---|---|

```
            435                    440                    445
Ala  Gln  Ile  Arg  Ser  Gln  Val  Met  Thr  His  Leu  Arg  Val  Ile  Tyr  Glu
     450                      455                      460

Arg  Met  Asn  Gln  Ser  Leu  Ser  Leu  Leu  Tyr  Asn  Val  Pro  Ala  Val  Ala
465                      470                      475                      480

Glu  Glu  Ile  Gln  Asp  Glu  Val  Asp  Glu  Leu  Leu  Gln  Lys  Glu  Gln  Asn
                    485                      490                      495

Tyr  Ser  Asp  Asp  Val  Leu  Ala  Asn  Met  Ile  Ser  Glu  Pro  Arg  Ile  Ser
               500                      505                      510

Tyr  Gly  Asn  Asp  Ala  Leu  Met  Pro  Ser  Leu  Thr  Glu  Thr  Lys  Thr  Thr
          515                      520                      525

Val  Glu  Leu  Leu  Pro  Val  Asn  Gly  Glu  Phe  Ser  Leu  Asp  Asp  Leu  Gln
     530                      535                      540

Pro  Trp  His  Ser  Phe  Gly  Ala  Asp  Ser  Val  Pro  Ala  Asn  Thr  Glu  Asn
545                      550                      555                      560

Glu  Val  Glu  Pro  Val  Asp  Ala  Arg  Pro  Ala  Ala  Asp  Arg  Gly  Leu  Thr
                    565                      570                      575

Thr  Arg  Pro  Gly  Ser  Gly  Leu  Thr  Asn  Ile  Lys  Thr  Glu  Glu  Ile  Ser
               580                      585                      590

Glu  Val  Lys  Met  Asp  Ala  Glu  Phe  Arg  His  Asp  Ser  Gly  Tyr  Glu  Val
          595                      600                      605

His  His  Gln  Lys  Leu  Val  Phe  Phe  Ala  Glu  Asp  Val  Gly  Ser  Asn  Lys
     610                      615                      620

Gly  Ala  Ile  Ile  Gly  Leu  Met  Val  Gly  Gly  Val  Val  Ile  Ala  Thr  Val
625                      630                      635                      640

Ile  Val  Ile  Thr  Leu  Val  Met  Leu  Lys  Lys  Lys  Gln  Tyr  Thr  Ser  Ile
                    645                      650                      655

His  His  Gly  Val  Val  Glu  Val  Asp  Ala  Ala  Val  Thr  Pro  Glu  Glu  Arg
               660                      665                      670

His  Leu  Ser  Lys  Met  Gln  Gln  Asn  Gly  Tyr  Glu  Asn  Pro  Thr  Tyr  Lys
          675                      680                      685

Phe  Phe  Glu  Gln  Met  Gln
     690
```

( 2 ) INFORMATION FOR SEQ ID NO:19:

( i ) SEQUENCE CHARACTERISTICS:
        ( A ) LENGTH: 190 amino acids
        ( B ) TYPE: amino acid
        ( D ) TOPOLOGY: linear ( x i ) SEQUENCE DESCRIPTION: SEQ ID NO:19:

```
Leu  Leu  Leu  Pro  Leu  Ser  Leu  Leu  Leu  Arg  Ala  Gln  Leu  Ala  Val
1              5                        10                       15

Gly  Asn  Leu  Ala  Val  Gly  Ser  Pro  Ser  Ala  Ala  Glu  Ala  Pro  Gly  Ser
          20                       25                       30

Ala  Gln  Val  Ala  Gly  Leu  Cys  Gly  Arg  Leu  Thr  Leu  His  Arg  Asp  Leu
     35                       40                       45

Arg  Thr  Gly  Arg  Trp  Glu  Pro  Asp  Pro  Gln  Arg  Ser  Arg  Arg  Cys  Leu
     50                       55                       60

Leu  Asp  Pro  Gln  Arg  Val  Leu  Glu  Tyr  Cys  Arg  Gln  Met  Tyr  Pro  Glu
65                       70                       75                       80

Leu  His  Ile  Ala  Arg  Val  Glu  Gln  Ala  Ala  Gln  Ala  Ile  Pro  Met  Glu
               85                       90                       95

Arg  Trp  Cys  Gly  Gly  Thr  Arg  Ser  Gly  Arg  Cys  Ala  His  Pro  His  His
                    100                      105                      110
```

```
Glu  Val  Val  Pro  Phe  His  Cys  Leu  Pro  Gly  Glu  Phe  Val  Ser  Glu  Ala
          115                120                125

Leu  Leu  Val  Pro  Glu  Gly  Cys  Arg  Phe  Leu  His  Gln  Glu  Arg  Met  Asp
          130                135                140

Gln  Cys  Glu  Ser  Ser  Thr  Arg  Arg  His  Gln  Glu  Ala  Gln  Glu  Ala  Cys
145                          150                155                          160

Ser  Ser  Gln  Gly  Leu  Ile  Leu  His  Gly  Ser  Gly  Met  Leu  Leu  Pro  Cys
                    165                     170                     175

Gly  Ser  Asp  Arg  Phe  Arg  Gly  Val  Glu  Tyr  Val  Cys  Cys  Pro
                    180                185                     190
```

(2) INFORMATION FOR SEQ ID NO:20:

(i) SEQUENCE CHARACTERISTICS:
       (A) LENGTH: 188 amino acids
       (B) TYPE: amino acid
       (C) STRANDEDNESS: single
       (D) TOPOLOGY: linear (xi) SEQUENCE DESCRIPTION: SEQ ID NO:20:

```
Met  Leu  Pro  Gly  Leu  Ala  Leu  Leu  Leu  Ala  Ala  Trp  Thr  Ala  Arg
1               5                         10                         15

Ala  Leu  Glu  Val  Pro  Thr  Asp  Gly  Asn  Ala  Gly  Leu  Leu  Ala  Glu  Pro
               20                     25                     30

Gln  Ile  Ala  Met  Phe  Cys  Gly  Arg  Leu  Asn  Met  His  Met  Asn  Met  Val  Gln
               35                     40                     45

Asn  Gly  Lys  Trp  Asp  Ser  Asp  Pro  Ser  Gly  Thr  Lys  Thr  Cys  Ile  Asp
     50                     55                     60

Thr  Lys  Glu  Gly  Ile  Leu  Gln  Tyr  Cys  Gln  Glu  Val  Tyr  Pro  Glu  Leu
65                     70                     75                          80

Gln  Ile  Thr  Asn  Val  Val  Glu  Ala  Asn  Gln  Pro  Val  Thr  Ile  Gln  Asn
                    85                     90                          95

Trp  Cys  Lys  Arg  Gly  Arg  Lys  Gln  Cys  Lys  Thr  His  Pro  His  Phe  Val
               100                    105                    110

Ile  Pro  Tyr  Arg  Cys  Leu  Val  Gly  Glu  Phe  Val  Ser  Asp  Ala  Leu  Leu
          115                     120                    125

Val  Pro  Asp  Lys  Cys  Lys  Phe  Leu  His  Gln  Glu  Arg  Met  Asp  Val  Cys
     130                    135                    140

Glu  Thr  His  Leu  His  Trp  His  Thr  Val  Ala  Lys  Glu  Thr  Cys  Ser  Glu
145                    150                    155                         160

Lys  Ser  Thr  Asn  Leu  His  Asp  Tyr  Gly  Met  Leu  Leu  Pro  Cys  Gly  Ile
                    165                    170                    175

Asp  Lys  Phe  Arg  Gly  Val  Glu  Phe  Val  Cys  Cys  Pro
               180                    185
```

(2) INFORMATION FOR SEQ ID NO:21:

(i) SEQUENCE CHARACTERISTICS:
       (A) LENGTH: 197 amino acids
       (B) TYPE: amino acid
       (D) TOPOLOGY: linear (xi) SEQUENCE DESCRIPTION: SEQ ID NO:21:

```
Met  Cys  Ala  Ala  Leu  Arg  Arg  Asn  Leu  Leu  Leu  Arg  Ser  Leu  Trp  Val
1               5                         10                         15

Val  Leu  Ala  Ile  Gly  Thr  Ala  Gln  Val  Gln  Ala  Ala  Ser  Ser  Pro  Arg
               20                     25                     30

Trp  Pro  Gln  Ile  Ala  Val  Leu  Cys  Glu  Ala  Gly  Gln  Ile  Tyr  Gln  Pro
```

|  | 35 |  |  |  |  | 40 |  |  |  |  | 45 |  |  |  |
|---|---|---|---|---|---|---|---|---|---|---|---|---|---|---|
| Gln | Tyr<br>50 | Leu | Ser | Glu | Glu<br>55 | Gly | Arg | Trp | Val | Thr<br>60 | Asp | Leu | Ser | Lys | Lys |
| Thr<br>65 | Thr | Gly | Pro | Thr<br>70 | Cys | Leu | Arg | Asp | Lys<br>75 | Met | Asp | Leu | Asp | Tyr | Cys<br>80 |
| Lys | Lys | Ala | Tyr | Pro<br>85 | Asn | Arg | Asp | Ile | Thr<br>90 | Asn | Ile | Val | Glu | Ser<br>95 | Ser |
| His | Tyr | Gln | Lys<br>100 | Ile | Gly | Gly | Trp | Cys<br>105 | Arg | Gln | Gly | Ala | Leu<br>110 | Asn | Ala |
| Ala | Lys | Cys<br>115 | Lys | Gly | Ser | His | Arg<br>120 | Trp | Ile | Lys | Pro | Phe<br>125 | Arg | Cys | Leu |
| Gly | Pro<br>130 | Phe | Gln | Ser | Asp | Ala<br>135 | Leu | Leu | Tyr | Pro | Glu<br>140 | Gly | Cys | Leu | Phe |
| Asp<br>145 | His | Ile | His | Asn | Ala<br>150 | Ser | Arg | Cys | Trp | Pro<br>155 | Phe | Val | Arg | Trp | Asn<br>160 |
| Gln | Thr | Gly | Ala | Ala<br>165 | Ala | Cys | Gln | Glu | Arg<br>170 | Gly | Met | Gly | Met | Arg<br>175 | Thr |
| Phe | Ala | Met | Leu<br>180 | Leu | Pro | Cys | Gly | Ile<br>185 | Ser | Val | Phe | Ser | Gly<br>190 | Val | Glu |
| Phe | Val | Cys<br>195 | Cys | Pro |  |  |  |  |  |  |  |  |  |  |  |

(2) INFORMATION FOR SEQ ID NO:22:

(i) SEQUENCE CHARACTERISTICS:
(A) LENGTH: 155 amino acids
(B) TYPE: amino acid
(D) TOPOLOGY: linear (xi) SEQUENCE DESCRIPTION: SEQ ID NO:22:

|  |  |  |  |  |  |  |  |  |  |  |  |  |  |  |
|---|---|---|---|---|---|---|---|---|---|---|---|---|---|---|
| Ala<br>1 | Lys | Met | Asp | Leu<br>5 | Glu | Glu | Arg | Arg | Met<br>10 | Arg | Gln | Ile | Asn | Glu | Val<br>15 |
| Met | Arg | Glu | Trp<br>20 | Ala | Met | Ala | Asp | Ser<br>25 | Gln | Ser | Lys | Asn | Leu<br>30 | Pro | Lys |
| Ala | Asp | Arg<br>35 | Gln | Ala | Leu | Asn | Glu<br>40 | His | Phe | Gln | Ser | Ile<br>45 | Leu | Gln | Thr |
| Leu | Glu<br>50 | Glu | Gln | Val | Ser | Gly<br>55 | Glu | Arg | Gln | Arg | Leu<br>60 | Val | Glu | Thr | His |
| Ala<br>65 | Thr | Arg | Val | Ile<br>70 | Ala | Leu | Ile | Asn | Asp<br>75 | Gln | Arg | Arg | Ala | Ala | Leu<br>80 |
| Glu | Gly | Phe | Leu | Ala<br>85 | Ala | Leu | Gln | Gly | Asp<br>90 | Pro | Pro | Gln | Ala | Glu<br>95 | Arg |
| Val | Leu | Met | Ala<br>100 | Leu | Arg | Arg | Tyr | Leu<br>105 | Arg | Ala | Glu | Gln | Lys<br>110 | Glu | Gln |
| Arg | His | Thr<br>115 | Leu | Arg | His | Tyr | Gln<br>120 | His | Val | Ala | Ala | Val<br>125 | Asp | Pro | Glu |
| Lys | Ala<br>130 | Gln | Gln | Met | Arg | Phe<br>135 | Gln | Val | Gln | Thr | His<br>140 | Leu | Gln | Val | Ile |
| Glu<br>145 | Glu | Arg | Met | Asn | Gln<br>150 | Ser | Leu | Gly | Leu | Leu<br>155 |  |  |  |  |  |

(2) INFORMATION FOR SEQ ID NO:23:

(i) SEQUENCE CHARACTERISTICS:
(A) LENGTH: 155 amino acids
(B) TYPE: amino acid
(D) TOPOLOGY: linear ( x i ) SEQUENCE DESCRIPTION: SEQ ID NO:23:

| Ala | Lys | Glu | Arg | Leu | Glu | Ala | Lys | His | Arg | Glu | Arg | Met | Ser | Gln | Val |
|---|---|---|---|---|---|---|---|---|---|---|---|---|---|---|---|
| 1 | | | | 5 | | | | | 10 | | | | | 15 | |

| Met | Arg | Glu | Trp | Glu | Glu | Ala | Glu | Arg | Gln | Ala | Lys | Asn | Leu | Pro | Lys |
|---|---|---|---|---|---|---|---|---|---|---|---|---|---|---|---|
| | | | 20 | | | | | 25 | | | | | 30 | | |

| Ala | Asp | Lys | Lys | Ala | Val | Ile | Gln | His | Phe | Gln | Glu | Lys | Val | Glu | Ser |
|---|---|---|---|---|---|---|---|---|---|---|---|---|---|---|---|
| | | 35 | | | | | 40 | | | | | 45 | | | |

| Leu | Glu | Gln | Glu | Ala | Ala | Asn | Glu | Arg | Gln | Gln | Leu | Val | Glu | Thr | His |
|---|---|---|---|---|---|---|---|---|---|---|---|---|---|---|---|
| | 50 | | | | | 55 | | | | | 60 | | | | |

| Met | Ala | Arg | Val | Glu | Ala | Met | Leu | Asn | Asp | Arg | Arg | Arg | Leu | Ala | Leu |
|---|---|---|---|---|---|---|---|---|---|---|---|---|---|---|---|
| 65 | | | | | 70 | | | | | 75 | | | | | 80 |

| Glu | Asn | Tyr | Ile | Thr | Ala | Leu | Gln | Ala | Val | Pro | Pro | Arg | Pro | Arg | His |
|---|---|---|---|---|---|---|---|---|---|---|---|---|---|---|---|
| | | | | 85 | | | | | 90 | | | | | 95 | |

| Val | Phe | Asn | Met | Leu | Lys | Lys | Tyr | Val | Arg | Ala | Glu | Gln | Lys | Asp | Arg |
|---|---|---|---|---|---|---|---|---|---|---|---|---|---|---|---|
| | | | 100 | | | | | 105 | | | | | 110 | | |

| Gln | His | Thr | Leu | Lys | His | Phe | Glu | His | Val | Arg | Met | Val | Asp | Pro | Lys |
|---|---|---|---|---|---|---|---|---|---|---|---|---|---|---|---|
| | | 115 | | | | | 120 | | | | | 125 | | | |

| Lys | Ala | Ala | Gln | Ile | Arg | Ser | Gln | Val | Met | Thr | His | Leu | Arg | Val | Ile |
|---|---|---|---|---|---|---|---|---|---|---|---|---|---|---|---|
| | 130 | | | | | 135 | | | | | 140 | | | | |

| Tyr | Glu | Arg | Met | Asn | Gln | Ser | Leu | Ser | Leu | Leu |
|---|---|---|---|---|---|---|---|---|---|---|
| 145 | | | | | 150 | | | | | 155 |

( 2 ) INFORMATION FOR SEQ ID NO:24:

( i ) SEQUENCE CHARACTERISTICS:
        ( A ) LENGTH: 166 amino acids
        ( B ) TYPE: amino acid
        ( D ) TOPOLOGY: linear ( x i ) SEQUENCE DESCRIPTION: SEQ ID NO:24:

| Ser | Gln | Lys | Arg | Leu | Glu | Glu | Ser | His | Arg | Glu | Lys | Val | Thr | Arg | Val |
|---|---|---|---|---|---|---|---|---|---|---|---|---|---|---|---|
| 1 | | | | 5 | | | | | 10 | | | | | 15 | |

| Met | Lys | Asp | Trp | Ser | Asp | Leu | Glu | Glu | Lys | Tyr | Gln | Asp | Met | Arg | Leu |
|---|---|---|---|---|---|---|---|---|---|---|---|---|---|---|---|
| | | | 20 | | | | | 25 | | | | | 30 | | |

| Ala | Asp | Pro | Lys | Ala | Ala | Gln | Ser | Phe | Lys | Gln | Arg | Met | Thr | Ala | Arg |
|---|---|---|---|---|---|---|---|---|---|---|---|---|---|---|---|
| | | 35 | | | | | 40 | | | | | 45 | | | |

| Phe | Gln | Thr | Ser | Val | Gln | Ala | Leu | Glu | Glu | Glu | Gly | Asn | Ala | Glu | Lys |
|---|---|---|---|---|---|---|---|---|---|---|---|---|---|---|---|
| | 50 | | | | | 55 | | | | | 60 | | | | |

| His | Gln | Leu | Ala | Ala | Met | His | Gln | Gln | Arg | Val | Leu | Ala | His | Ile | Asn |
|---|---|---|---|---|---|---|---|---|---|---|---|---|---|---|---|
| 65 | | | | | 70 | | | | | 75 | | | | | 80 |

| Gln | Arg | Lys | Arg | Glu | Ala | Met | Thr | Cys | Tyr | Thr | Gln | Ala | Leu | Thr | Glu |
|---|---|---|---|---|---|---|---|---|---|---|---|---|---|---|---|
| | | | | 85 | | | | | 90 | | | | | 95 | |

| Gln | Pro | Pro | Asn | Ala | His | His | Val | Glu | Lys | Cys | Leu | Gln | Lys | Ile | Leu |
|---|---|---|---|---|---|---|---|---|---|---|---|---|---|---|---|
| | | | 100 | | | | | 105 | | | | | 110 | | |

| Arg | Ala | Leu | His | Lys | Asp | Arg | Ala | His | Ala | Leu | Ala | His | Tyr | Arg | His |
|---|---|---|---|---|---|---|---|---|---|---|---|---|---|---|---|
| | | 115 | | | | | 120 | | | | | 125 | | | |

| Leu | Leu | Asn | Ser | Gly | Gly | Pro | Gly | Gly | Leu | Glu | Ala | Ala | Ala | Ser | Glu |
|---|---|---|---|---|---|---|---|---|---|---|---|---|---|---|---|
| | 130 | | | | | 135 | | | | | 140 | | | | |

| Arg | Pro | Arg | Thr | Leu | Glu | Arg | Leu | Ile | Asp | Ile | Asp | Arg | Ala | Val | Asn |
|---|---|---|---|---|---|---|---|---|---|---|---|---|---|---|---|
| 145 | | | | 150 | | | | | 155 | | | | | | 160 |

| Gln | Ser | Met | Thr | Met | Leu |
|---|---|---|---|---|---|
| | | | | 165 | |

( 2 ) INFORMATION FOR SEQ ID NO:25:

( i ) SEQUENCE CHARACTERISTICS:
        ( A ) LENGTH: 46 amino acids ( B ) TYPE: amino acid
( D ) TOPOLOGY: linear ( x i ) SEQUENCE DESCRIPTION: SEQ ID NO:25:

| Lys | Lys | Lys | Pro | Tyr | Gly | Thr | Ile | Ser | His | Gly | Val | Val | Glu | Val | Asp |
| 1 | | | | 5 | | | | | 10 | | | | | 15 | |

| Pro | Met | Leu | Thr | Leu | Glu | Glu | Gln | Gln | Leu | Arg | Glu | Leu | Gln | Arg | His |
| | | | 20 | | | | 25 | | | | | 30 | | | |

| Gly | Tyr | Glu | Asn | Pro | Thr | Tyr | Arg | Phe | Leu | Glu | Glu | Arg | Pro |
| | | 35 | | | | | 40 | | | | | 45 | |

( 2 ) INFORMATION FOR SEQ ID NO:26:

( i ) SEQUENCE CHARACTERISTICS:
( A ) LENGTH: 47 amino acids
( B ) TYPE: amino acid
( D ) TOPOLOGY: linear ( x i ) SEQUENCE DESCRIPTION: SEQ ID NO:26:

| Lys | Lys | Lys | Gln | Tyr | Thr | Ser | Ile | His | His | Gly | Val | Val | Glu | Val | Asp |
| 1 | | | | 5 | | | | | 10 | | | | | 15 | |

| Ala | Ala | Val | Thr | Pro | Glu | Glu | Arg | His | Leu | Ser | Lys | Met | Gln | Gln | Asn |
| | | | 20 | | | | 25 | | | | | 30 | | | |

| Gly | Tyr | Glu | Asn | Pro | Thr | Tyr | Lys | Phe | Phe | Glu | Gln | Met | Gln | Asn |
| | | 35 | | | | | 40 | | | | | 45 | | |

( 2 ) INFORMATION FOR SEQ ID NO:27:

( i ) SEQUENCE CHARACTERISTICS:
( A ) LENGTH: 53 amino acids
( B ) TYPE: amino acid
( D ) TOPOLOGY: linear ( x i ) SEQUENCE DESCRIPTION: SEQ ID NO:27:

| Lys | Trp | Arg | Thr | Ser | Arg | Ser | Pro | His | Ala | Gln | Gly | Phe | Ile | Glu | Val |
| 1 | | | | 5 | | | | | 10 | | | | | 15 | |

| Asp | Gln | Asn | Val | Thr | Thr | His | His | Pro | Ile | Val | Arg | Glu | Glu | Lys | Ile |
| | | | 20 | | | | 25 | | | | | 30 | | | |

| Val | Pro | Asn | Met | Gln | Ile | Asn | Gly | Tyr | Glu | Asn | Pro | Thr | Tyr | Lys | Tyr |
| | | 35 | | | | | 40 | | | | | 45 | | | |

| Phe | Glu | Val | Lys | Glu |
| | | 50 | | |

( 2 ) INFORMATION FOR SEQ ID NO:28:

( i ) SEQUENCE CHARACTERISTICS:
( A ) LENGTH: 47 amino acids
( B ) TYPE: amino acid
( D ) TOPOLOGY: linear ( x i ) SEQUENCE DESCRIPTION: SEQ ID NO:28:

| Arg | Lys | Arg | Gln | Tyr | Gly | Thr | Ile | Ser | His | Gly | Ile | Val | Glu | Val | Asp |
| 1 | | | | 5 | | | | | 10 | | | | | 15 | |

| Pro | Met | Leu | Thr | Pro | Glu | Glu | Arg | His | Leu | Asn | Lys | Met | Gln | Asn | His |
| | | | 20 | | | | 25 | | | | | 30 | | | |

| Gly | Tyr | Glu | Asn | Pro | Thr | Tyr | Lys | Tyr | Leu | Glu | Gln | Met | Gln | Ile |
| | | 35 | | | | | 40 | | | | | 45 | | |

( 2 ) INFORMATION FOR SEQ ID NO:29:

( i ) SEQUENCE CHARACTERISTICS:
( A ) LENGTH: 706 amino acids
( B ) TYPE: amino acid ( D ) TOPOLOGY: linear ( x i ) SEQUENCE DESCRIPTION: SEQ ID NO:29:

| Met | Ala | Ala | Thr | Gly | Thr | Ala | Ala | Arg | Ala | Ala | Thr | Gly | Arg | Leu | Leu |
|---|---|---|---|---|---|---|---|---|---|---|---|---|---|---|---|
| 1 | | | | 5 | | | | | 10 | | | | | 15 | |
| Leu | Leu | Leu | Leu | Val | Gly | Leu | Thr | Ala | Pro | Ala | Ala | Ala | Leu | Ala | Gly |
| | | | 20 | | | | 25 | | | | | 30 | | | |
| Tyr | Ile | Glu | Ala | Leu | Ala | Ala | Ala | Ala | Gly | Thr | Gly | Phe | Ala | Val | Ala |
| | | 35 | | | | | 40 | | | | | 45 | | | |
| Glu | Pro | Gln | Ile | Ala | Met | Phe | Cys | Gly | Lys | Leu | Asn | Met | His | Val | Asn |
| | 50 | | | | | 55 | | | | | 60 | | | | |
| Ile | Gln | Thr | Gly | Lys | Trp | Glu | Pro | Asp | Pro | Thr | Gly | Thr | Lys | Ser | Cys |
| 65 | | | | | 70 | | | | | 75 | | | | | 80 |
| Phe | Arg | Thr | Lys | Glu | Glu | Val | Leu | Gln | Tyr | Cys | Gln | Glu | Met | Tyr | Pro |
| | | | | 85 | | | | | 90 | | | | | 95 | |
| Glu | Leu | Gln | Ile | Thr | Asn | Val | Met | Glu | Ala | Asn | Gln | Arg | Val | Ser | Ile |
| | | | | 100 | | | | | 105 | | | | | 110 | |
| Asp | Asn | Trp | Cys | Arg | Arg | Asp | Lys | Lys | Gln | Cys | Lys | Ser | Arg | Phe | Val |
| | | | 115 | | | | | 120 | | | | | 125 | | |
| Thr | Pro | Phe | Lys | Cys | Leu | Val | Gly | Glu | Phe | Val | Ser | Asp | Val | Leu | Leu |
| | 130 | | | | | 135 | | | | | 140 | | | | |
| Val | Pro | Glu | Lys | Cys | Arg | Phe | Phe | His | Lys | Glu | Arg | Met | Glu | Val | Cys |
| 145 | | | | | 150 | | | | | 155 | | | | | 160 |
| Glu | Asn | His | Gln | His | Trp | His | Thr | Val | Val | Lys | Glu | Ala | Cys | Leu | Thr |
| | | | | 165 | | | | | 170 | | | | | 175 | |
| Gln | Gly | Met | Thr | Leu | Tyr | Ser | Tyr | Gly | Met | Leu | Leu | Pro | Cys | Gly | Val |
| | | | 180 | | | | | 185 | | | | | 190 | | |
| Asp | Gln | Phe | His | Gly | Thr | Glu | Tyr | Val | Cys | Cys | Pro | Gln | Thr | Lys | Asp |
| | | 195 | | | | | 200 | | | | | 205 | | | |
| Tyr | Trp | Ser | Val | Ser | Lys | Glu | Glu | Glu | Glu | Glu | Asp | Glu | Glu | Glu | |
| | 210 | | | | | 215 | | | | | 220 | | | | |
| Glu | Glu | Glu | Glu | Asp | Glu | Glu | Asp | Tyr | Asp | Val | Tyr | Lys | Ser | Glu | |
| 225 | | | | | 230 | | | | | 235 | | | | | 240 |
| Phe | Pro | Thr | Glu | Ala | Asp | Leu | Glu | Asp | Phe | Thr | Glu | Ala | Ala | Val | Asp |
| | | | | 245 | | | | | 250 | | | | | 255 | |
| Glu | Asp | Asp | Glu | Asp | Glu | Glu | Glu | Gly | Glu | Glu | Val | Val | Glu | Asp | Arg |
| | | | 260 | | | | | 265 | | | | | 270 | | |
| Asp | Tyr | Tyr | Tyr | Asp | Thr | Phe | Lys | Gly | Asp | Asp | Tyr | Asn | Glu | Glu | Asn |
| | | 275 | | | | | 280 | | | | | 285 | | | |
| Pro | Thr | Glu | Pro | Gly | Ser | Asp | Gly | Thr | Met | Ser | Asp | Lys | Glu | Ile | Thr |
| | 290 | | | | | 295 | | | | | 300 | | | | |
| His | Asp | Val | Lys | Val | Pro | Pro | Thr | Pro | Leu | Pro | Thr | Asn | Asp | Val | Asp |
| 305 | | | | | 310 | | | | | 315 | | | | | 320 |
| Val | Tyr | Phe | Glu | Thr | Ser | Ala | Asp | Asp | Asn | Glu | His | Ala | Arg | Phe | Gln |
| | | | | 325 | | | | | 330 | | | | | 335 | |
| Lys | Ala | Glu | Lys | Glu | Gln | Leu | Ile | Glu | Arg | His | Arg | Asn | Arg | Met | Asp |
| | | | 340 | | | | | 345 | | | | | 350 | | |
| Arg | Val | Lys | Lys | Glu | Trp | Glu | Glu | Ala | Glu | Leu | Gln | Ala | Lys | Asn | Leu |
| | | 355 | | | | | 360 | | | | | 365 | | | |
| Pro | Lys | Ala | Glu | Arg | Gln | Thr | Leu | Ile | Gln | His | Phe | Gln | Ala | Met | Val |
| | 370 | | | | | 375 | | | | | 380 | | | | |
| Lys | Ala | Leu | Glu | Lys | Ala | Glu | Ala | Ser | Glu | Lys | Gln | Gln | Leu | Val |
| 385 | | | | | 390 | | | | | 395 | | | | | 400 |
| Glu | Thr | His | Leu | Ala | Arg | Val | Glu | Ala | Met | Leu | Asn | Asp | Arg | Arg | Met |

|     |     |     |     | 405 |     |     |     | 410 |     |     |     | 415 |     |
|-----|-----|-----|-----|-----|-----|-----|-----|-----|-----|-----|-----|-----|-----|
| Ala | Leu | Glu | Asn | Tyr | Leu | Ala | Ala | Leu | Gln | Arg | Ser | Asp | Pro | Pro | Arg |
|     |     |     | 420 |     |     |     | 425 |     |     |     |     | 430 |     |
| Pro | His | Arg | Ile | Leu | Gln | Pro | Leu | Arg | Arg | Tyr | Val | Arg | Ala | Glu | Asn |
|     |     | 435 |     |     |     |     | 440 |     |     |     |     | 445 |
| Lys | Asp | Arg | Leu | His | Thr | Ile | Arg | His | Tyr | Gln | His | Val | Leu | Ala | Val |
|     | 450 |     |     |     |     | 455 |     |     |     |     |     | 460 |
| Asp | Pro | Glu | Lys | Ala | Ala | Gln | Met | Lys | Ser | Gln | Val | Met | Thr | His | Leu |
| 465 |     |     |     |     | 470 |     |     |     |     | 475 |     |     |     |     | 480 |
| His | Val | Ile | Glu | Glu | Arg | Arg | Asn | Gln | Ser | Leu | Ser | Leu | Leu | Tyr | Lys |
|     |     |     |     | 485 |     |     |     |     | 490 |     |     |     |     | 495 |
| Asp | Pro | Tyr | Val | Ala | Arg | Ile | Gln | Glu | Asn | Asp | Glu | Leu | Leu | Gln | Ala |
|     |     |     | 500 |     |     |     |     | 505 |     |     |     |     | 510 |
| Glu | Arg | Ala | Asp | Met | Asp | Gln | Phe | Thr | Ala | Ser | Ile | Ser | Glu | Thr | Pro |
|     |     | 515 |     |     |     |     | 520 |     |     |     |     | 525 |
| Val | Asp | Val | Arg | Val | Ser | Ser | Glu | Glu | Ser | Glu | Glu | Ile | Pro | Pro | Phe |
|     | 530 |     |     |     |     | 535 |     |     |     |     | 540 |
| His | Pro | Phe | His | Pro | Phe | Pro | Ala | Leu | Pro | Glu | Asn | Glu | Asp | Thr | Gln |
| 545 |     |     |     |     | 550 |     |     |     |     | 555 |     |     |     |     | 560 |
| Pro | Glu | Leu | Tyr | His | Pro | Met | Lys | Lys | Gly | Ser | Gly | Val | Gly | Glu | Gln |
|     |     |     |     | 565 |     |     |     |     | 570 |     |     |     |     | 575 |
| Asp | Gly | Gly | Leu | Ile | Gly | Ala | Glu | Glu | Lys | Val | Ile | Asn | Ser | Lys | Asn |
|     |     |     | 580 |     |     |     |     | 585 |     |     |     |     | 590 |
| Lys | Val | Asp | Glu | Asn | Met | Val | Ile | Asp | Glu | Thr | Leu | Asp | Lys | Glu | Met |
|     |     | 595 |     |     |     |     | 600 |     |     |     |     | 605 |
| Ile | Phe | Asn | Ala | Glu | Arg | Val | Gly | Gly | Leu | Glu | Glu | Arg | Glu | Ser | Val |
|     |     | 610 |     |     |     |     | 615 |     |     |     |     | 620 |
| Gly | Pro | Leu | Arg | Glu | Asp | Phe | Ser | Leu | Ser | Ser | Ser | Ala | Ser | Ile | Gly |
| 625 |     |     |     |     | 630 |     |     |     |     | 635 |     |     |     |     | 640 |
| Leu | Leu | Val | Ile | Ala | Val | Ala | Ile | Ala | Thr | Val | Ile | Val | Ile | Ser | Leu |
|     |     |     |     | 645 |     |     |     |     | 650 |     |     |     |     | 655 |
| Val | Met | Leu | Arg | Lys | Arg | Gln | Val | Cys | Thr | Ile | Ser | His | Gly | Ile | Val |
|     |     |     | 660 |     |     |     |     | 665 |     |     |     |     | 670 |
| Glu | Val | Asp | Pro | Met | Leu | Thr | Pro | Glu | Glu | Arg | His | Leu | Asn | Lys | Met |
|     |     | 675 |     |     |     |     | 680 |     |     |     |     | 685 |
| Gln | Asn | His | Gly | Tyr | Glu | Asn | Pro | Thr | Tyr | Lys | Thr | Leu | Glu | Gln | Met |
|     | 690 |     |     |     |     | 695 |     |     |     |     | 700 |
| Gln | Ile |
| 705 |

( 2 ) INFORMATION FOR SEQ ID NO:30:

( i ) SEQUENCE CHARACTERISTICS:
        ( A ) LENGTH: 695 amino acids
        ( B ) TYPE: amino acid
        ( D ) TOPOLOGY: linear ( x i ) SEQUENCE DESCRIPTION: SEQ ID NO:30:

| Met | Leu | Pro | Gly | Leu | Ala | Leu | Leu | Leu | Ala | Ala | Trp | Thr | Ala | Arg |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ala | Leu | Glu | Val | Pro | Thr | Asp | Gly | Asn | Ala | Gly | Leu | Leu | Ala | Glu | Pro |
|     |     |     | 20  |     |     |     |     | 25  |     |     |     |     | 30  |
| Gln | Ile | Ala | Met | Phe | Cys | Gly | Arg | Leu | Asn | Met | His | Met | Asn | Val | Gln |
|     |     | 35  |     |     |     |     | 40  |     |     |     |     | 45  |
| Asn | Gly | Lys | Trp | Asp | Ser | Asp | Pro | Ser | Gly | Thr | Lys | Thr | Cys | Ile | Asp |
|     | 50  |     |     |     |     | 55  |     |     |     |     | 60  |

```
Thr  Lys  Glu  Gly  Ile  Leu  Gln  Tyr  Cys  Gln  Glu  Val  Tyr  Pro  Glu  Leu
65                  70                      75                      80

Gln  Ile  Thr  Asn  Val  Val  Glu  Ala  Asn  Gln  Pro  Val  Thr  Ile  Gln  Asn
                    85                      90                      95

Trp  Cys  Lys  Arg  Gly  Arg  Lys  Gln  Cys  Lys  Thr  His  Pro  His  Phe  Val
                    100                     105                     110

Ile  Pro  Tyr  Arg  Cys  Leu  Val  Gly  Glu  Phe  Val  Ser  Asp  Ala  Leu  Leu
                    115                     120                     125

Val  Pro  Asp  Lys  Cys  Lys  Phe  Leu  His  Gln  Glu  Arg  Met  Asp  Val  Cys
130                      135                     140

Glu  Thr  His  Leu  His  Trp  His  Thr  Val  Ala  Lys  Glu  Thr  Cys  Ser  Glu
145                      150                     155                     160

Lys  Ser  Thr  Asn  Leu  His  Asp  Tyr  Gly  Met  Leu  Leu  Pro  Cys  Gly  Ile
                    165                     170                     175

Asp  Lys  Phe  Arg  Gly  Val  Glu  Phe  Val  Cys  Cys  Pro  Leu  Ala  Glu  Glu
                    180                     185                     190

Ser  Asp  Asn  Val  Asp  Ser  Ala  Asp  Ala  Glu  Glu  Asp  Asp  Ser  Asp  Val
          195                     200                     205

Trp  Trp  Gly  Gly  Ala  Asp  Thr  Asp  Tyr  Ala  Asp  Gly  Ser  Glu  Asp  Lys
210                      215                     220

Val  Val  Glu  Val  Ala  Glu  Glu  Glu  Val  Ala  Glu  Val  Glu  Glu  Glu
225                      230                     235                     240

Glu  Ala  Asp  Asp  Asp  Glu  Asp  Asp  Glu  Asp  Gly  Asp  Glu  Val  Glu  Glu
                    245                     250                     255

Glu  Ala  Glu  Glu  Pro  Tyr  Glu  Glu  Ala  Thr  Glu  Arg  Thr  Thr  Ser  Ile
               260                     265                     270

Ala  Thr  Thr  Thr  Thr  Thr  Thr  Thr  Glu  Ser  Val  Glu  Glu  Val  Val  Arg
          275                     280                     285

Val  Pro  Thr  Thr  Ala  Ala  Ser  Thr  Pro  Asp  Ala  Val  Asp  Lys  Tyr  Leu
     290                     295                     300

Glu  Thr  Pro  Gly  Asp  Glu  Asn  Glu  His  Ala  His  Phe  Gln  Lys  Ala  Lys
305                      310                     315                     320

Glu  Arg  Leu  Glu  Ala  Lys  His  Arg  Glu  Arg  Met  Ser  Gln  Val  Met  Arg
                    325                     330                     335

Glu  Trp  Glu  Glu  Ala  Glu  Arg  Gln  Ala  Lys  Asn  Leu  Pro  Lys  Ala  Asp
               340                     345                     350

Lys  Lys  Ala  Val  Ile  Gln  His  Phe  Gln  Glu  Lys  Val  Glu  Ser  Leu  Glu
          355                     360                     365

Gln  Glu  Ala  Ala  Asn  Glu  Arg  Gln  Gln  Leu  Val  Glu  Thr  His  Met  Ala
     370                     375                     380

Arg  Val  Glu  Ala  Met  Leu  Asn  Asp  Arg  Arg  Arg  Leu  Ala  Leu  Glu  Asn
385                      390                     395                     400

Tyr  Ile  Thr  Ala  Leu  Gln  Ala  Val  Pro  Pro  Arg  Pro  Arg  His  Val  Phe
                    405                     410                     415

Asn  Met  Leu  Lys  Lys  Tyr  Val  Arg  Ala  Glu  Gln  Lys  Asp  Arg  Gln  His
               420                     425                     430

Thr  Leu  Lys  His  Phe  Glu  His  Val  Arg  Met  Val  Asp  Pro  Lys  Lys  Ala
          435                     440                     445

Ala  Gln  Ile  Arg  Ser  Gln  Val  Met  Thr  His  Leu  Arg  Val  Ile  Tyr  Glu
     450                     455                     460

Arg  Met  Asn  Gln  Ser  Leu  Ser  Leu  Leu  Tyr  Asn  Val  Pro  Ala  Val  Ala
465                      470                     475                     480

Glu  Glu  Ile  Gln  Asp  Glu  Val  Asp  Glu  Leu  Leu  Gln  Lys  Glu  Gln  Asn
```

|     |     |     |     |     | 485 |     |     |     |     | 490 |     |     |     |     | 495 |     |
| --- | --- | --- | --- | --- | --- | --- | --- | --- | --- | --- | --- | --- | --- | --- | --- | --- |
| Tyr | Ser | Asp | Asp | Val | Leu | Ala | Asn | Met | Ile | Ser | Glu | Pro | Arg | Ile | Ser |
|     |     |     | 500 |     |     |     |     | 505 |     |     |     |     | 510 |     |     |
| Tyr | Gly | Asn | Asp | Ala | Leu | Met | Pro | Ser | Leu | Thr | Glu | Thr | Lys | Thr | Thr |
|     |     |     | 515 |     |     |     | 520 |     |     |     |     | 525 |     |     |     |
| Val | Glu | Leu | Leu | Pro | Val | Asn | Gly | Glu | Phe | Ser | Leu | Asp | Asp | Leu | Gln |
|     | 530 |     |     |     |     | 535 |     |     |     |     |     | 540 |     |     |     |
| Pro | Trp | His | Ser | Phe | Gly | Ala | Asp | Ser | Val | Pro | Ala | Asn | Thr | Glu | Asn |
| 545 |     |     |     |     | 550 |     |     |     |     | 555 |     |     |     |     | 560 |
| Glu | Val | Glu | Pro | Val | Asp | Ala | Arg | Pro | Ala | Ala | Asp | Arg | Gly | Leu | Thr |
|     |     |     |     | 565 |     |     |     |     | 570 |     |     |     |     | 575 |     |
| Thr | Arg | Pro | Gly | Ser | Gly | Leu | Thr | Asn | Ile | Lys | Thr | Glu | Glu | Ile | Ser |
|     |     |     | 580 |     |     |     |     | 585 |     |     |     |     | 590 |     |     |
| Glu | Val | Lys | Met | Asp | Ala | Glu | Phe | Arg | His | Asp | Ser | Gly | Tyr | Glu | Val |
|     |     | 595 |     |     |     |     | 600 |     |     |     |     | 605 |     |     |     |
| His | His | Gln | Lys | Leu | Val | Phe | Phe | Ala | Glu | Asp | Val | Gly | Ser | Asn | Lys |
|     | 610 |     |     |     |     |     | 615 |     |     |     |     | 620 |     |     |     |
| Gly | Ala | Ile | Ile | Gly | Leu | Asn | Val | Gly | Gly | Val | Val | Ile | Ala | Thr | Val |
| 625 |     |     |     |     | 630 |     |     |     |     | 635 |     |     |     |     | 640 |
| Ile | Val | Ile | Thr | Leu | Val | Met | Leu | Lys | Lys | Lys | Gln | Tyr | Thr | Ser | Ile |
|     |     |     |     | 645 |     |     |     |     | 650 |     |     |     |     | 655 |     |
| His | Glu | Gly | Val | Val | Glu | Val | Asp | Ala | Ala | Val | Thr | Pro | Glu | Glu | Arg |
|     |     |     | 660 |     |     |     |     | 665 |     |     |     |     | 670 |     |     |
| His | Leu | Ser | Lys | Met | Gln | Gln | Asn | Gly | Tyr | Glu | Asn | Pro | Thr | Thr | Lys |
|     |     | 675 |     |     |     |     | 680 |     |     |     |     | 685 |     |     |     |
| Phe | Phe | Glu | Gln | Met | Gln | Asn |
|     |     | 690 |     |     |     | 695 |

(2) INFORMATION FOR SEQ ID NO:31:

(i) SEQUENCE CHARACTERISTICS:
        (A) LENGTH: 507 amino acids
        (B) TYPE: amino acid
        (D) TOPOLOGY: linear (xi) SEQUENCE DESCRIPTION: SEQ ID NO:31:

| Met | Pro | Leu | Leu | Leu | Leu | Leu | Ala | Trp | Thr | Ala | Ala | Val | Gly | Ala | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ala | Glu | Pro | Gln | Ile | Ala | Met | Phe | Cys | Gly | Arg | Leu | Asn | Met | His | Val |
|     |     |     | 20  |     |     |     |     | 25  |     |     |     |     | 30  |     |     |
| Asn | Val | Gln | Gly | Lys | Trp | Asp | Ser | Asp | Pro | Gly | Thr | Lys | Cys | Ile | Thr |
|     |     |     | 35  |     |     |     | 40  |     |     |     |     | 45  |     |     |     |
| Lys | Glu | Gly | Ile | Leu | Gln | Tyr | Cys | Gln | Glu | Val | Tyr | Pro | Glu | Leu | Gln |
|     |     | 50  |     |     |     |     | 55  |     |     |     |     | 60  |     |     |     |
| Ile | Thr | Asn | Val | Val | Glu | Ala | Asn | Gln | Pro | Val | Ile | Gln | Asn | Trp | Cys |
| 65  |     |     |     |     | 70  |     |     |     |     | 75  |     |     |     |     | 80  |
| Lys | Arg | Asp | Arg | Lys | Gln | Cys | Lys | His | Phe | Val | Ile | Pro | Tyr | Arg | Cys |
|     |     |     |     | 85  |     |     |     |     | 90  |     |     |     |     | 95  |     |
| Leu | Val | Gly | Glu | Phe | Val | Ser | Asp | Ala | Leu | Leu | Val | Pro | Asp | Lys | Cys |
|     |     |     |     | 100 |     |     |     |     | 105 |     |     |     |     | 110 |     |
| Lys | Phe | Leu | His | Gln | Glu | Arg | Met | Asp | Val | Cys | Glu | His | His | Trp | His |
|     |     |     | 115 |     |     |     |     | 120 |     |     |     |     | 125 |     |     |
| Thr | Val | Ala | Lys | Glu | Cys | Ser | Ser | Leu | His | Asp | Tyr | Gly | Met | Leu | Leu |
|     | 130 |     |     |     |     | 135 |     |     |     |     | 140 |     |     |     |     |
| Pro | Cys | Gly | Asp | Asp | Lys | Phe | Arg | Gly | Val | Glu | Phe | Val | Cys | Cys | Pro |
| 145 |     |     |     |     | 150 |     |     |     |     | 155 |     |     |     |     | 160 |

```
Ala  Glu  Asp  Val  Ala  Asp  Glu  Glu  Asp  Asp  Asp  Gly  Gly  Asp  Asp  Asp
               165            170                 175

Gly  Glu  Glu  Ala  Ile  Glu  Glu  Val  Glu  Glu  Asp  Asp  Asp  Glu  Asp  Asp
               180            185                 190

Glu  Asp  Gly  Asp  Glu  Val  Glu  Glu  Glu  Glu  Tyr  Glu  Glu  Glu  Arg  Thr
          195            200                 205

Ala  Thr  Thr  Thr  Val  Val  Val  Arg  Val  Pro  Thr  Ala  Thr  Asp  Ala  Val
     210                 215                 220

Asp  Tyr  Leu  Glu  Thr  Pro  Gly  Asp  Glu  Asn  Glu  His  Ala  His  Phe  Gln
225                      230                 235                           240

Lys  Ala  Lys  Glu  Leu  Glu  Lys  His  Arg  Glu  Arg  Met  Gln  Val  Met  Arg
                    245                 250                      255

Glu  Trp  Glu  Glu  Ala  Glu  Gln  Ala  Lys  Asn  Leu  Pro  Lys  Ala  Asp  Lys
               260                      265                 270

Ala  Val  Ile  Gln  His  Phe  Gln  Val  Glu  Leu  Glu  Gln  Glu  Ala  Ala  Glu
               275                 280                      285

Arg  Gln  Gln  Leu  Val  Glu  Thr  His  Met  Ala  Arg  Val  Glu  Ala  Met  Leu
          290                 295                      300

Asn  Asp  Arg  Arg  Leu  Ala  Leu  Glu  Asn  Tyr  Ile  Ala  Leu  Gln  Ala  Pro
305                      310                 315                           320

Pro  Arg  Pro  Val  Phe  Leu  Lys  Lys  Tyr  Val  Arg  Ala  Glu  Gln  Lys  Asp
               325                 330                      335

Arg  His  Thr  Leu  Lys  His  Phe  Glu  His  Val  Val  Asp  Pro  Lys  Ala  Ala
               340                 345                      350

Gln  Ile  Arg  Ser  Gln  Val  Met  Thr  His  Leu  Arg  Val  Ile  Glu  Arg  Met
          355                 360                      365

Asn  Gln  Ser  Leu  Ser  Leu  Leu  Tyr  Pro  Val  Ala  Glu  Glu  Ile  Asp  Glu
370                      375                 380

Asp  Glu  Leu  Leu  Gln  Glu  Ala  Asn  Met  Asp  Leu  Pro  Ser  Leu  Glu  Thr
385                 390                 395                           400

Val  Leu  Asn  Gly  Glu  Ser  Leu  Leu  Gln  Pro  Trp  His  Phe  Ala  Asn  Thr
               405                 410                      415

Glu  Glu  Val  Glu  Asp  Ala  Ala  Ala  Leu  Ser  Gly  Asn  Ile  Glu  Glu  Glu
               420                 425                      430

Lys  Met  Ala  Glu  Lys  Ser  Gly  Glu  His  Gln  Leu  Phe  Glu  Asp  Gly  Gly
          435                 440                      445

Ala  Ile  Gly  Leu  Met  Val  Gly  Val  Ile  Ala  Thr  Val  Ile  Val  Ile  Leu
     450                 455                      460

Val  Met  Leu  Lys  Lys  Lys  Gln  Tyr  Ile  His  Gly  Val  Val  Glu  Val  Asp
465                      470                 475                           480

Ala  Val  Thr  Pro  Glu  Glu  Arg  His  Leu  Lys  Met  Gln  Asn  Gly  Tyr  Glu
               485                 490                      495

Asn  Pro  Thr  Tyr  Lys  Phe  Phe  Glu  Gln  Met  Gln
               500                 505
```

( 2 ) INFORMATION FOR SEQ ID NO:32:

( i ) SEQUENCE CHARACTERISTICS:
        ( A ) LENGTH: 532 amino acids
        ( B ) TYPE: amino acid
        ( D ) TOPOLOGY: linear ( x i ) SEQUENCE DESCRIPTION: SEQ ID NO:32:

```
Met  Ala  Ala  Thr  Gly  Ala  Ala  Arg  Leu  Leu  Leu  Leu  Leu  Val  Gly  Leu
1                   5                   10                      15
```

```
Thr Ala Ala Ala Ala Leu Ala Ala Leu Ala Ala Gly Ala Val Ala Glu
         20              25              30
Pro Gln Ile Ala Met Phe Cys Gly Lys Leu Asn Met His Met Asn Ile
             35              40              45
Gln Thr Gly Lys Trp Glu Pro Asp Pro Gly Thr Lys Cys Phe Thr Lys
        50              55              60
Glu Val Leu Gln Tyr Cys Gln Glu Met Tyr Pro Glu Leu Gln Ile
65              70              75              80
Thr Asn Val Met Glu Ala Asn Gln Val Ile Asp Asn Trp Cys Arg Arg
                85              90              95
Gly Lys Lys Gln Cys Lys Arg Phe Val Pro Phe Lys Cys Leu Val Gly
            100             105             110
Glu Phe Val Ser Asp Leu Leu Val Pro Glu Lys Cys Arg Phe Phe His
        115             120             125
Glu Arg Met Glu Val Cys Glu His His Trp His Thr Val Lys Glu Ala
    130             135             140
Cys Gln Gly Leu Ser Tyr Gly Met Leu Leu Pro Cys Gly Val Asp Phe
145             150             155             160
His Gly Glu Tyr Val Cys Cys Pro Asp Val Ser Glu Glu Glu Glu Asp
                165             170             175
Glu Glu Glu Glu Glu Asp Glu Glu Glu Asp Asp Glu Pro Glu Asp Leu
            180             185             190
Glu Asp Phe Glu Asp Asp Glu Asp Glu Glu Glu Gly Glu Glu Val
    195             200             205
Glu Asp Asp Tyr Asp Glu Glu Pro Thr Pro Gly Ser Thr Ile Val Lys
    210             215             220
Val Pro Pro Thr Pro Thr Asp Val Asp Val Tyr Phe Glu Thr Ala
225             230             235             240
Asp Asp Asn Glu His Ala Arg Phe Gln Lys Ala Lys Glu Gln Leu Glu
                245             250             255
Arg His Arg Asn Arg Met Asp Val Lys Glu Trp Glu Glu Ala Glu Gln
            260             265             270
Ala Lys Asn Leu Pro Lys Ala Glu Arg Gln Leu Ile Gln His Phe Gln
        275             280             285
Met Val Leu Glu Glu Ala Ala Ser Glu Gln Gln Leu Val Glu Thr His
    290             295             300
Leu Ala Arg Val Glu Ala Met Leu Asn Asp Arg Arg Met Ala Leu Glu
305             310             315             320
Asn Tyr Leu Ala Ala Leu Gln Ser Asp Pro Pro Arg Pro Arg Ile Leu
                325             330             335
Pro Leu Arg Arg Tyr Val Arg Ala Glu Lys Asp Arg His Thr Ile Arg
            340             345             350
His Tyr Gln His Val Ala Val Asp Pro Glu Lys Ala Ala Gln Met Lys
        355             360             365
Ser Gln Val Met Thr His Leu His Val Ile Glu Glu Arg Asn Gln Ser
    370             375             380
Leu Ser Leu Leu Tyr Asp Pro Val Ala Gln Glu Asp Glu Leu Leu Gln
385             390             395             400
Ala Glu Arg Ala Asp Met Asp Phe Ala Ser Ile Ser Glu Thr Val Val
                405             410             415
Ser Ser Glu Ser Glu Ile Pro Phe His Pro Phe His Pro Phe Pro Ala
            420             425             430
Asp Thr Gln Glu Leu Glu Gly Gly Gly Ala Val Ser Glu Asn Met Asp
        435             440             445
```

| | | | | | | | | | | | | | | |
|---|---|---|---|---|---|---|---|---|---|---|---|---|---|---|
|Glu|Asp|Met|Asn|Ala|Arg|Gly|Gly|Leu|Glu|Glu|Arg|Glu|Val|Gly|Leu|
| |450| | | | |455| | | |460| | | | |
|Glu|Asp|Ser|Ser|Ser|Ala|Ile|Gly|Leu|Leu|Val|Ile|Ala|Val|Ala|Ile|
| |465| | | |470| | | |475| | | | |480|
|Ala|Thr|Val|Ile|Val|Ile|Ser|Leu|Val|Met|Leu|Arg|Lys|Arg|Gln|Thr|
| | | | |485| | | |490| | | | |495| |
|Ile|Ser|His|Gly|Ile|Val|Glu|Val|Asp|Pro|Met|Leu|Thr|Pro|Glu|Glu|
| | | |500| | | |505| | | |510| | | |
|Arg|His|Leu|Lys|Met|Gln|His|Gly|Tyr|Glu|Asn|Pro|Thr|Tyr|Lys|Leu|
| | |515| | | |520| | | |525| | | | |
|Glu|Gln|Met|Gln|
| | |530| |

( 2 ) INFORMATION FOR SEQ ID NO:33:

( i ) SEQUENCE CHARACTERISTICS:
( A ) LENGTH: 429 amino acids
( B ) TYPE: amino acid
( D ) TOPOLOGY: linear ( x i ) SEQUENCE DESCRIPTION: SEQ ID NO:33:

| | | | | | | | | | | | | | | |
|---|---|---|---|---|---|---|---|---|---|---|---|---|---|---|---|
|Met|Gly|Pro|Thr|Ser|Ala|Ala|Arg|Pro|Leu|Leu|Leu|Leu|Leu|Ser|Leu|
|1| | | |5| | | | |10| | | | |15| |
|Ala|Leu|Ala|Ala|Val|Gly|Pro|Ala|Ala|Gly|Ala|Gln|Val|Ala|Leu|Cys|
| | | |20| | | | |25| | | | |30| | |
|Gly|Arg|Leu|Leu|His|Asp|Leu|Thr|Gly|Arg|Trp|Glu|Pro|Asp|Pro|Ser|
| | |35| | | | |40| | | | |45| | | |
|Arg|Cys|Leu|Gln|Val|Leu|Glu|Tyr|Cys|Gln|Met|Tyr|Pro|Glu|Leu|His|
| |50| | | | |55| | | | |60| | | | |
|Ile|Val|Gln|Ala|Gln|Ala|Ile|Met|Glu|Trp|Cys|Arg|Cys|His|Val|Val|
|65| | | |70| | | | |75| | | | | |80|
|Pro|Phe|Cys|Leu|Pro|Gly|Glu|Phe|Val|Ser|Glu|Ala|Leu|Leu|Val|Pro|
| | | | |85| | | | |90| | | | |95| |
|Glu|Gly|Cys|Arg|Phe|Leu|His|Gln|Glu|Arg|Met|Asp|Cys|Glu|Arg|Arg|
| | | |100| | | | |105| | | | |110| | |
|His|Ala|Glu|Ala|Cys|Ser|Ser|Gln|Gly|Leu|His|Gly|Gly|Met|Leu|Leu|
| | |115| | | | |120| | | | |125| | | |
|Pro|Cys|Gly|Asp|Arg|Phe|Arg|Gly|Val|Glu|Tyr|Val|Cys|Cys|Pro|Pro|
| |130| | | | |135| | | | |140| | | | |
|Asn|Gly|Ala|Asp|Gly|Gly|Glu|Gly|Gly|Glu|Asp|Glu|Glu|Glu|Val|Glu|
|145| | | |150| | | | |155| | | | | |160|
|Phe|Gln|Asp|Glu|Gln|Glu|Glu|Glu|Glu|Glu|Glu|Arg|Ala|Pro|Ser|
| | | | |165| | | | |170| | | | |175| |
|Thr|Val|Arg|Val|Pro|Thr|Pro|Thr|Asp|Gly|Val|Asp|Val|Tyr|Phe|
| | | |180| | | | |185| | | | |190| | |
|Gly|Pro|Gly|Glu|Glu|His|Phe|Arg|Ala|Lys|Asp|Leu|Glu|Glu|Arg|Arg|
| | |195| | | | |200| | | | |205| | | |
|Ile|Asn|Glu|Val|Met|Arg|Glu|Trp|Ala|Asp|Gln|Lys|Asn|Leu|Pro|Lys|
| |210| | | | |215| | | | |220| | | | |
|Ala|Asp|Arg|Gln|Ala|Leu|Glu|His|Phe|Gln|Ile|Leu|Gln|Leu|Glu|Glu|
|225| | | |230| | | | |235| | | | | |240|
|Glu|Gln|Gly|Glu|Arg|Gln|Leu|Val|Glu|Thr|His|Arg|Val|Ala|Leu|Ile|
| | | | |245| | | | |250| | | | |255| |
|Asn|Asp|Arg|Arg|Ala|Leu|Glu|Phe|Leu|Ala|Ala|Leu|Gln|Gly|Asp|Pro|
| | | |260| | | | |265| | | | |270| | |

| | | | | | | | | | | | | | | |
|---|---|---|---|---|---|---|---|---|---|---|---|---|---|---|
| Pro | Ala | Arg 275 | Val | Leu | Ala | Leu | Arg 280 | Arg | Tyr | Leu | Arg | Ala 285 | Glu | Gln | Lys |
| Glu | His 290 | Thr | Leu | Arg | His | Tyr 295 | Gln | His | Val | Ala | Val 300 | Asp | Pro | Glu | Lys |
| Ala 305 | Gln | Met | Arg | Gln | Val 310 | Thr | His | Leu | Val | Ile 315 | Glu | Glu | Arg | Met | Asn 320 |
| Gln | Ser | Leu | Gly | Leu 325 | Leu | Asn | Pro | Leu | Ala 330 | Gln | Glu | Leu | Gln | Gln 335 | Glu |
| Leu | Leu | Ala | Glu 340 | His | Ser | Glu | Val | Ser 345 | Ser | Glu | Ser | Leu | Pro 350 | Asp | Pro |
| Pro | Thr | Glu 355 | Ser | Ser | Gly | Glu | Glu 360 | Glu | Lys | Ala | Ala | Arg 365 | Phe | Asp | Gln |
| Arg | Asp 370 | Leu | Ala | Gly | Gly | Ser 375 | Ala | Gly | Leu | Leu | Ile 380 | Met | Gly | Gly | Gly |
| Leu 385 | Ile | Val | Leu | Ser | Leu 390 | Leu | Leu | Leu | Arg | Lys 395 | Lys | Tyr | Thr | Ile | Ser 400 |
| His | Gly | Val | Val | Glu 405 | Val | Asp | Pro | Met | Leu 410 | Thr | Glu | Glu | Gln | Leu 415 | Leu |
| Gln | His | Gly | Tyr 420 | Glu | Asn | Pro | Thr | Tyr 425 | Phe | Leu | Glu | Glu | | | |